(12) United States Patent
Thompson et al.

(10) Patent No.: US 6,906,064 B2
(45) Date of Patent: Jun. 14, 2005

(54) METHOD FOR TREATING A PATIENT WITH NEOPLASIA USING IRESSA

(76) Inventors: W. Joseph Thompson, 443 Maple Ave., Doylestown, PA (US) 19044; Hector W. Alila, 1268 Turnbury La., North Wales, PA (US) 19454

( * ) Notice: Subject to any disclaimer, the term of this patent is extended or adjusted under 35 U.S.C. 154(b) by 0 days.

(21) Appl. No.: 10/166,940

(22) Filed: Jun. 10, 2002

(65) Prior Publication Data

US 2003/0232862 A1 Dec. 18, 2003

(51) Int. Cl.[7] .................... A61K 31/535; A61K 31/445
(52) U.S. Cl. .................................. 514/234.5; 514/319
(58) Field of Search ............................ 514/319, 234.5, 514/234.8, 357

(56) References Cited

U.S. PATENT DOCUMENTS 5,948,779 A * 9/1999 Sperl et al. ................ 514/241

OTHER PUBLICATIONS

Stein, J. H., Editor–in–Chief, Internal Medicine, Fourth Edition, Chapters 71 and 72, 1994.*
Ciardiello, F, "Epidermal growth factor receptor tyrosine kinase inhibitors as anticancer agents", DRUGS, 60 Suppl 1, 25–32, 2000.*
Barker et al. .2001, Bioorganic and Medicinal Chemistry Letters 14:1911–1914.

Chan et al. 2002, Cancer Res. 62:122–128.

Ciardello et al. 2001, Cancer Res. 7:1459–1465.

Moasser et al. 2001, Cancer Res. 61:17184–7188.

Moulder et al. 2001, Cancer Res. 61:8887–8895.

Piazza et al. 1995, Cancer Research 55:3110–3116.

Piazza et al. 1997, Cancer Research 57:2452–2459.

Ranson et al. 2002, J. Clin Oncology 20:2240–2250.

Thompson et al. 1995, Journal of the National Cancer Institute 87:1259–1260.

* cited by examiner

*Primary Examiner*—Dwayne C. Jones
(74) *Attorney, Agent, or Firm*—Alexander Stewart; Shu M. Lee

(57) ABSTRACT

This invention provides a method for treating a patient with neoplasia by an adjuvant therapy that includes treatment with an inhibitor of human epidermal growth factor receptor tyrosine kinase and a cGMP-specific phosphodiesterase inhibitor.

3 Claims, 22 Drawing Sheets

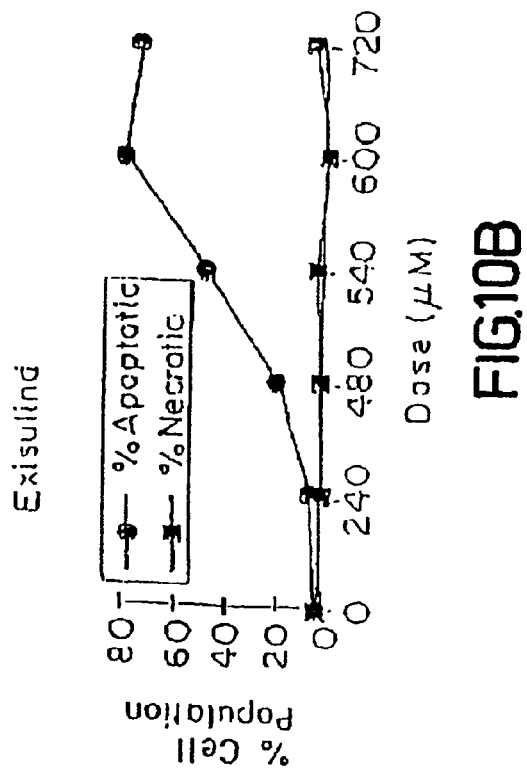
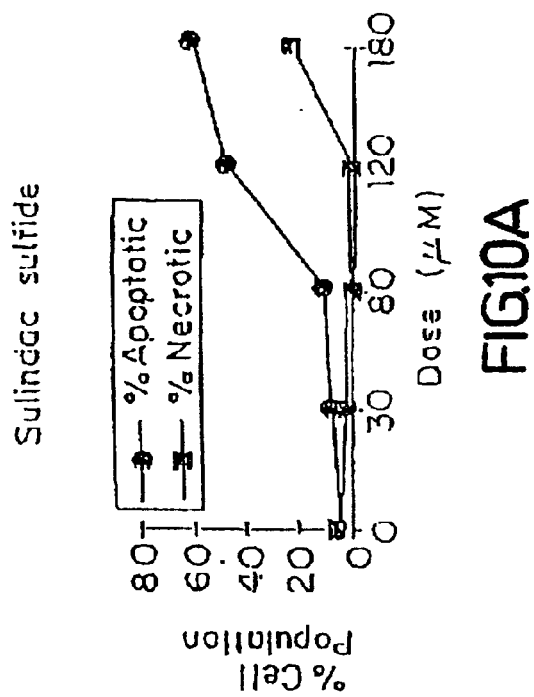

METHOD FOR TREATING A PATIENT WITH NEOPLASIA USING IRESSA

BACKGROUND OF THE INVENTION

Virtually all of the many anti-neoplastic drugs that are currently used in the treatment of cancer have very serious and harmful side effects. This is because cancer is generally treated with medications that interfere with the growth of rapidly dividing cells. Such medications can inhibit the growth of the cancer cells, but they almost always also inhibit the growth of normal cells that divide rapidly in the body. Some of the normal tissues that divide very rapidly include bone marrow (which produces blood cells), hair follicles, and intestinal epithelium. The usefulness of virtually all anti-neoplastic drugs is severely limited by the damage they cause to these normal tissues.

This invention relates to methods for treating neoplasia using both Iressa (chemical name 4-quinazolinamine, N-(3-chloro-4-fluorophenyl)-7-methoxy-6-[3-(4-morpholinyl) propoxy]-(9CI)) and a cyclic GMP (cGMP)-specific phosphodiesterase (PDE) inhibitor to reduce the side effects or increase the efficacy of inhibitor treatment. Iressa has been used to treat certain cancers, particularly non-small cell lung cancer, particularly in patients where at least a first-line chemotherapy has failed. Under current practice, many types of therapy are typically used after first-line failure because they are so toxic and their side effects are so bad that the risks of the therapy outweigh the benefits until other chemotherapeutic options commonly have been exhausted.

SUMMARY OF THE INVENTION

This invention relates to an improved method of cancer therapy that involves treating a patient with both Iressa and a cyclic GMP-specific phosphodiesterase (PDE) inhibitor. The specific PDE inhibitors useful for this invention are compounds that inhibit both PDE5 and the types of PDE2 described below. The novel form of PDE2 disclosed herein is fully described by Liu, et al., in U.S. Pat. No. 6,200,771, A Novel Cyclic GMP-Specific Phosphodiesterase And Methods For Using Same In Pharmaceutical Screening For Identifying Compounds For Inhibition of Neoplastic Lesions (for general background, see, Beavo, J. A. (1995) Cyclic nucleotide phosphodiesterases: functional implications of multiple isoforms. Physiological Reviews 75:725–747.

BRIEF DESCRIPTION OF THE DRAWINGS

FIGS. 10A and 10B illustrate the effects of sulindac sulfide and exisulind on apoptosis and necrosis in HT-29 cells.

DETAILED DESCRIPTION OF THE PREFERRED EMBODIMENTS

Figure 1:
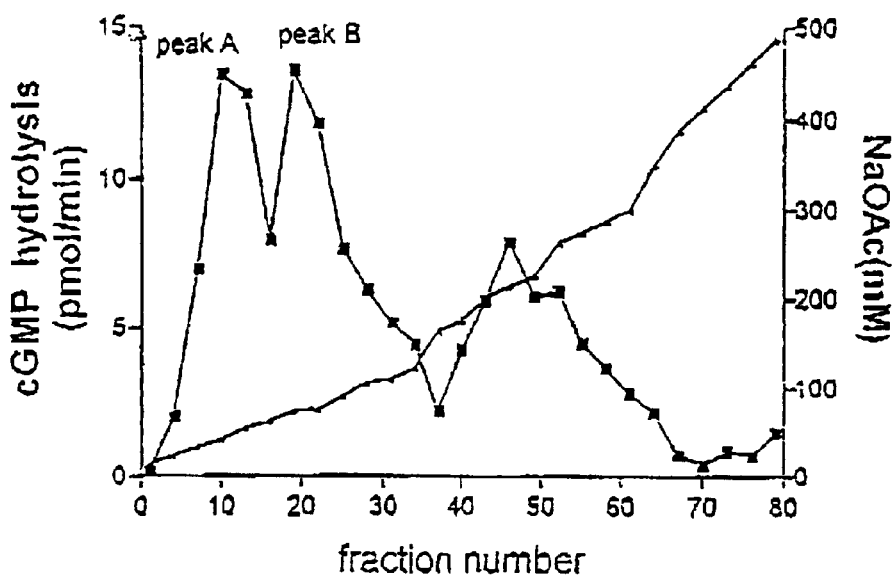
FIG. 1 is a graph of the cGMP activities of the cGMP phosphodiesterases obtained from SW480 neoplastic cells, as assayed from the eluent from a DEAE-Trisacryl M column.

As discussed in greater detail below, the inhibition of cGMP-specific PDEs can induce apoptosis in neoplastic cells. Human epidermal growth factor receptor tyrosine kinase inhibitor therapies are currently used to treat neoplasias, particularly breast cancers. The combination of these two types of therapies can produce an effect that neither can produce individually, specifically achieving synergistic effects as presented below.

As explained above, this invention among other things is a method of causing the use of a particular class of anti-neoplastic cGMP PDE inhibitor that acts through the pathways described herein, in conjunction with an inhibitor of human epidermal growth factor receptor tyrosine kinase-based therapeutic. This method includes obtaining a pharmaceutical composition that includes such an inhibitor having one or more of the attributes set forth herein, informing physicians and patients about those attributes, providing the pharmaceutical composition to physicians and patients in need of treatment; and causing a patient to receive the pharmaceutical composition in conjunction with human epidermal growth factor receptor tyrosine kinase inhibitor therapy. This invention also involves obtaining a pharmaceutical composition that includes a human epidermal growth factor receptor tyrosine kinase inhibitor, providing the pharmaceutical composition to physicians and patients in need of treatment; and causing a patient to receive the pharmaceutical composition in conjunction with an anti-neoplastic cGMP PDE inhibitor.

By "informing the physician and patient," we mean the entire range of direct or indirect medical educational efforts whereby pharmaceuticals are (in effect) marketed to doctors, and thereby their patients. By way of example only, one way is for the manufacturer to conduct the required mechanistic studies (of the type described below) to ascertain whether his compound has the attributes set forth herein, and then publishing the results of those studies in one or more publications or including such information in a package insert that accompanies the pharmaceutical. Alternatively, pharmaceutical companies can sponsor or initiate such mechanistic studies to be performed by third parties, and the results of those third party studies are then published.

Those reports are then used by the pharmaceutical company in its medical education and marketing efforts. For example, copies of published reports can be distributed by the company or its agents directly to doctors at conventions or in their offices in an effort to convince the physician that the drug indeed has the attributes that warrant use. Alternatively, those reports can be posted on the Internet directly or indirectly by the company or its agents. Also, the company can arrange for (or have arranged for it) continuing medical education carriers to organize events where doctors are provided such data. These and similar efforts are used by pharmaceutical companies to inform physicians and thereby the patients so that the prescribers and users of such pharmaceuticals come to understand that the drug sold by the manufacturer has one or more of the attributes set forth herein.

By "packaged pharmaceutical," we mean the drug (either the anti-neoplastic cGMP PDE inhibitor or the human epidermal growth factor receptor tyrosine kinase inhibitor) as formulated in its form to be administered to the patient) packaged in a bottle or blister card (that may or may not then be boxed with other bottles or blister cards), IV bag, aerosol inhaler, syringe, ointment tube, or the like. The "written material" is that material describing said compound characterized as having one or more of the attributes set forth herein, and typically containing directions for use in accordance with the teachings of this invention. One non-limiting type of written material is a package insert, but brochures and the like represent other types. Written material also includes (but is not limited to) those materials in electronic form.

The packaging can carry such written material by having the written material affixed (releasably or otherwise) to the outside of the container, or provided inside the container itself (e.g., in the case of tableted drug, an insert inside the bottle containing the tablets). Alternatively, if the bottled pharmaceutical is packaged in multiple bottles in shipping containers (e.g., boxes), one or more copies of the written material can be placed in the outer box. If the bottled pharmaceutical is boxed in an individual box, the written material can be inside or on the box.

The Novel cGMP-Specific Phosphodiesterase and PDE2 from Neoplastic Cells

A. In General

One aspect of the pathway involved in this invention is the inhibition of a PDE2 that exhibits a novel conformation and a conventional one, depending on the circumstances. In addition to inhibiting PDE5, pro-apoptotic PDE5 inhibitors inhibit this PDE2-like enzyme, whereas PDE5 inhibitors that do not induce apoptosis have not been found to inhibit this PDE2-like enzyme.

B. The Isolation of the Novel PDE Conformation

In one aspect of the pathway described herein, an isolated cGMP-specific phosphodiesterase (which appears to be a novel conformation of PDE2) was first prepared from the human carcinoma cell line commonly referred to as SW480 available from the American Tissue Type Collection in Rockville, Md., U.S.A. SW480 is a human colon cancer cell line that originated from moderately differentiated epithelial adenocarcinoma. As discussed below, a similar conformation has also been isolated from neoplasias of the breast (i.e., HTB-26 cell line) and prostate (i.e., LNCAP cell line).

By "isolated" we mean (as is understood in the art) not only isolated from neoplastic cells, but also made by recombinant methods (e.g., expressed in a bacterial or other non-human host vector cell lines). However, we presently believe isolation from the human neoplastic cell line is preferable since we believe that the target protein so isolated has a structure (i.e., a conformation or topography) that is closer to, if not identical with, one of the native conformations in the neoplastic cell. This conformation assists in the selection of anti-neoplastic compounds that will inhibit the target enzyme(s) in vivo.

The novel PDE activity was first found in SW480 colon cancer cell lines. To isolate the novel phosphodiesterase from SW480, approximately four hundred million SW480 cells were grown to confluence in and were scraped from 150 cm$^2$ tissue culture dishes after two washes with 10 mL cold PBS and pelleted by centrifugation. The cells were re-suspended in homogenization buffer (20 mL TMPI-EDTA-Triton pH 7.4:20 mM Tris-HOAc, 5 mM MgAc$_2$, 0.1 mM EDTA, 0.8% Triton-100, 10 µM benzamidine, 10 µM TLCK, 2000 U/mL aprotinin, 2 µM leupeptin, 2 µM pepstatin A) and homogenized on an ice bath using a polytron tissumizer (three times, 20 seconds/pulse). The homogenized material was centrifuged at 105,000 g for 60 minutes at 4° C., in a Beckman L8 ultracentrifuge, and the supernatant was diluted with TMPI-EDTA (60 mL) and applied to a 10-milliliter DEAE-Trisacryl M column pre-equilibrated with TMPI-EDTA buffer. The loaded column was washed with 60 mL of TM-EDTA, and PDE activities were eluted with a 120 mL linear gradient of NaOAC (0–0.5 M) in TM-EDTA, at a flow rate of 0.95 mL/minute, 1.4 mL/fraction. Eighty fractions were collected and assayed for cGMP hydrolysis immediately (i.e. within minutes). FIG. 1. shows the column's elution profile, revealing two initial peaks of cGMP PDE activity, Peaks A and B, which were eluted by 40–50 mM and 70–80 mM NaOAC, respectively. As explained below, Peak A is PDE5, whereas Peak B is a novel cGMP-specific phosphodiesterase activity.

Cyclic nucleotide PDE activity of each fraction was determined using the modified two-step radio-isotopic method of Thompson et al. (Thompson W. J., et al., Adv. Cyclic Nucleotide Res. 10: 69–92, 1979), as further described below. The reaction was in 400 µl containing Tris-HCl (40 mM; pH 8.0), MgCl$_2$ (5 mM), 2-mercaptoethanol (4 mM), bovine serum albumin (30 µg), cGMP (0.25 µM–5 µM) with constant tritiated substrate (200,000 cpm). The incubation time was adjusted to give less than 15% hydrolysis. The mixture was incubated at 30° C. followed by boiling for 45 seconds to stop the reaction. Then, the mixture was cooled, snake venom (50 µg) added, and the mixture was incubated at 30° C. for 10 minutes. MeOH (1 mL) was added to stop the reaction, and the mixture was transferred to an anion-exchange column (Dowex 1-X8, 0.25 mL resin). The eluent was combined with a second mL of MeOH, applied to the resin, and after adding 6 mL scintillation fluid, tritium activity was measured using a Beckman LS 6500 for one minute.

Figure 2:
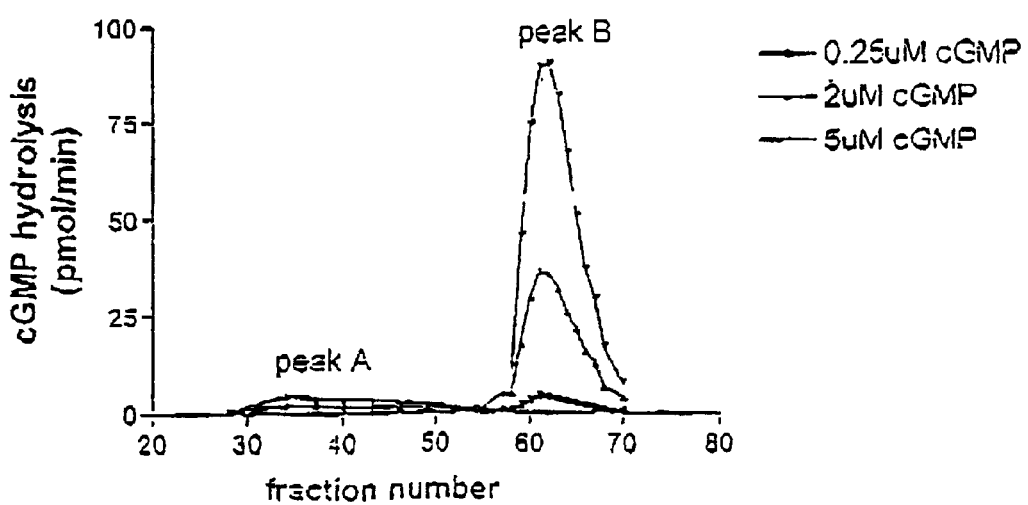
FIG. 2 is a graph of cGMP activities of the reloaded cGMP phosphodiesterases obtained from SW480 neoplastic cells, as assayed from the eluent from a DEAE-Trisacryl M column.

To fractionate the cGMP hydrolytic activities of Peaks A and B further, fractions 15 to 30 of the original 80 were reloaded onto the DEAE-Trisacryl M column and eluted with a linear gradient of NaOAC (0–0.5 M) in TM-EDTA. Fractions were again immediately assayed for cGMP hydrolysis (using the procedure described above with 0.2, 2, 5 µM substrate), the results of which are graphically presented in FIG. 2. One observation about Peak B illustrated in FIG. 2 is that increasing substrate concentration of cGMP dramatically enhanced activity when contrasted to Peak A. While this observation is consistent with its being a PDE2, the fact that the enzyme characterized in FIG. 2 is cGMP-specific (see below) suggests that it has a novel conformation compared to the classic PDE2 reported in the literature. Peak A activity shows apparent substrate saturation of high affinity catalytic sites.

C. The Isolation of Classic PDE2 from SW480

Two methods were found that allowed "Peak B" to be isolated from SW480 so that the enzyme had the classical PDE2 activity (i.e. was not cGMP-specific, but was cGMP stimulated). The first method involved growing the SW480 in 850 cm$^2$ Corning roller bottles instead of 150 cm$^2$ tissue culture flasks. SW480 were grown in roller bottles at 0.5 rpm with each bottle containing 200 mL of RPMI 1640, 2 mM glutamine, and 25 mM HEPES. Cells were harvested by the following procedure.

PBS media was warmed to 37° C. for at least 15 minutes. 200 mL of 5% FBS/RPMI 1640 complete media was prepared and 5 mL of glutamine was added. 5 mL of antibiotic/antimycotic was also added.

70 mL of the PBS solution was added to 10 mL of 4× Pancreatin. The mixture was maintained at room temperature. The media was removed and the flask was rinsed with 4 mL of PBS being sure the bottom of the flask was covered. All solution was removed with a pipet. 4 mL of diluted Pancreatin was added to the flask, and the flask was swished to cover its bottom. The flask was incubated at 37° C. for 8–10 minutes. After the incubation, the flask was quickly checked under an inverted microscope to make sure all cells were rounded. The flask was hit carefully on its side several times to help detach cells. 10 mL of cold complete media was added to the flask to stop the Pancreatin proteolysis. The solution was swirled over the bottom to collect the cells. The media was removed using a 25 mL pipet, and the cells placed in 50 mL centrifuge tubes on ice. The tubes were spun at 1000 rpm at 4° C. for 5 minutes in a clinical centrifuge to pellet cells. The supernatant was poured off and each pellet frozen on liquid nitrogen for 15 seconds. The harvested cells can be stored in a −70° C. freezer.

The PDEs from the harvested SW480 cells were isolated using an FPLC procedure. A Pharmacia AKTA FPLC was used to control sample loading and elution on an 18 mL DEAE TrisAcryl M column. About 600 million cells of SW480 were used for the profiles. After re-suspending cells in homogenization buffer (20 mL TMPI-EDTA-Triton pH 7.4:20 mM Tris-HOAc, 5 mM MgAc$_2$, 0.1 mM EDTA, 0.8% Triton-100, 10 µM benzamidine, 10 µM TLCK, 2000 U/mL aprotinin, 2 µM leupeptin, 2 µM pepstatin A), samples were manually homogenized. FPLC buffer A was 8 mM TRIS-acetate, 5 mM Mg acetate, 0.1 mM EDTA, pH 7.5 and buffer B was 8 mM TRIS-acetate, 5 mM Mg acetate, 0.1 mM EDTA, 1 M Na acetate, pH 7.5. Supernatants were loaded onto the column at 1 mL per minute, followed by a wash with 60 mL buffer A at 1 mL per minute. A gradient was run from 0–15% buffer B in 60 mL, 15–50% buffer B in 60 mL, and 50–100% buffer B in 16 mL. During the gradient, 1.5 mL fractions were collected.

Figure 26:
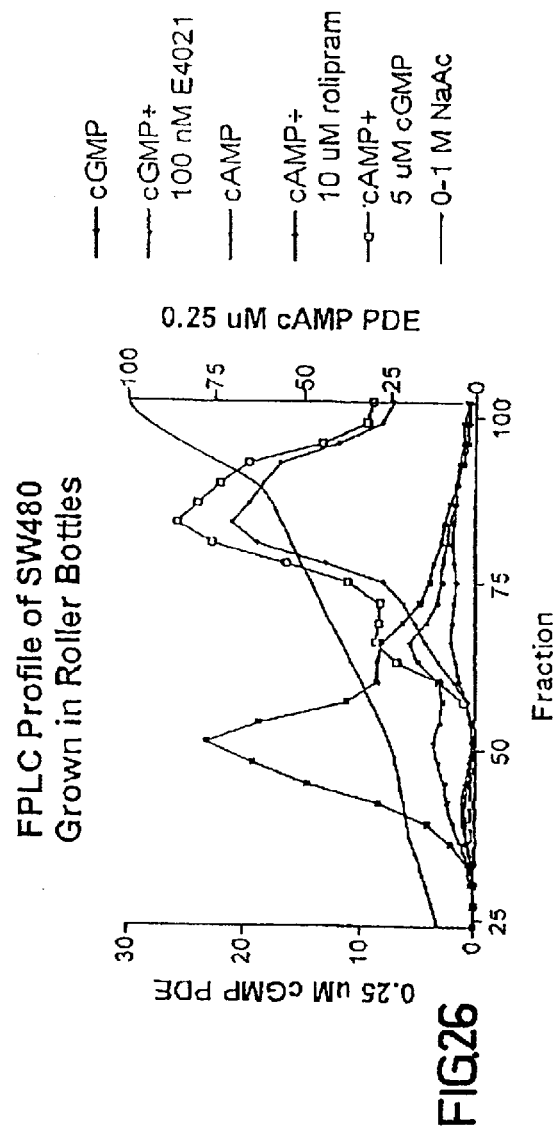
FIG. 26 is a graph of the cGMP hydrolytic activities of the cGMP phosphodiesterases obtained from SW480 neoplastic cells grown in roller bottles, as assayed from the eluent from a DEAE-Trisacryl M column.

The profile obtained was similar (FIG. 26) to the profile for the novel PDE activity (see, e.g., FIG. 1) obtained above, except that Peak B isolated in this manner showed cAMP hydrolytic activity at 0.25 µM substrate that could be activated 2–3 fold by 5 µM cGMP.

Figure 25:
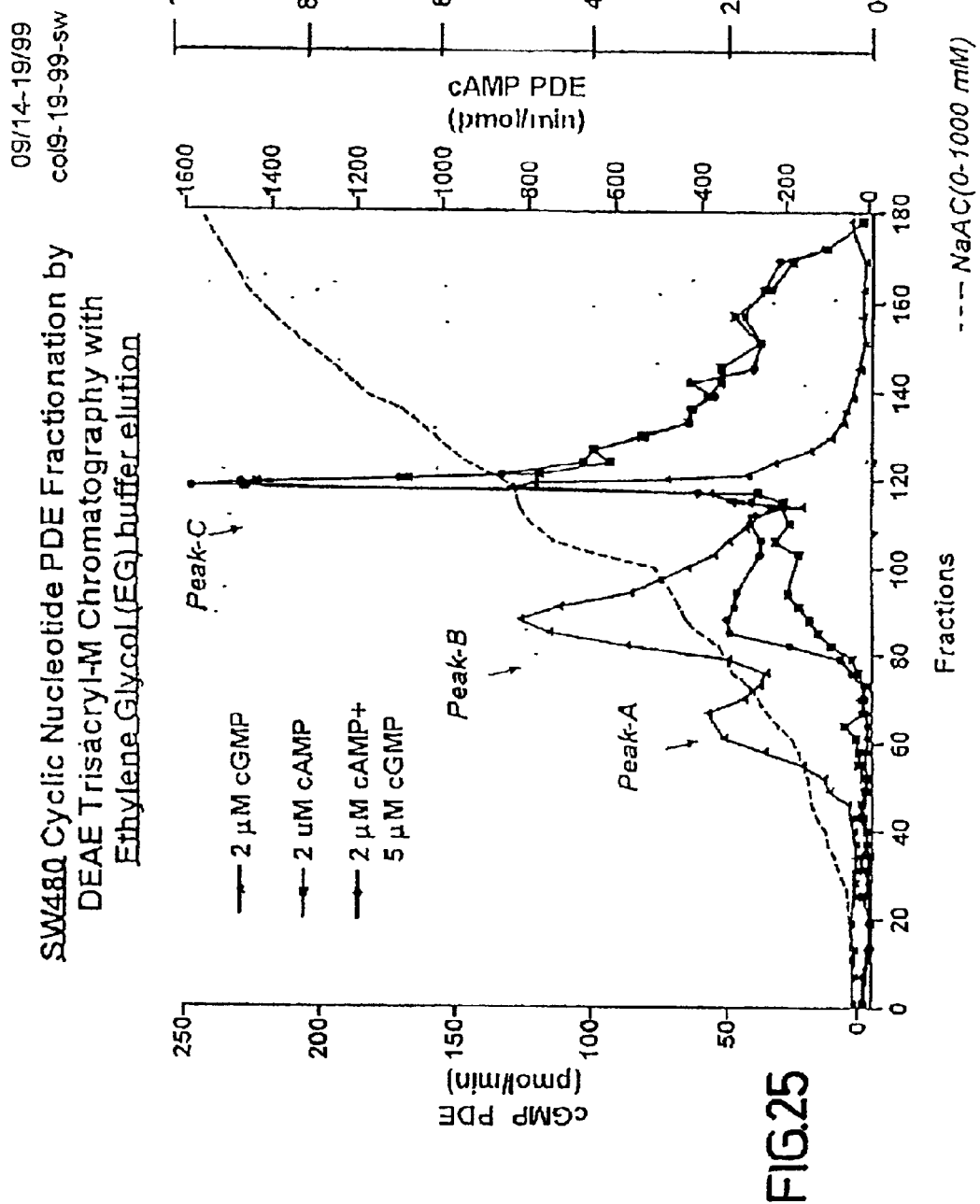
FIG. 25 is a graph of the cGMP hydrolytic activities of the cGMP phosphodiesterases obtained from SW480 neoplastic cells, as assayed from the eluent from a DEAE-Trisacryl M column using ethylene glycol in the buffer.

A second method used to isolate classic PDE2 from SW480 was done using a non-FPLC DEAE column procedure described above (see Section IIB) with the modification that the buffers contained 30% ethylene glycol, 10 mM TLCK and 3.6 mM β-mercaptoethanol. The addition of these reagents to the buffers causes a shift in the elution profile (see FIG. 25) from low to high sodium acetate so that Peak A moves from 40 to 150 mM, Peak B from 75 to 280 mM and Peak C from 200 to 500 mM Na acetate (see FIG. 25). Peak B in FIG. 25 was assayed with 2 µM cAMP substrate and showed a two-fold activation by 5 µM cGMP (see FIG. 26). The selective PDE2 inhibitor EHNA inhibited 2 µM cGMP PDE activity in this Peak B with an IC$_{50}$ of 1.6 µM and inhibited 2.0 µM cAMP PDE activity in Peak B with an IC$_{50}$ of 3.8 µM (and IC$_{50}$ of 2.5 µM with addition of 10 µM rolipram).

D. cGMP-Specificity of PDE Peak A and the Novel Peak B Activity

Each fraction from the DEAE column from Section IIB was also assayed for cGMP-hydrolysis activity (0.25 µM cGMP) in the presence or absence of Ca$^{++}$, or Ca$^{++}$-CaM and/or EGTA and for cAMP (0.25 µM cAMP) hydrolysis activity in the presence or absence of 5 µM cGMP. Neither PDE Peak A and Peak B (fractions 5–22; see FIG. 1) hydrolyzed cAMP significantly, establishing that neither had the activity of a classic cAMP-hydrolyzing family of PDE (i.e. a PDE 1, 2, 3).

$Ca^{++}$ (with or without calmodulin) failed to activate either cAMP or cGMP hydrolysis activity of either Peak A or B, and cGMP failed to activate or inhibit cAMP hydrolysis. Such results establish that Peaks A and B constitute cGMP-specific PDE activities but not classic or previously known PDE1, PDE2, PDE3 or PDE4 activities.

For the novel PDE Peak B, as discussed below, cyclic GMP activated the cGMP hydrolytic activity of the enzyme, but did not activate any cAMP hydrolytic activity (in contrast with the Peak B from Section IIC above). This reveals that the novel PDE Peak B—the novel phosphodiesterase of this invention—is not a cGMP-stimulated cAMP hydrolysis ("cGS") or among the classic or previously known PDE2 family activities because the known isoforms of PDE2 hydrolyze both cGMP and cAMP.

E. Peak A is a Classic PDE5, but the Novel Peak B—a New cGMP-Specific PDE—is Not To characterize any PDE isoform, kinetic behavior and substrate preference should be assessed.

Peak A showed typical "PDE5" characteristics. For example, the $K_m$ of the enzyme for cGMP was 1.07 $\mu$M, and Vmax was 0.16 nmol/min/mg. In addition, as discussed below, zaprinast ($IC_{50}$=1.37 $\mu$M) and E4021 ($IC_{50}$=3 nM) and sildenafil inhibited activity of Peak A. Further, zaprinast showed inhibition for cGMP hydrolysis activity of Peak A, consistent with results reported in the literature.

Figure 3:
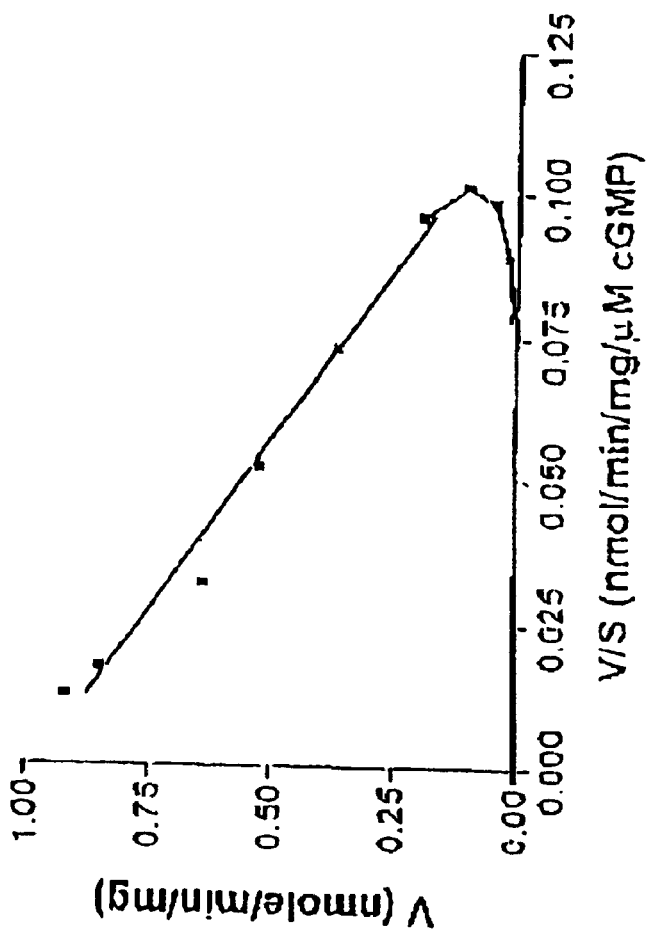
FIG. 3 is a graph of the kinetic behavior of the novel PDE of this invention.

PDE Peak B from Section IIB showed considerably different kinetic properties as compared to PDE Peak A. For example, in Eadie-Hofstee plots of Peak A, cyclic GMP hydrolysis shows single line with negative slope with increasing substrate concentrations, indicative of Michaelis-Menten kinetic behavior. Peak B, however, shows the novel property for cGMP hydrolysis in the absence of cAMP of a decreasing (apparent $K_m$=8.4), then increasing slope ($K_m$<1) of Eadie-Hofstee plots with increasing cGMP substrate (see, FIG. 3). Thus, this establishes Peak B's submicromolar affinity for cGMP (i.e., where $K_m$<1).

Consistent with the kinetic studies (i.e., FIG. 3) and positive-cooperative kinetic behavior in the presence of cGMP substrate, was the increased cGMP hydrolytic activity in the presence of increasing concentrations of cGMP substrate. This was discovered by comparing 0.25 $\mu$M, 2 $\mu$M and 5 $\mu$M concentrations of cGMP in the presence of PDE Peak B after a second DEAE separation to rule out cAMP hydrolysis and to rule out this new enzyme being a previously identified PDE5. Higher cGMP concentrations evoked disproportionately greater cGMP hydrolysis with PDE Peak B, as shown in FIG. 2.

These observations suggest that cGMP binding to the Peak B enzyme causes a conformational change in the enzyme. This confirms the advantage of using the native enzyme from neoplastic cells, but this invention is not limited to the native form of the enzyme having the characteristics set forth above.

F. Zaprinast- and Sildenafil-Insensitivity of PDE Peak B Relative to Peak A, and Their Effects on Other PDE Inhibitors Different PDE inhibitors were studied using twelve concentrations of drug from 0.01 to 100 $\mu$M and substrate concentration of 0.25 $\mu$M $^3$H-cGMP. $IC_{50}$ values were calculated with variable slope, sigmoidal curve fits using Prism 2.01 (GraphPad). The results are shown in Table 1. While compounds E4021 and zaprinast inhibited Peak A (with high affinities), $IC_{50}$ values calculated against the novel PDE activity in Peak B (Section IIB) are significantly increased (>50 fold). This confirms that Peak A is a PDE5. These data further illustrate that the novel PDE activity of this invention is, for all practical purposes, zaprinast-insensitive and E4021-insensitive.

TABLE 1

Comparison of PDE Inhibitors Against Peak A and Section IA Peak B (cGMP Hydrolysis)

| Compound | PDE Family Inhibitor | $IC_{50}$ Peak A ($\mu$M) | $IC_{50}$ Peak B ($\mu$M) | Ratio ($IC_{50}$ Peak A/Peak B) |
|---|---|---|---|---|
| E4021 | 5 | 0.003 | 8.4 | 0.0004 |
| Zaprinast | 5 | 1.4 | >30 | <0.05 |
| Compound E | 5 and others | 0.38 | 0.37 | 1.0 |
| Sulindac sulfide | 5 and others | 50 | 50 | 1.0 |
| Vinpocetine | 1 | >100 | >100 | |
| EHNA | 2 | >100 | 3.7 | |
| Indolidan | 3 | 31 | >100 | <0.31 |
| Rolipram | 4 | >100 | >100 | |
| Sildenafil | 5 | .0003 | >10 | <.00003 |

By contrast, sulindac sulfide and Compound E competitively inhibited both Peaks A and B phosphodiesterases at the same potency ($IC_{50}$=0.38 $\mu$M for PDE Peak A; 0.37 $\mu$M for PDE Peak B).

There is significance for the treatment of neoplasia and the selection of useful compounds for such treatment in the fact that Peak B (either form of it) is zaprinast-insensitive whereas Peaks A and B are both sensitive to sulindac sulfide and Compound E. We have tested zaprinast, E4021 and sildenafil to ascertain whether they induce apoptosis or inhibit the growth of neoplastic cells, and have done the same for Compound E. As explained below, zaprinast by itself does not have significant apoptosis-inducing or growth-inhibiting properties, whereas sulindac sulfide and Compound E are precisely the opposite. In other words, the ability of a compound to inhibit both PDE Peaks A and B correlates with its ability to induce apoptosis in neoplastic cells, whereas if a compound (e.g., zaprinast) has specificity for PDE Peak A only, that compound will not by itself induce apoptosis.

G. Insensitivity of the Novel PDE Peak B to Incubation with cGMP-Dependent Protein Kinase G Further differences between PDE Peak A and the novel Peak B (Section IIB) were observed in their respective cGMP-hydrolytic activities in the presence of varying concentrations of cGMP-dependent protein kinase G (which phosphorylates typical PDE5). Specifically, Peak A and Peak B fractions from Section IIB were incubated with different concentrations of protein kinase G at 30° C. for 30 minutes. Cyclic GMP hydrolysis of both peaks has assayed after phosphorylation was attempted. Consistent with previously published information about PDE5, Peak A showed increasing cGMP hydrolysis activity in response to protein kinase G incubation, indicating that Peak A was phosphorylated. Peak B was unchanged, however (i.e., was not phosphorylated and insensitive to incubation with cGMP-dependent protein kinase G). These data are consistent with Peak A being an isoform consistent with the known PDE5 family and Peak B from Section IIB being a novel cGMP-specific PDE activity.

H. Novel Peak B in Prostate and Breast Cancer Cell Lines

Figure 20:
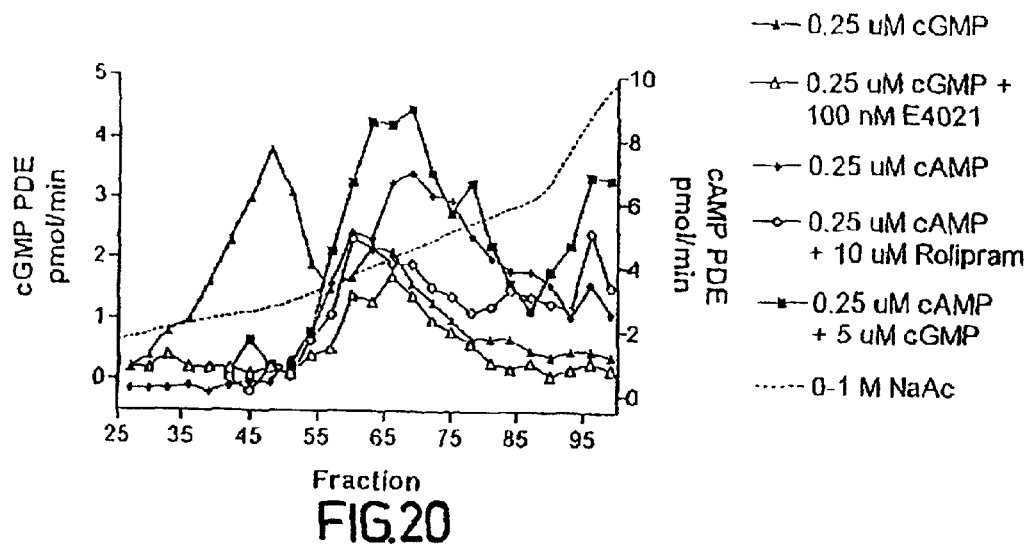
FIG. 20 is a graph of the cGMP hydrolytic activities of the cGMP phosphodiesterases obtained from HTB-26 neoplastic cells, as assayed from the eluent from a DEAE-Trisacryl M column.
Figure 21:
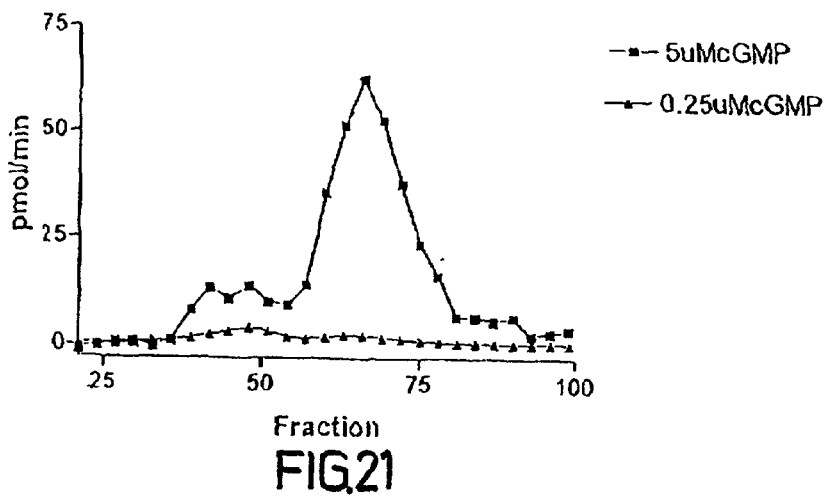
FIG. 21 is a graph of the cGMP hydrolytic activities of the cGMP phosphodiesterases obtained from HTB-26 neoplastic cells, as assayed from the eluent from a DEAE-Trisacryl M column with low and high substrate concentration.
Figure 22:
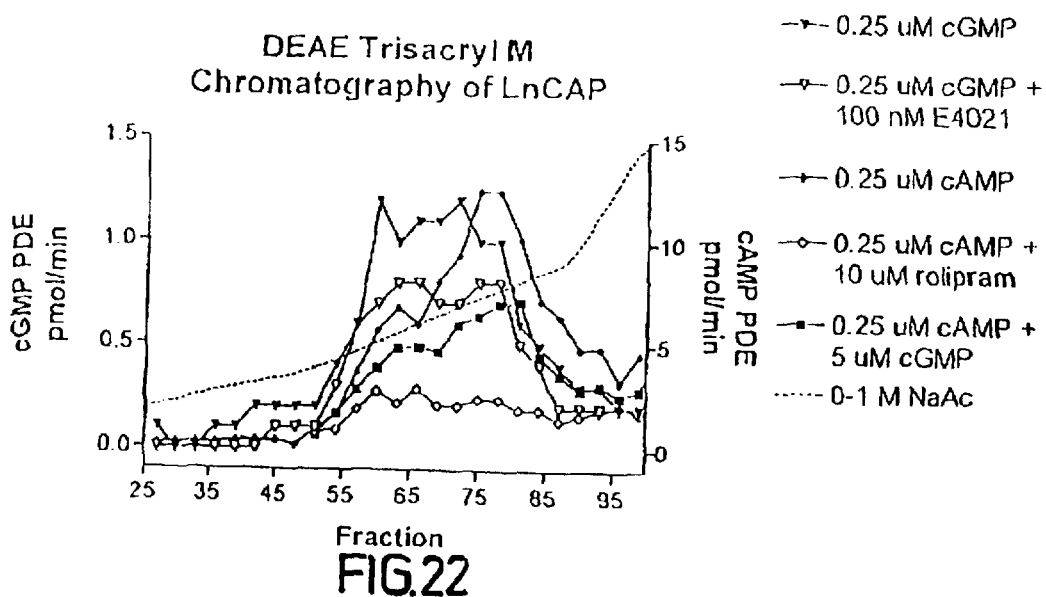
FIG. 22 is a graph of the cGMP hydrolytic activities of the cGMP phosphodiesterases obtained from LnCAP neoplastic cells, as assayed from the eluent from a DEAE-Trisacryl M column.
Figure 23:
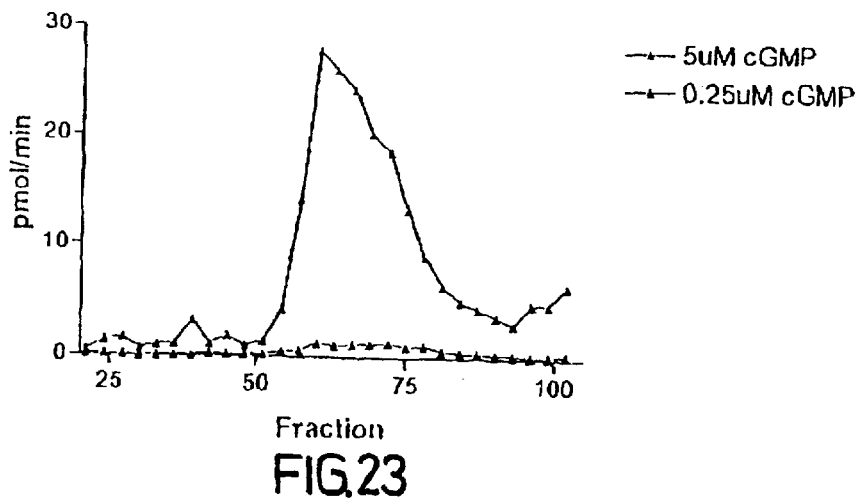
FIG. 23 is a graph of the cGMP hydrolytic activities of the cGMP phosphodiesterases obtained from LnCAP neoplastic cells, as assayed from the eluent from a DEAE-Trisacryl M column with low and high substrate concentration.

The novel Peak B was also isolated from two other neoplastic cell lines, a breast cancer cell line, HTB-26, and a prostate cancer cell line, LnCAP, by a procedure similar to the one above used to isolate it from SW480. The protocol was modified in several respects. To provide even greater reproducibility to allow comparison of different cell lines, a Pharmacia AKTA FPLC was used to control sample loading and elution on an 18 mL DEAE TrisAcryl M column. SW840 was run by this same procedure multiple times to provide a reference of Peak B. 200–400 million cells of SW480 were used for the profiles. 70 million cells of LnCAP were used for a profile (see FIGS. 22 and 23), and in a separate experiment 32 million cells of HTB-26 were used for a profile (see FIGS. 20 and 21). After re-suspending cells in homogenization buffer, samples were manually homogenized. FPLC buffer A was 8 mM TRIS-acetate, 5 mM Mg acetate, 0.1 mM EDTA, pH 7.5 and buffer B was 8 mM TRIS-acetate, 5 mM Mg acetate, 0.1 mM EDTA, 1 M Na acetate, pH 7.5. Supernatants were loaded onto the column at 1 mL per minute, followed by a wash with 60 mL buffer A at 1 mL per minute. A gradient was run from 0–15% buffer B in 60 mL, 15–50% buffer B in 60 mL, and 50–100% buffer B in 16 mL. During the gradient 1.5 mL fractions were collected. Peaks of cGMP PDE activity eluted around fraction 65 that was at 400 mM Na acetate (see FIGS. 20–23). This activity was measured at 0.25 $\mu$M cGMP (indicating submicromolar affinity for cGMP). Rolipram, a PDE4-specific drug, inhibited most of the cAMP PDE activity (i.e. the cAMP activity was due to PDE4), indicating that the Peak B's cGMP activity was specific for cGMP over cAMP. None of the three Peak B's (from SW480, HTB-26, and LnCAP) showed stimulation with calcium/calmodulin and all were resistant to 100 nM E4021, a specific PDE5-specific inhibitor like zaprinast (see FIGS. 20 and 22). The Peak B's also showed a dramatic increase in activity when substrate was increased from 0.25 $\mu$M to 5 $\mu$M cGMP (suggesting positively cooperative kinetics) (see FIGS. 21 and 23). Also, the three peaks show similar inhibition by exisulind and Compound I, below.

Protein Kinase G and $\beta$-Catenin Involvement—in General

A series of experiments were performed to ascertain what effect, if any, an anti-neoplastic cGMP-specific PDE inhibitor such as exisulind had on cGMP-dependent protein kinase G ("PKG") in neoplastic cells containing either the adenomatous polyposis coli gene ("APC gene") defect or a defect in the gene coding for $\beta$-catenin. As explained below, such an inhibitor causes an elevation in PKG activity in such neoplastic cells. That increase in activity was not only due to increased activation of PKG in cells containing either defect, but also to increased expression of PKG in cells containing the APC defect. In addition, when PKG from neoplastic cells with either defect is immunoprecipitated, it precipitates with $\beta$-catenin.

$\beta$-catenin has been implicated in a variety of different cancers because researchers have found high levels of it in patients with neoplasias containing mutations in the APC tumor-suppressing gene. People with mutations in this gene at birth often develop thousands of small tumors in the lining of their colon. When it functions properly, the APC gene codes for a normal APC protein that is believed to bind to and regulate $\beta$-catenin. Thus, the discovery that PKG in neoplastic cells containing either the APC gene defect or the $\beta$-catenin defect is bound to $\beta$-catenin indeed strongly implicates PKG in one of the major cellular pathways that leads to cancer. In addition, the relationship between cGMP-specific inhibition and PKG elevation upon treatment with SAANDs links cGMP to the PKG/$\beta$-catenin/APC defect in such cells.

This latter link is further buttressed by the observation that $\beta$-catenin itself is reduced when neoplastic cells containing the APC defect or the $\beta$-catenin defect are exposed to a SAAND. This reduction in $\beta$-catenin is initiated by PKG itself. PKG phosphorylates $\beta$-catenin—which is another novel observation associated with this invention. The phosphorylation of $\beta$-catenin allows $\beta$-catenin to be degraded by ubiquitin-proteasomal system.

This phosphorylation of $\beta$-catenin by PKG is important in neoplastic cells because it circumvents the effect of the APC and $\beta$-catenin mutations. The mutated APC protein affects the binding of the $\beta$-catenin bound to the mutant APC protein, which change in binding has heretofore been thought to prevent the phosphorylation of $\beta$-catenin by GSK-3b kinase. In the case of mutant $\beta$-catenin, an elevation of PKG activity also allows the mutant $\beta$-catenin to be phosphorylated. Elevating PKG activity in neoplasia with cGMP-PDE inhibition allows for $\beta$-catenin phosphorylation (leading to its degradation) in neoplastic cells containing either type of mutation.

In short, these findings not only lead to new pharmaceutical screening methods to identify further SAAND candidate compounds, but also buttress the role of cGMP-specific PDE inhibition in therapeutic approaches to neoplasia. This observation may also explain the unexpectedly broad range of neoplasias SAANDs can inhibit since both neoplasia with and without the APC defect can be treated, as explained above.

IV. Screening Pharmaceutical Compositions using the PDES
  A. In General

The novel PDE of this invention and PDE2 are useful with or without PDE5 to identify compounds that can be used to treat or prevent neoplasias, and that are not characterized by serious side effects.

Cancer and precancer may be thought of as diseases that involve unregulated cell growth. Cell growth involves a number of different factors. One factor is how rapidly cells proliferate, and another involves how rapidly cells die. Cells can die either by necrosis or apoptosis depending on the type of environmental stimuli. Cell differentiation is yet another factor that influences tumor growth kinetics. Resolving which of the many aspects of cell growth is affected by a compound is important to the discovery of a relevant target for pharmaceutical therapy. Screening assays based on this technology can be combined with other tests to select compounds that have growth inhibiting and pro-apoptotic activity.

This invention is the product of several important discoveries. First, the present inventors discovered that desirable inhibitors of tumor cell growth induce premature death of cancer cells by apoptosis (see, Piazza, G. A., et al., *Cancer Research*, 55(14), 3110–16, 1995). Second, several of the present inventors unexpectedly discovered compounds that selectively induce apoptosis without substantial COX inhibition also inhibit PDE5. In particular, and contrary to leading scientific studies, desirable compounds for treating neoplastic lesions inhibit PDE5 (EC 3.1.4.17). PDE5 is one of at least ten gene families of phosphodiesterase. PDE5 and the novel PDE of this invention are unique in that they selectively degrade cyclic GMP and not cAMP, while the other families of PDE selectively degrade/hydrolyze cAMP and not cGMP or non-selectively degrade both cGMP and cAMP. Preferably, desirable compounds used to treat neoplasia do not substantially inhibit non-selective or cAMP degrading phosphodiesterase types.

B. COX Screening

A preferred embodiment of the present invention involves determining the cyclooxygenase inhibition activity of a given compound, and determining the cGMP specific PDE inhibitory activity of the compound. The test compounds are assessed for their ability to treat neoplastic lesions either directly or indirectly by comparing their activities against known compounds useful for treating neoplastic lesions. A standard compound that is known to be effective for treating neoplastic lesions without causing gastric irritation is 5-fluoro-2-methyl-1-(p-methylsulfonylbenzylidene)-3-indenylacetic acid ("exisulind"). Other useful compounds for comparative purposes include those that are known to inhibit COX, such as indomethacin and the sulfide metabolite of sulindac: 5-fluoro-2-methyl-1-(p-methylsulfinylbenzylidene)-3-indenylacetic acid ("sulindac sulfide"). Other useful compounds for comparative purposes include those that are known to inhibit cGMP-specific PDEs, such as 1-(3-chloroanilino)-4-phenyphthalazine ("MY5445").

As used herein, the term "precancerous lesion" includes syndromes represented by abnormal neoplastic, including dysplastic, changes of tissue. Examples include dysplastic growths in colonic, breast, prostate or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, lung, prostatic dysplasia, prostatic intraneoplasia, breast and/or skin and related conditions (e.g., actinic keratosis), whether the lesions are clinically identifiable or not.

As used herein, the terms "carcinoma" or "cancer" refers to lesions which are cancerous. Examples include malignant melanomas, breast cancer, prostate cancer and colon cancer. As used herein, the terms "neoplasia" and "neoplasms" refer to both cancerous and pre-cancerous lesions.

As used herein, the abbreviation PG represents prostaglandin; PS represents prostaglandin synthetase; $PGE_2$ represents prostaglandin $E_2$; PDE represents phosphodiesterase; COX represents cyclooxygenase; cyclic nucleotide, RIA represents—radioimmunoassay.

COX inhibition by a compound can be determined by either of two methods. One method involves measuring $PGE_2$ secretion by intact HL-60 cells following exposure to the compound being screened. The other method involves measuring the activity of purified cyclooxygenases (COXs) in the presence of the compound. Both methods involve protocols previously described in the literature, but preferred protocols are set forth below.

Compounds can be evaluated to determine whether they inhibit the production of prostaglandin $E_2$ ("$PGE_2$"), by measuring $PGE_2$. Using an enzyme immunoassay (EIA) kit for $PGE_2$, such as commercially available from Amersham, Arlington Heights, Ill. U.S.A. Suitable cells include those that make an abundance of PG, such as HL-60 cells. HL-60 cells are human promyelocytes that are differentiated with DMSO into mature granulocytes (see, Collins, S. J., Ruscetti, F. W., Gallagher, R. E. and Gallo, R. C., "Normal Functional Characteristics of Cultured Human Promyelocytic Leukemia Cells (HL-60) After Induction of Differentiation By Dimethylsulfoxide", *J. Exp. Med.*, 149:969–974, 1979). These differentiated cells produce $PGE_2$ after stimulation with a calcium ionophore, A23187 (see, Kargman, S., Prasit, P. and Evans, J. F., "Translocation of HL-60 Cell 5-Lipoxygenase", *J. Biol. Chem.*, 266: 23745–23752, 1991). HL-60 cells are available from the ATCC (ATCC:CCL240). They can be grown in a RPMI 1640 medium supplemented with 20% heat-inactivated fetal bovine serum, 50 U/mL penicillin and 50 μg/mL streptomycin in an atmosphere of 5% $CO_2$ at 37° C. To induce myeloid differentiation, cells are exposed to 1.3% DMSO for 9 days and then washed and resuspended in Dulbecco's phosphate-buffered saline at a concentration of $3\times10^6$ cells/mL.

The differentiated HL-60 cells ($3\times10^6$ cells/mL) are incubated for 15 minutes at 37° C. in the presence of the compounds tested at the desired concentration. Cells are then stimulated by A23187 ($5\times10^{-6}$ M) for 15 minutes. $PGE_2$ secreted into the external medium is measured as described above.

As indicated above, a second method to assess COX inhibition of a compound is to measure the COX activity in the presence of a test compound. Two different forms of cyclooxygenase (COX-I and COX-2) have been reported in the literature to regulate prostaglandin synthesis. COX-2 represents the inducible form of COX while COX-I represents a constitutive form. COX-I activity can be measured using the method described by Mitchell et al. ("Selectivity of Nonsteroidal Anti-inflammatory Drugs as Inhibitors of Constitutive and Inducible Cyclooxygenase," *Proc. Natl. Acad. Sci. USA.*, 90:11693–11697, 1993, which is incorporated herein by reference) using COX-I purified from ram seminal vesicles as described by Boopathy & Balasubramanian, "Purification And Characterization Of Sheep Platelet Cyclooxygenase" (*Biochem. J.*, 239:371–377, 1988, which is incorporated herein by reference). COX-2 activity can be measured using COX-2 purified from sheep placenta as described by Mitchell et al., 1993, supra.

The cyclooxygenase inhibitory activity of a drug can be determined by methods known in the art. For example, Boopathy & Balasubramanian, 1988, supra, described a procedure in which prostaglandin H synthase 1 (Cayman Chemical, Ann Arbor, Mich.) is incubated at 37° C. for 20 minutes with 100 μM arachidonic acid (Sigma Chemical Co.), cofactors (such as 1.0 mM glutathione, 1.0 mM hydroquinone, 0.625 μM hemoglobin and 1.25 mM $CaCl_2$ in 100 mM Tris-HCl, pH 7.4) and the drug to be tested. Following incubation, the reaction can be terminated with trichloroacetic acid. After stopping the reaction by adding thiobarbituric acid and malonaldehyde, enzymatic activity can then be measured spectrophotometrically at 530 nm.

Obviously, a compound that exhibits a lower COX-I or COX-2 inhibitory activity in relation to its greater combined PDE5/novel PDE/PDE2 inhibitory activities may be a desirable compound.

The amount of COX inhibition is determined by comparing the activity of the cyclooxygenase in the presence and absence of the test compound. Residual (i.e., less than about 25%) or no COX inhibitory activity at a concentration of about 100 μM is indicative that the compound should be evaluated further for usefulness for treating neoplasia.

C. Determining Phosphodiesterase Inhibition Activity

Compounds can be screened for inhibitory effect on the activity of the novel phosphodiesterase of this invention using either the enzyme isolated as described above, a recombinant version, or using the novel PDE and/or PDE2 together with PDE5. Alternatively, cyclic nucleotide levels in whole cells are measured by RIA and compared to untreated and zaprinast-treated cells.

Phosphodiesterase activity can be determined using methods known in the art, such as a method using radioactive $^3$H cyclic GMP (cGMP)(cyclic 3',5'-guanosine monophosphate) as the substrate for the PDE enzyme. (Thompson, W. J., Teraski, W. L., Epstein, P. M., Strada, S. J., *Advances in Cyclic Nucleotide Research*, 10:69–92, 1979, which is incorporated herein by reference). In brief, a solution of defined substrate $^3$H-cGMP specific activity (0.2 μM; 100,000 cpm;

containing 40 mM Tris-HCl (pH 8.0), 5 mM $MgCl_2$ and 1 mg/mL BSA) is mixed with the drug to be tested in a total volume of 400 µl. The mixture is incubated at 30° C. for 10 minutes with isolated PDE of this invention. Reactions are terminated, for example, by boiling the reaction mixture for 75 seconds. After cooling on ice, 100 µl of 0.5 mg/mL snake venom (*O. Hannah* venom available from Sigma) is added and incubated for 10 minutes at 30° C. This reaction is then terminated by the addition of an alcohol, e.g. 1 mL of 100% methanol. Assay samples are applied to 1 mL Dowex 1-X8 column; and washed with 1 mL of 100% methanol. The amount of radioactivity in the breakthrough and the wash from the column is combined and measured with a scintillation counter. The degree of phosphodiesterase inhibition is determined by calculating the amount of radioactivity in drug-treated reactions and comparing against a control sample (a reaction mixture lacking the tested compound but with drug solvent).

Alternatively, the ability of desirable compounds to inhibit the phosphodiesterases of this invention is reflected by an increase in cGMP in neoplastic cells exposed to a compound being screened. The amount of PDE activity can be determined by assaying for the amount of cyclic GMP in the extract of treated cells using radioimmunoassay (RIA). In this procedure, HT-29 or SW-480 cells are plated and grown to confluency. As indicated above, SW-480 contains both PDE5 and the novel PDE of this invention, so when PDE activity is evaluated in this fashion, a combined cGMP hydrolytic activity is assayed simultaneously. The test compound is then incubated with the cell culture at a concentration of compound between about 200 µM to about 200 pM. About 24 to 48 hours thereafter, the culture media is removed from the cells, and the cells are solubilized. The reaction is stopped by using 0.2N HCl/50% MeOH. A sample is removed for protein assay. Cyclic GMP is purified from the acid/alcohol extracts of cells using anion-exchange chromatography, such as a Dowex column. The cGMP is dried, acetylated according to published procedures, such as using acetic anhydride in triethylamine, (Steiner, A. L., Parker, C. W., Kipnis, D. M., *J. Biol. Chem.*, 247(4) :1106–13, 1971, which is incorporated herein by reference). The acetylated cGMP is quantitated using radioimmunoassay procedures (Harper, J., Brooker, G., *Advances in Nucleotide Research*, 10:1–33, 1979, which is incorporated herein by reference). Iodinated ligands (tyrosine methyl ester) of derivatized cyclic GMP are incubated with standards or unknowns in the presence of antisera and appropriate buffers. Antiserum may be produced using cyclic nucleotide-haptene directed techniques. The antiserum is from sheep injected with succinyl-cGMP-albumin conjugates and diluted 1/20,000. Dose-interpolation and error analysis from standard curves are applied as described previously (Seibert, A. F., Thompson, W. J., Taylor, A., Wilbourn, W. H., Barnard, J. and Haynes, J., *J. Applied Physiol.*, 72:389–395, 1992, which is incorporated herein by reference).

In addition, the culture media may be acidified, frozen (−70° C.) and also analyzed for cGMP and cAMP.

In addition to observing increases in the content of cGMP in neoplastic cells caused by desirable compounds, decreases in content of cAMP have also been observed. It has been observed that a particularly desirable compound (i.e., one that selectively induces apoptosis in neoplastic cells, but not substantially in normal cells) follows a time course consistent with cGMP-specific PDE inhibition as one initial action resulting in an increased cGMP content within minutes. Secondarily, treatment of neoplastic cells with a desirable anti-neoplastic compound leads to decreased cAMP content within 24 hours. The intracellular targets of drug actions are being studied further, but current data support the concept that the initial rise in cGMP content and the subsequent fall in cAMP content precede apoptosis in neoplastic cells exposed to desirable compounds.

The change in the ratio of the two cyclic nucleotides may be a more accurate tool for evaluating desirable cGMP-specific phosphodiesterase inhibition activity of test compounds, rather than measuring only the absolute value of cGMP, only cGMP-specific phosphodiesterase inhibition, or only the level of cGMP hydrolysis. In neoplastic cells not treated with anti-neoplastic compounds, the ratio of cGMP content/cAMP content is in the 0.03–0.05 range (i.e., 300–500 fmol/mg protein cGMP content over 6000–8000 fmol/mg protein cAMP content). After exposure to desirable anti-neoplastic compounds, that ratio increases several fold (preferably at least about a three-fold increase) as the result of an initial increase in cyclic GMP and the later decrease in cyclic AMP.

Specifically, it has been observed that particularly desirable compounds achieve an initial increase in cGMP content in treated neoplastic cells to a level of cGMP greater than about 500 fmol/mg protein. In addition, particularly desirable compounds cause the later decrease in cAMP content in treated neoplastic cells to a level of cAMP less than about 4000 fmol/mg protein.

To determine the content of cyclic AMP, radioimmunoassay techniques similar to those described above for cGMP are used. Basically, cyclic nucleotides are purified from acid/alcohol extracts of cells using anion-exchange chromatography, dried, acetylated according to published procedures and quantitated using radioimmunoassay procedures. Iodinated ligands of derivatized cyclic AMP and cyclic GMP are incubated with standards or unknowns in the presence of specific antisera and appropriate buffers.

Verification of the cyclic nucleotide content may be obtained by determining the turnover or accumulation of cyclic nucleotides in intact cells. To measure intact cell cAMP, $^3$H-adenine pre-labeling is used according to published procedures (Whalin, M. E., Garrett Jr., R. L., Thompson, W. J., and Strada, S. J. "Correlation of cell-free brain cyclic nucleotide phosphodiesterase activities to cyclic AMP decay in intact brain slices", *Sec. Mess. and Phos. Protein Research*, 12:311–325, 1989, which is incorporated herein by reference). The procedure measures flux of labeled ATP to cyclic AMP and can be used to estimate intact cell adenylate cyclase or cyclic nucleotide phosphodiesterase activities depending upon the specific protocol. Cyclic GMP accumulation was too low to be studied with intact cell pre-labeling according to published procedures (Reynolds, P. E., S. J. Strada and W. J. Thompson, "Cyclic GMP Accumulation In Pulmonary Microvascular Endothelial Cells Measured By Intact Cell Prelabeling," *Life Sci.*, 60:909–918, 1997, which is incorporated herein by reference).

The PDE inhibitory activity effect of a compound can also be determined from a tissue sample. Tissue biopsies from humans or tissues from anesthetized animals are collected from subjects exposed to the test compound. Briefly, a sample of tissue is homogenized in 500 µl of 6% TCA. A known amount of the homogenate is removed for protein analysis. The remaining homogenate is allowed to sit on ice for 20 minutes to allow for the protein to precipitate. Next, the homogenate is centrifuged for 30 minutes at 15,000 g at 4° C. The supernatant is recovered, and the pellet recovered. The supernatant is washed four times with five volumes of water saturated diethyl ether. The upper ether layer is discarded between each wash. The aqueous ether extract is dried in a speed vac. Once dried, the sample can be frozen for future use, or used immediately. The dried extract is dissolved in 500 µl of assay buffer. The amount of cGMP-specific inhibition is determined by assaying for the amount of cyclic nucleotides using RIA procedures as described above.

The amount of inhibition is determined by comparing the activity of the novel PDE (or PDE2) in the presence and absence of the compound. Inhibition of the novel PDE activity (or PDE2) is indicative that the compound is useful for treating neoplasia. Significant inhibitory activity greater than that of the benchmark, exisulind, preferably greater than 50% at a concentration of 10 µM or below, is indicative that a compound should be further evaluated for antineoplastic properties. Preferably, the $IC_{50}$ value for the novel PDE inhibition should be less than 50 µM for the compound to be further considered for potential use.

D. Determining Whether a Compound Reduces Tumor Cell Growth

In an alternate embodiment, the method of the present invention involves further determining whether the compound reduces the growth of tumor cells. Various cell lines can be used in the sample depending on the tissue to be tested. For example, these cell lines include: SW-480—colonic adenocarcinoma; HT-29—colonic adenocarcinoma, A-427—lung adenocarcinoma carcinoma; MCF-7—breast adenocarcinoma; and UACC-375—melanoma line; and DU145—prostrate carcinoma. Cytotoxicity data obtained using these cell lines are indicative of an inhibitory effect on neoplastic lesions. These cell lines are well characterized, and are used by the United States National Cancer Institute in their screening program for new anti-cancer drugs.

A compound's ability to inhibit tumor cell growth can be measured using the HT-29 human colon carcinoma cell line obtained from ATCC. HT-29 cells have previously been characterized as a relevant colon tumor cell culture model (Fogh, J., and Trempe, G. In: Human Tumor Cells in Vitro, J. Fogh (eds.), Plenum Press, New York, pp. 115–159, 1975). HT-29 cells are maintained in RPMI media supplemented with 5% fetal bovine calf serum (Gemini Bioproducts, Inc., Carlsbad, Calif.) and 2 mm glutamine, and 1% antibiotic-antimycotic in a humidified atmosphere of 95% air and 5% $CO_2$ at 37° C. Briefly, HT-29 cells are plated at a density of 500 cells/well in 96 well microtiter plates and incubated for 24 hours at 37° C. prior to the addition of compound. Each determination of cell number involved six replicates. After six days in culture, the cells are fixed by the addition of cold trichloroacetic acid to a final concentration of 10% and protein levels are measured using the sulforhodamine B (SRB) colorimetric protein stain assay as previously described by Skehan, P., Storeng, R., Scudiero, D., Monks, A., McMahon, J., Vistica, D., Warren, J. T., Bokesch, H., Kenney, S., and Boyd, M. R., "New Colorimetric Assay For Anticancer-Drug Screening," J. Natl. Cancer Inst. 82: 1107–1112, 1990, which is incorporated herein by reference.

In addition to the SRB assay, a number of other methods are available to measure growth inhibition and could be substituted for the SRB assay. These methods include counting viable cells following trypan blue staining, labeling cells capable of DNA synthesis with BrdU or radiolabeled thymidine, neutral red staining of viable cells, or MTT staining of viable cells.

Significant tumor cell growth inhibition greater than about 50% at a dose of 100 µM or below is further indicative that the compound is useful for treating neoplastic lesions. Preferably, an $IC_{50}$ value is determined and used for comparative purposes. This value is the concentration of drug needed to inhibit tumor cell growth by 50% relative to the control. Preferably, the $IC_{50}$ value should be less than 100 µM for the compound to be considered further for potential use for treating neoplastic lesions.

E. Determining Whether a Compound Induces Apoptosis

In a second alternate embodiment, the screening method of the present invention further involves determining whether the compound induces apoptosis in cultures of tumor cells.

Two distinct forms of cell death may be described by morphological and biochemical criteria: necrosis and apoptosis. Necrosis is accompanied by increased permeability of the plasma membrane; the cells swell and the plasma membrane ruptures within minutes. Apoptosis is characterized by membrane blebbing, condensation of cytoplasm and the activation of endogenous endonucleases.

Apoptosis occurs naturally during normal tissue turnover and during embryonic development of organs and limbs. Apoptosis also is induced by cytotoxic T-lymphocytes and natural killer cells, by ionizing radiation and by certain chemotherapeutic drugs. Inappropriate regulation of apoptosis is thought to play an important role in many pathological conditions including cancer, AIDS, or Alzheimer's disease, etc. Compounds can be screened for induction of apoptosis using cultures of tumor cells maintained under conditions as described above. Treatment of cells with test compounds involves either pre- or post-confluent cultures and treatment for two to seven days at various concentrations. Apoptotic cells are measured in both the attached and "floating" compartments of the cultures. Both compartments are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature. (See, Piazza, G. A., et al., Cancer Research, 55:3110–16, 1995, which is incorporated herein by reference). The novel features include collecting both floating and attached cells, identification of the optimal treatment times and dose range for observing apoptosis, and identification of optimal cell culture conditions.

Following treatment with a compound, cultures can be assayed for apoptosis and necrosis by florescent microscopy following labeling with acridine orange and ethidium bromide. The method for measuring apoptotic cell number has previously been described by Duke & Cohen, "Morphological And Biochemical Assays Of Apoptosis," Current Protocols In Immunology, Coligan et al., eds., 3.17.1–3.17.16 (1992), which is incorporated herein by reference.

For example, floating and attached cells can be collected by trypsinization and washed three times in PBS. Aliquots of cells can be centrifuged. The pellet can then be re-suspended in media and a dye mixture containing acridine orange and ethidium bromide prepared in PBS and mixed gently. The mixture can then be placed on a microscope slide and examined for morphological features of apoptosis.

Apoptosis can also be quantified by measuring an increase in DNA fragmentation in cells that have been treated with test compounds. Commercial photometric EIA for the quantitative, in vitro determination of cytoplasmic histone-associated-DNA-fragments (mono- and oligonucleosomes) are available (Cell Death Detection ELISA$^{okys}$, Cat. No. 1,774,425, Boehringer Mannheim). The Boehringer Mannheim assay is based on a sandwich-enzyme-immunoassay principle using mouse monoclonal antibodies directed against DNA and histones, respectively. This allows the specific determination of mono- and oligonucleosomes in the cytoplasmatic fraction of cell lysates.

According to the vendor, apoptosis is measured in the following fashion. The sample (cell-lysate) is placed into a streptavidin-coated microtiter plate ("MTP"). Subsequently, a mixture of anti-histone-biotin and anti-DNA peroxidase conjugate are added and incubated for two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by a washing step, the amount of nucleosomes is quantified by the peroxidase retained in the immunocomplex. Peroxidase is determined photometrically with ABTS7 (2,2'-Azido-[3-ethylbenzthiazolin-sulfonate]) as substrate.

For example, SW-480 colon adenocarcinoma cells are plated in a 96-well MTP at a density of 10,000 cells per well. Cells are then treated with test compound, and allowed to incubate for 48 hours at 37° C. After the incubation, the MTP is centrifuged, and the supernatant is removed. The cell pellet in each well is then resuspended in lysis buffer for 30 minutes. The lysates are then centrifuged and aliquots of the supernatant (i.e., the cytoplasmic fraction) are transferred into a streptavidin-coated MTP. Care is taken not to shake the lysed pellets (i.e. cell nuclei containing high molecular weight, unfragmented DNA) in the MTP. Samples are then analyzed.

Fold stimulation (FS=$OD_{max}/OD_{veh}$), an indicator of apoptotic response, is determined for each compound tested at a given concentration. $EC_{50}$ values may also be determined by evaluating a series of concentrations of the test compound.

Statistically significant increases in apoptosis (i.e., greater than 2 fold stimulation at a concentration of 100 $\mu$M) are further indicative that the compound is useful for treating neoplastic lesions. Preferably, the $EC_{50}$ value for apoptotic activity should be less than 100 $\mu$M for the compound to be further considered for potential use for treating neoplastic lesions. $EC_{50}$ is herein defined as the concentration that causes 50% induction of apoptosis relative to vehicle treatment.

F. Mammary Gland Organ Culture Model Tests

Test compounds identified by the above methods can be tested for antineoplastic activity by their ability to inhibit the incidence of pre-neoplastic lesions in a mammary gland organ culture system. This mouse mammary gland organ culture technique has been successfully used by other investigators to study the effects of known antineoplastic agents such as certain NSAIDs, retinoids, tamoxifen, selenium, and certain natural products, and is useful for validation of the screening method of the present invention.

For example, female BALB/c mice can be treated with a combination of estradiol and progesterone daily, in order to prime the glands to be responsive to hormones in vitro. The animals are sacrificed, and thoracic mammary glands are excised aseptically and incubated for ten days in growth media supplemented with insulin, prolactin, hydrocortisone, and aldosterone. DMBA (7,12-dimethylbenz(a)anthracene) is added to medium to induce the formation of premalignant lesions. Fully developed glands are then deprived of prolactin, hydrocortisone, and aldosterone, resulting in the regression of the glands but not the pre-malignant lesions.

The test compound is dissolved in DMSO and added to the culture media for the duration of the culture period. At the end of the culture period, the glands are fixed in 10% formalin, stained with alum carmine, and mounted on glass slides. The incidence of forming mammary lesions is the ratio of the glands with mammary lesions to glands without lesions. The incidence of mammary lesions in test compound treated glands is compared with that of the untreated glands.

The extent of the area occupied by the mammary lesions can be quantitated by projecting an image of the gland onto a digitation pad. The area covered by the gland is traced on the pad and considered as 100% of the area. The space covered by each of the non-regressed structures is also outlined on the digitization pad and quantitated by the computer.

G. cGMP-Specific PDE Inhibitors

The invention includes the use of cGMP-specific PDE inhibitors such as exisulind and (Z)-5-fluoro-2-methyl-(4-pyridylidene)-3-(N-benzyl)indenylacetamide hydrochloride (also called CP461) in combination with a human epidermal growth factor receptor tyrosine kinase inhibitor to treat patients with cancer. The preparation, properties, and methods of use of cGMP-specific PDE inhibitors are more fully described below and in the references cited herein and incorporated by reference herein. Preferably, the cGMP-specific PDE inhibitor is (Z)-5-fluoro-2-methyl-(4-pyridylidene)-3-(N-benzyl)indenylacetamide hydrochloride.

H. Human Epidermal Growth Factor Receptor Tyrosine Kinase Inhibitors

The present invention discloses the use of an inhibitor of human epidermal growth factor receptor tyrosine kinase in combination with a cGMP-specific PDE inhibitor to treat patients with neoplasia. Preferably, the inhibitor of human epidermal growth factor receptor tyrosine kinase is Iressa. The preparation, properties, and methods of use of Iressa are more fully described below or in the references cited herein and incorporated by reference herein.

General Schemes for Producing c-GMP-Specific PDE Inhibitors

There are several general schemes for producing compounds useful in this invention (U.S. Pat. Nos. 5,948,779, 6,066,634, 6,166,053). One general scheme (which has several sub-variations) involves the case where both $R_3$ and $R_4$ are both hydrogen. This first scheme is described immediately below in Scheme I. The other general scheme (which also has several sub-variations) involves the case where at least one of $R_3$ and $R_4$ is a moiety other than hydrogen but within the scope of Formula I above. This second scheme is described below as "Scheme II."

The general scheme for preparing compounds where both $R_3$ and $R_4$ are both hydrogen is illustrated in Scheme I, which is described in part in U.S. Pat. No. 3,312,730, which is incorporated herein by reference. In Scheme I, $R_1$ is as defined in Formula I above. However, in Scheme I, that substituent can also be a reactive moiety (e.g. a nitro group) that later can be reacted to make a large number of other substituted indenes from the nitro-substituted indenes.

Scheme I
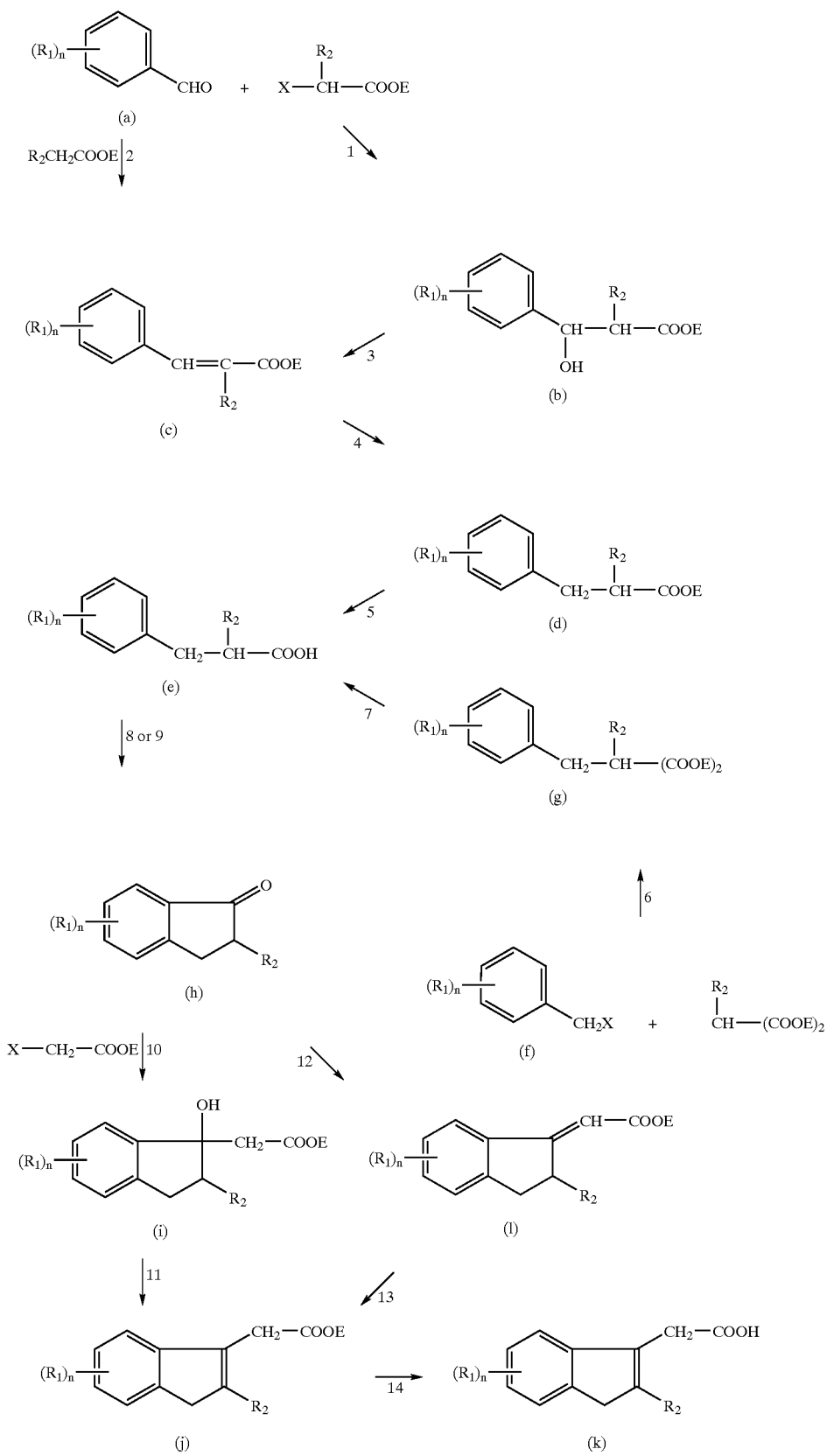

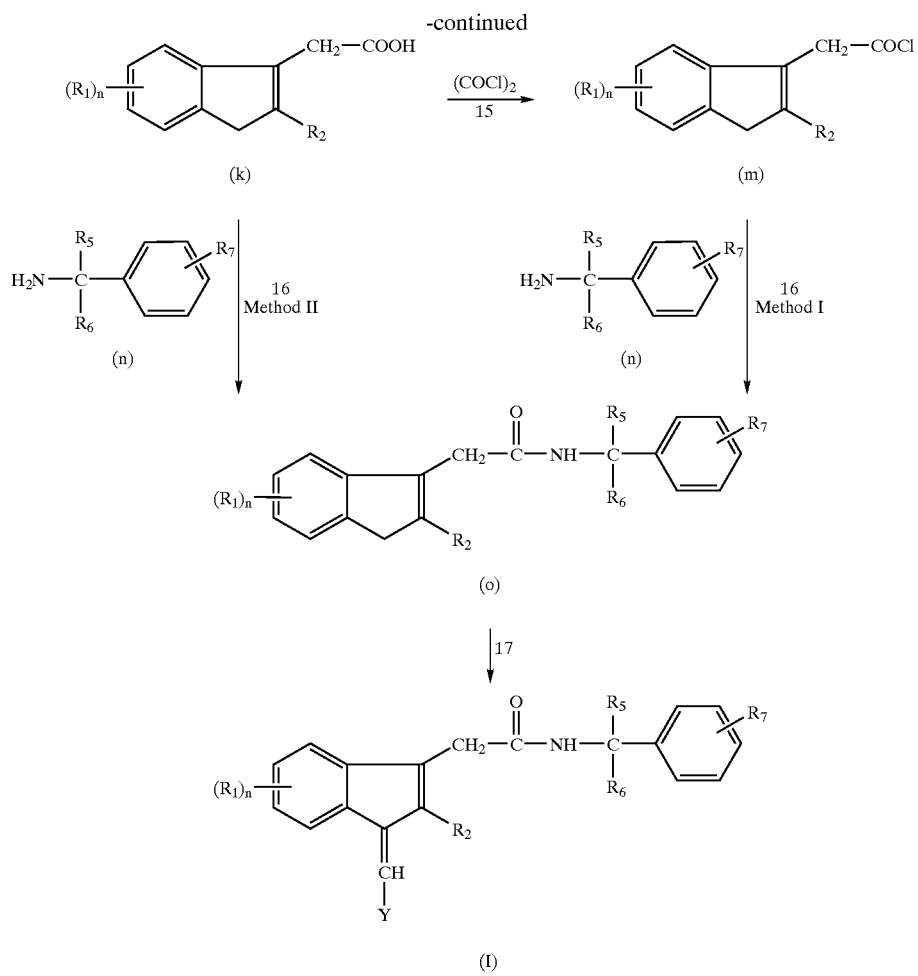

In Scheme I, several sub-variations can be used. In one sub-variation, a substituted benzaldehyde (a) may be condensed with a substituted acetic ester in a Knoevenagel reaction (see reaction 2) or with an α-halogeno propionic ester in a Reformatsky Reaction (see reactions 1 and 3). The resulting unsaturated ester (c) is hydrogenated and hydrolyzed to give a substituted benzyl propionic acid (e) (see reactions 4 and 5). Alternatively, a substituted malonic ester in a typical malonic ester synthesis (see reactions 6 and 7) and hydrolysis decarboxylation of the resulting substituted ester (g) yields the benzyl propionic acid (e) directly. This latter method is especially preferable for nitro and alkylthio substituents on the benzene ring.

The next step is the ring closure of the β-aryl proponic acid (e) to form an indanone (h) which may be carried out by a Friedel-Crafts Reaction using a Lewis acid catalyst (Cf. Organic Reactions, Vol. 2, p. 130) or by heating with polyphosphoric acid (see reactions 8 and 9, respectively). The indanone (h) may be condensed with an α-halo ester in the Reformatsky Reaction to introduce the aliphatic acid side chain by replacing the carboxyl group (see reaction 10). Alternately, this introduction can be carried out by the use of a Wittig Reaction in which the reagent is a α-triphenylphosphinyl ester, a reagent which replaces the carbonyl with a double bond to the carbon (see reaction 12). This product (1) is then immediately rearranged into the indene (j)(see reaction 13). If the Reformatsky Reaction route is used, the intermediate 3-hydroxy-3-aliphatic acid derivative i must be dehydrated to the indene (j) (see reaction 11).

The indenylacetic acid (k) in THF then is allowed to react with oxalyl or thionyl chloride or similar reagent to produce the acid chloride (m) (see reaction 15), whereupon the solvent is evaporated. There are two methods to carry out reaction 16, which is the addition of the benzylamine side chain (n).

Method (I)

In the first method, the benzylamine (n) is added slowly at room temperature to a solution of 5-fluoro-2-methyl-3-indenylacetyl chloride in $CH_2Cl_2$. The reaction mixture is refluxed overnight, and extracted with aqueous HCl (10%), water, and aqueous $NaHCO_3$ (5%). The organic phase is dried ($Na_2SO_4$) and is evaporated to give the amide compound (o)

Method (II)

In the second method, the indenylacetic acid (k) in DMA is allowed to react with a carbodiimide (e.g. N-(3-dimethylaminopropyl)-N'-ethylcarbodiimide hydrochloride) and benzylamine at room temperature for two days. The reaction mixture is added dropwise to stirred ice water. A yellow precipitate is filtered off, is washed with water, and is dried in vacuo. Recrystallization gives the amide compound (o).

Compounds of the type a' (Scheme III), o (Scheme I), t (Scheme II), y (Scheme IIB) may all be used in the condensation reaction shown in Scheme III.

Substituents

X=halogen, usually Cl or Br.

E=methyl, ethyl or benzyl, or lower acyl.

$R_1$, $R_2$, $R_6$, $R_5$, and $R_7$=as defined in Formula I.

Y, n and m=as defined in Formula I.

Reagents and general conditions for Scheme I (numbers refer to the numbered reactions):

(1) Zn dust in anhydrous inert solvent such as benzene and ether.
(2) $KHSO_4$ or p-toluene sulfonic acid.
(3) $NaOC_2H_5$ in anhydrous ethanol at room temperature.
(4) $H_2$ palladium on charcoal, 40 p.s.i. room temperature.
(5) NaOH in aqueous alcohol at 20–100°.
(6) $NaOC_2H_5$ or any other strong base such as NaH or K-t-butoxide.
(7) Acid.
(8) Friedel-Crafts Reaction using a Lewis Acid catalyst Cf. Organic Reactions, Vol. II, p. 130.
(9) Heat with polyphosphoric acid.
(10) Reformatsky Reaction: Zn in inert solvent, heat.
(11) p-Toluene sulfonic acid and $CaCl_2$ or $I_2$ at 200°
(12) Wittig Reaction using $(C_6H_5)_3$ P=C—COOE 20–80° in ether or benzene
(13) (a) $NBS/CCl_4$/benzoyl peroxide
(b) $PtO_2/H_2$ (1 atm.)/acetic acid
(14) (a) NaOH
(b) HCl
(15) Oxalyl or thionyl chloride in $CH_2Cl_2$ or THF
(16) Method I: 2 equivalents of $NH_2$—$C(R_5R_6)$-Ph-$(R_7)_m$
Method II: carbodiimide in THF
(17) 1N $NaOCH_3$ in MeOH under reflux conditions Indanones within the scope of compound (h) in Scheme I are known in the literature and are thus readily available as intermediates for the remainder of the synthesis so that reactions 1–7 can be conveniently avoided. Among such known indanones are:

5-methoxyindanone
6-methoxyindanone
5-methylindanone
5-methyl-6-methoxyindanone
5-methyl-7-chloroindanone
4-methoxy-7-chloroindanone
4-isopropyl-2,7-dimethylindanone
5,6,7-trichloroindanone
2-n-butylindanone
5-methylthioindanone Scheme II has two mutually exclusive sub-schemes: Scheme IIA and Scheme II B. Scheme II A is used when $R_3$ is hydroxy and $R_4$ is hydrogen or when the two substituents form an oxo group. When $R_3$ is lower alkyl amino, Scheme II B is employed.

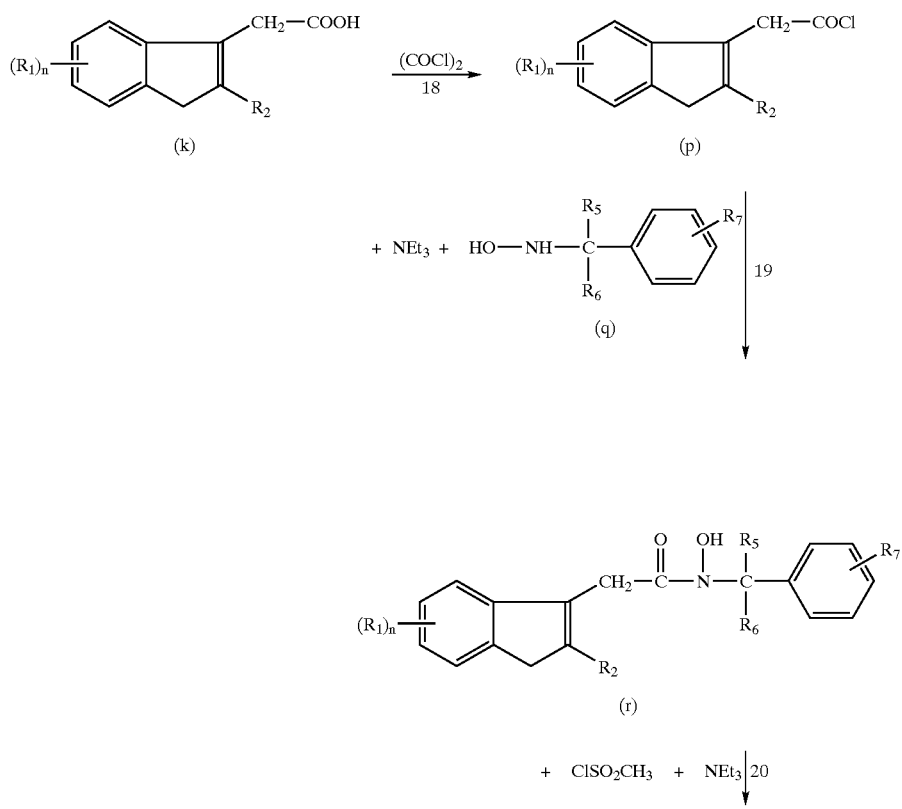

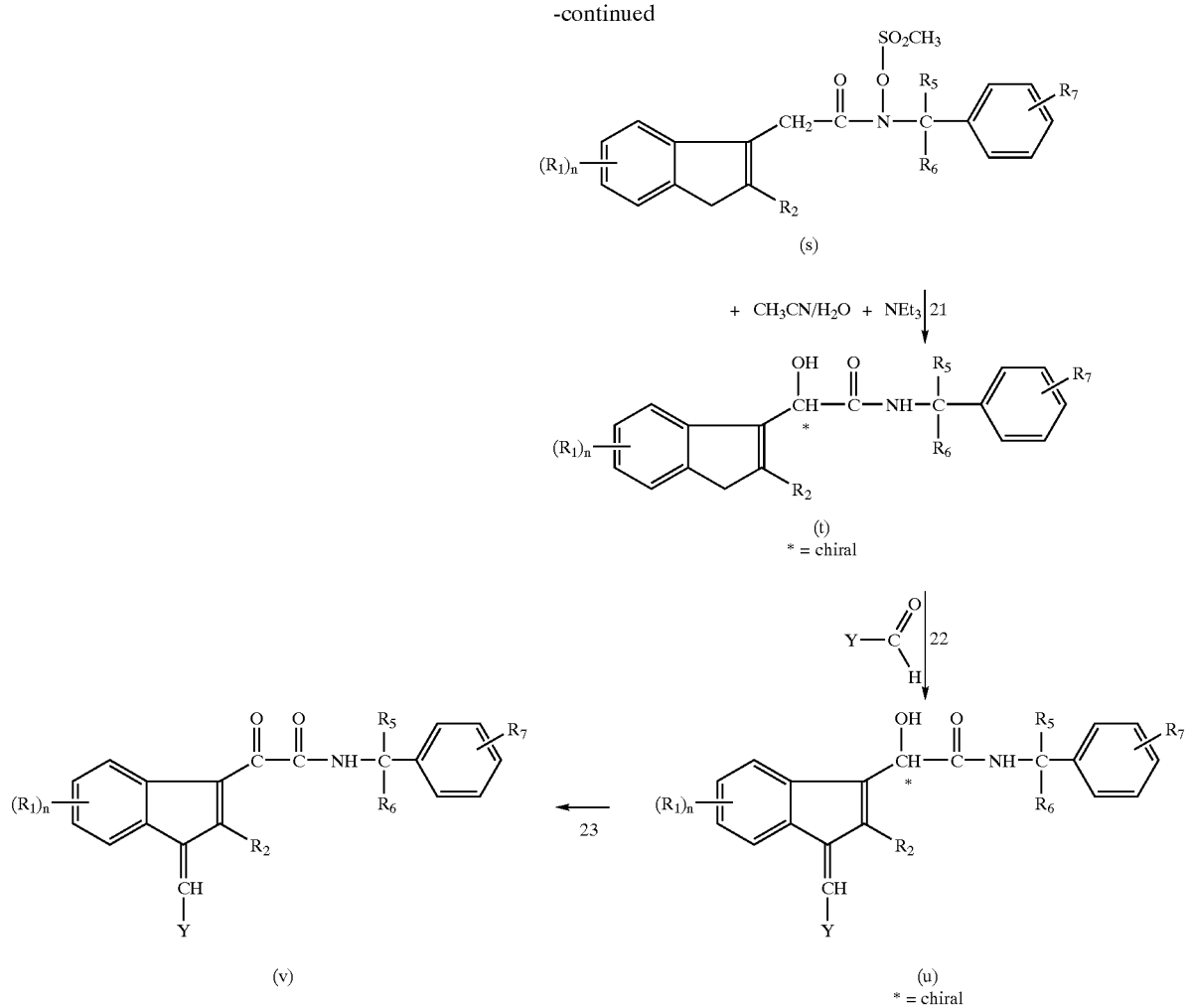

Similar to Scheme I, in Scheme IIA the indenylacetic acid (k) in THF is allowed to react with oxalylchloride under reflux conditions to produce the acid chloride (p) (see reaction 18), whereupon the solvent is evaporated. In reaction 19, a 0° C. mixture of a benzyl hydroxylamine hydrochloride (q) and $Et_3N$ is treated with a cold solution of the acid chloride in $CH_2Cl_2$ over a period of 45–60 minutes. The mixture is warmed to room temperature and stirred for one hour, and is treated with water. The resulting organic layer is washed with 1 N HCl and brine, is dried over magnesium sulfate and is evaporated. The crude product, a N-hydroxy-N-benzyl acetamide (r) is purified by crystallization or flash chromatography. This general procedure is taught by Hoffman et al., JOC 1992, 57, 5700–5707.

The next step is the preparation of the N-mesyloxy amide (s) in reaction 20, which is also taught by Hoffman et al., JOC 1992, 57, 5700–5707. Specifically, to a solution of the hydroxamic acid (r) in $CH_2Cl_2$ at 0° C. is added triethylamine. The mixture is stirred for 10–12 minutes, and methanesulfonyl chloride is added dropwise. The mixture is stirred at 0° C. for two hours, is allowed to warm to room temperature, and is stirred for another two hours. The organic layer is washed with water, 1 N HCl, and brine, and is dried over magnesium sulfate. After rotary evaporation, the product(s) is usually purified by crystallization or flash chromatography.

The preparation of the N-benzyl-α-(hydroxy) amide (t) in reaction 21, is also taught by Hoffman et al., JOC 1992, 57, 5700–5707 and Hoffman et al., JOC 1995, 60, 4121–4125. Specifically, to a solution of the N-(mesyloxy) amide (s) in $CH_3CN/H_2O$ is added triethylamine in $CH_3CN$ over a period of 6–12 hours. The mixture is stirred overnight. The solvent is removed, and the residue is dissolved in ethyl acetate. The solution is washed with water, 1 N HCl, and brine, and is dried over magnesium sulfate. After rotary evaporation, the product (t) is usually purified by recrystallization.

Reaction 22 in Scheme IIA involves a condensation with certain aldehydes, which is described in Scheme III below, a scheme that is common to products made in accordance with Schemes I, IIA and IIB.

The final reaction 23 in Scheme IIA is the preparation of the N-benzyl-α-ketoamide (v), which involves the oxidation of a secondary alcohol (u) to a ketone by e.g. a Pfitzner-Moffatt oxidation, which selectively oxidizes the alcohol Scheme IIB

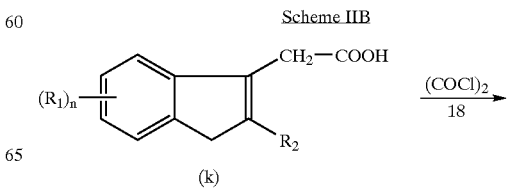

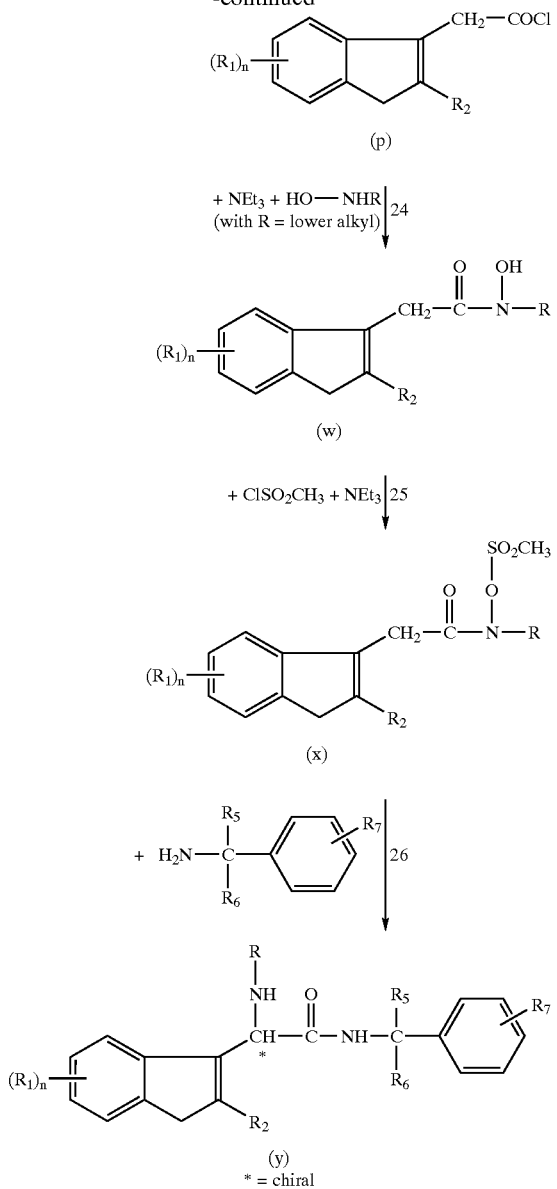

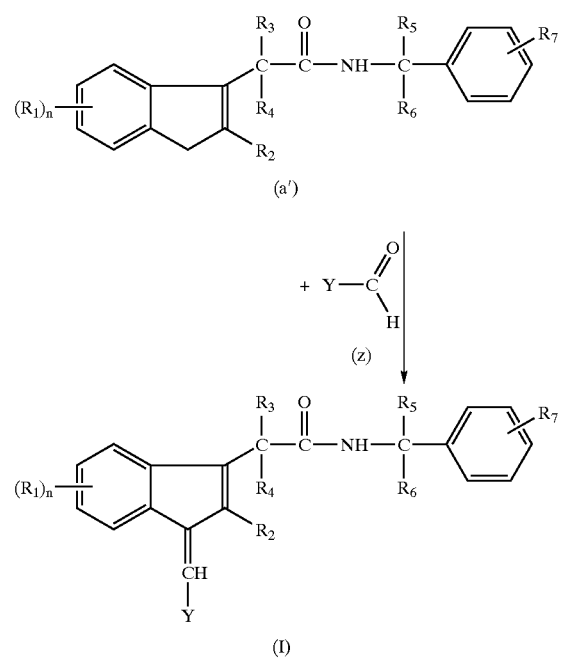

without oxidizing the Y group. Compounds (u) and (v) may be derivatized in order to obtain compounds with $R_3$ and $R_4$ groups as set forth in Formula I.

As explained above, Scheme IIB is employed when $R_3$ is lower alkyl amino. Similar to Scheme I, in Scheme IIB the indenylacetic acid (k) in THF is allowed to react with oxalylchloride under reflux conditions to produce the acid chloride (p) (see reaction 18), whereupon the solvent is evaporated. In reaction 24, a mixture of an alkyl hydroxylamine hydrochloride (i.e. HO—NHR where R is a lower alky, preferably isopropyl) and $Et_3N$ is treated at 0° C. with a cold solution of the acid chloride in $CH_2Cl_2$ over a period of 45–60 minutes. The mixture is warmed to room temperature and is stirred for one hour, and is diluted with water. The resulting organic layer is washed with 1 N HCl and brine, is dried over magnesium sulfate and is evaporated. The crude product, a N-hydroxy-N-alkyl acetamide (w) is purified by crystallization or flash chromatography. This general procedure is also taught by Hoffman et al., JOC 1992, 57, 5700–5707

The preparation of the N-mesyloxy amide (x) in reaction 25, which is also taught by Hoffman et al., JOC 1992, 57, 5700–5707. Specifically, a solution of the hydroxamic acid (w) in $CH_2Cl_2$ at 0° C. is treated with triethylamine, is stirred for 10–12 minutes, and is treated dropwise with methanesulfonyl chloride. The mixture is stirred at 0° C. for two hours, is allowed to warm to room temperature, and is stirred for another two hours. The resulting organic layer is washed with water, 1 N HCl, and brine, and is dried over magnesium sulfate. After rotary evaporation, the product (x) is usually purified by crystallization or flash chromatography.

The preparation of the N-benzyl indenyl-α-loweralkylamino-acetamide compound (y) in Scheme IIB as taught by Hoffman et al., JOC 1995, 60, 4121–25 and J. Am. Chem Soc. 1993, 115, 5031–34, involves the reaction of the N-mesyloxy amide (x), with a benzylamine in $CH_2Cl_2$ at 0° C. is added over a period of 30 minutes. The resulting solution is stirred at 0° C. for one hour and at room temperature overnight. The solvent is removed, and the residue is treated with 1 N NaOH. The extract with $CH_2Cl_2$ is washed with water and is dried over magnesium sulfate. After rotary evaporation, the product (y) is purified by flash chromatography or crystallization.

Scheme III involves the condensation of the heterocycloaldehydes (i.e. Y—CHO) with the indenyl amides to produce the final compounds of Formula I. This condensation is employed, for example, in reaction 17 in Scheme I above and in reaction 22 in Scheme IIA. It is also used to convert compound (y) in Scheme IIB to final compounds of Formula I.

In Scheme III, the amide (a') from the above schemes, a N-heterocycloaldehyde (z), and sodium methoxide (1 M in methanol) are stirred at 60° C. under nitrogen for 24 hours. After cooling, the reaction mixture is poured into ice water. A solid is filtered off, is washed with water, and is dried in vacuo. Recrystallization provides a compound of Formula I in Schemes I and IIB and the intermediate (u) in Scheme IIA.

As has been pointed out above, it is preferable in the preparation of many types of the compounds of this invention, to use a nitro substituent on the benzene ring of the indanone nucleus and convert it later to a desired substituent since by this route a great many substituents can be reached. This is done by reduction of the nitro to the amino group followed by use of the Sandmeyer Reaction to introduce chlorine, bromine, cyano or xanthate in place of the amino. From the cyano derivatives hydrolysis yields the carboxamide and carboxylic acid; other derivatives of the carboxy group such as the esters can then be prepared. The xanthates, by hydrolysis, yield the mercapto group that may be oxidized readily to the sulfonic acid or alkylated to an alkylthio group which can then be oxidized to alkylsulfonyl groups. These reactions may be carried out either before or after the introduction of the 1-substituent.

Based on the above-identified schema, the following are examples of compounds of the invention and their production and identification:

EXAMPLE 1

(Z)-5-Fluoro-2-Methyl-(4-Pyridinylidene)-3-(N-Benzyl)-Indenylacetamide (A) p-Fluoro-α-methylcinnamic acid p-Fluorobenzaldehyde (200 g, 1.61 mol), propionic anhydride (3.5 g, 2.42 mol) and sodium propionate (155 g, 1.61 mol) are mixed in a one liter three-necked flask which had been flushed with nitrogen. The flask is heated gradually in an oil-bath to 140° C. After 20 hours, the flask is cooled to 100° C. and poured into 8 l of water. The precipitate is dissolved by adding potassium hydroxide (302 g) in 2 l of water. The aqueous solution is extracted with ether, and the ether extracts are washed with potassium hydroxide solution. The combined aqueous layers are filtered, are acidified with concentrated HCl, and are filtered. The collected solid, p-fluoro-α-methylcinnamic acid, is washed with water, and is dried and used as obtained.

(B) p-Fluoro-α-methylhydrocinnamic acid

To p-fluoro-α-methylcinnamic acid (177.9 g, 0.987 mol) in 3.6 l ethanol is added 11.0 g of 5% Pd/C. The mixture is reduced at room temperature under a hydrogen pressure of 40 p.s.i. When hydrogen uptake ceases, the catalyst is filtered off, and the solvent is evaporated in vacuo to give the product, p-fluoro-α-methylhydrocinnamic acid, which was used directly in the next step.

(C) 6-Fluoro-2-methylindanone

To 932 g polyphosphoric acid at 70° C. (steam bath) is added p-fluoro-α-methylhydrocinnamic acid (93.2 g, 0.5 mol) slowly with stirring. The temperature is gradually raised to 95° C., and the mixture is kept at this temperature for 1 hour. The mixture is allowed to cool and is added to 2 l. of water. The aqueous suspension is extracted with ether. The extract is washed twice with saturated sodium chloride solution, 5% $Na_2CO_3$ solution, and water, and is dried, and is concentrated on 200 g silica-gel; the slurry is added to a five pound silica-gel column packed with 5% ether-petroleum ether. The column is eluted with 5–10% ether-petroleum ether, to give 6-fluoro-2-methylindanone. Elution is followed by TLC.

(D) 5-fluoro-2-methylindenyl-3-acetic acid

A mixture of 6-fluoro-2-methylindanone (18.4 g, 0.112 mol), cyanoacetic acid (10.5 g, 0.123 mol), acetic acid (6.6 g), and ammonium acetate (1.7 g) in dry toluene (15.5 ml) is refluxed with stirring for 21 hours, as the liberated water is collected in a Dean Stark trap. The toluene is evaporated, and the residue is dissolved in 60 ml of hot ethanol and 14 ml of 2.2 N aqueous potassium hydroxide solution. 22 g of 85% KOH in 150 ml of water is added, and the mixture refluxed for 13 hours under nitrogen. The ethanol is removed under vacuum, and 500 ml water is added. The aqueous solution is extracted well with ether, and is then boiled with charcoal. The aqueous filtrate is acidified to pH 2 with 50% cold hydrochloric acid. The precipitate is dried and 5-fluoro-2-methylindenyl-3-acetic acid (M.P. 164–166° C.) is obtained.

(E) 5-fluoro-2-methylindenyl-3-acetyl chloride 5-fluoro-2-methylindenyl-3-acetic acid (70 mmol) in THF (70 ml) is allowed to react with oxalylchloride (2 M in $CH_2Cl_2$; 35 ml; 70 mmol) under reflux conditions (24 hours). The solvent is evaporated to yield the title compound, which is used as such in the next step.

(F) 5-Fluoro-2-methyl-3-(N-benzyl)-indenylacetamide

Benzylamine (5 mmol) is added slowly at room temperature to a solution of 5-fluoro-2-methylindenyl-3-acetyl chloride (2.5 mmol.) in $CH_2Cl_2$ (10 ml). The reaction mixture is refluxed overnight, and is extracted with aqueous HCl (10%), water, and aqueous $NaHCO_3$ (5%). The organic phase is dried ($Na_2SO_4$) and is evaporated to give the title compound, which is recrystallized from $CH_2Cl_2$ to give the title compound as a white solid (m.p. 144° C.).

(G) (Z)-5-Fluoro-2-methyl-(4-pyridinylidene)-3-(N-benzyl)-indenylacetamide 5-fluoro-2-methyl-3-(N-benzyl)-indenylacetamide (3.38 mmol), 4-pyridinecarboxaldehyde (4 mmol), sodium methoxide (1M $NaOCH_3$ in methanol (30 ml)) are heated at 60° C. under nitrogen with stirring for 24 hours. After cooling, the reaction mixture is poured into ice water (200 ml). A solid is filtered off, washed with water, and dried in vacuo. Recrystallization from $CH_3CN$ gives the title compound (m.p. 202° C.) as a yellow solid ($R_1$=F, $R_2$=$CH_3$, $R_3$=H, $R_4$=H, $R_5$=H, $R_6$=H, $R_7$=H, n=1, m=1, Y=4-pyridinyl).

(H) (E)-5-Fluoro-2-methyl-(4-pyridinlidene)-3-(N-benzyl)-indenylacetamide

The mother liquor obtained from the $CH_3CN$ recrystallization of 1G is rich on the geometrical isomer of 1G. The E-isomer can be obtained pure by repeated recrystallizations from $CH_3CN$.

EXAMPLE 2

(Z)-5-Fluoro-2-Methyl-(3-Pyridinylidene)-3-(N-Benzyl)-Indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 3-pyridinecarboxaldehyde. Recrystallization from $CH_3CN$ gives the title compound (m.p. 175° C.)($R_1$=F, $R_2$=$CH_3$, $R_3$=H, $R_4$=H, $R_5$=H, $R_6$=H, $R_7$=H, n=1, m=1, Y=3-pyridinyl).

EXAMPLE 3

(Z)-5-Fluoro-2-Methyl-(2-Pyridinylidene)-3-(N-Benzyl)-Indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 2-pyridinecarboxaldehyde. Recrystallization from ethylacetate gives the title compound (m.p. 218° C.)($R_1$=F, $R_2$=$CH_3$, $R_3$=H, $R_4$=H, $R_5$=H, $R_6$=H, $R_7$=H, n=1, m=1, Y=2-pyridinyl).

EXAMPLE 4

(Z)-5-Fluoro-2-Methyl-(4-Quinolinylidene)-3-(N-Benzyl)-Indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 4-quinolinecarboxaldehyde. Recrystallization from ethylacetate gives the title compound (m.p. 239° C.)($R_1$=F, $R_2$=$CH_3$, $R_3$=H, $R_4$=H, $R_5$=H, $R_6$=H, $R_7$=H, n=1, m=1, Y=4-quinolinyl).

EXAMPLE 5

(Z)-5-Fluoro-2-Methyl-(4,6-Dimethyl-2-Pyridinylidene)-3-(N-Benzyl)-Indenylacetamide 5-Fluoro-2-methyl-3-(N-benzyl)-indenylacetamide from Example 1, part F is allowed to react with 4,6-dimethyl-2-pyridinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=4,6-dimethyl-2-pyridinyl).

EXAMPLE 6

(Z)-5-Fluoro-2-Methyl-(3-Quinolinylidene)-3-(N-Benzyl)-Indenylacetamide

5-Fluoro-2-methyl-3-(N-benzyl)-indenylacetamide from Example 1, part F is allowed to react with 3-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=3-quinolinyl)

EXAMPLE 7

(Z)-5-Fluoro-2-Methyl-(2-Quinolinylidene)-3-(N-Benzyl)-Indenylacetamide

5-Fluoro-2-methyl-3-(N-benzyl)-indenylacetamide from Example 1, part F is allowed to react with 2-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=2-quinolinyl).

EXAMPLE 8

(Z)-5-Fluoro-2-Methyl-(Pyrazinylidene)-3-(N-Benzyl)-Indenylacetamide

5-Fluoro-2-methyl-3-(N-benzyl)-indenylacetamide from Example 1, part F is allowed to react with pyrazinealdehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=pyrazinyl).

EXAMPLE 9

(Z)-5-Fluoro-2-Methyl-(3-Pyridazinylidene)-3-(N-Benzyl)-Indenylacetamide

5-Fluoro-2-methyl-3-(N-benzyl)-indenylacetamide from Example 1, part F is allowed to react with pyridazine-3-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=3-pyridazinyl).

EXAMPLE 10

(Z)-5-Fluoro-2-Methyl-(4-Pyrimidinylidene)-3-(N-Benzyl)-Indenylacetamide

5-Fluoro-2-methyl-3-(N-benzyl)-indenylacetamide from Example 1, part F is allowed to react with pyrimidine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=4-pyrimidinyl).

EXAMPLE 11

(Z)-5-Fluoro-2-Methyl-(2-Methyl-4-Pyrimidinylidene)-3-(N-Benzyl)-Indenylacetamide 5-Fluoro-2-methyl-3-(N-benzyl)-indenylacetamide from Example 1, part F is allowed to react with 2-methyl-pyrimidine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=2-methyl-4-pyrimidinyl).

EXAMPLE 12

(Z)-5-Fluoro-2-Methyl-(4-Pyridazinylidene)-3-(N-Benzyl)-Indenylacetamide

5-Fluoro-2-methyl-3-(N-benzyl)-indenylacetamide from Example 1, part F is allowed to react with pyridazine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=4-pyridazinyl).

EXAMPLE 13

(Z)-5-Fluoro-2-Methyl-(1-Methyl-3-Indolylidene)-3-(N-Benzyl)-Indenylacetamide

5-Fluoro-2-methyl-3-(N-benzyl)-indenylacetamide from Example 1, part F is allowed to react with 1-methylindole-3-carboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=1-methyl-3-indolyl).

EXAMPLE 14

(Z)-5-Fluoro-2-Methyl-(1-Acetyl-3-Indolylidene)-3-(N-Benzyl)-Indenylacetamide

5-Fluoro-2-methyl-3-(N-benzyl)-indenylacetamide from Example 1, part F is allowed to react with 1-acetyl-3-indolecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=1-acetyl-3-indolyl).

EXAMPLE 15

(Z)-5-Fluoro-2-Methyl-(4-Pyridinylidene)-3-(N-2-Fluorobenzyl)-Indenylacetamide (A) 5-Fluoro-2-methyl-3-(N-2-fluorobenzyl)-indenylacetamide This compound is obtained from 5-fluoro-2-methylindenyl-3-acetyl chloride (Example 1E) using the procedure of Example 1, Part F and replacing benzylamine with 2-fluorobenzylamine.

(B) (Z)-5-Fluoro-2-methyl-(4-pyridinylidene)-3-(N-2-fluorobenzyl)-indenylacetamide 5-Fluoro-2-methyl-3-(N-2-fluorobenzyl)-indenylacetamide is allowed to react with 4-pryidinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=4-pyridinyl).

EXAMPLE 16

(Z)-5-Fluoro-2-Methyl-(3-Pyridinylidene)-3-(N-2-Fluorobenzyl)-Indenylacetamide

5-Fluoro-2-methyl-3-(N-2-fluorobenzyl)-indenylacetamide from Example 15, part A is allowed to react with 3-pryidinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyridinyl).

EXAMPLE 17

(Z)-5-Fluoro-2-Methyl-(2-Pyridinylidene)-3-(N-2-Fluorobenzyl)-Indenylacetamide

5-Fluoro-2-methyl-3-(N-2-fluorobenzyl)-indenylacetamide from Example 15, part A is allowed to react with 2-pyridinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=2-pyridinyl).

EXAMPLE 18

(Z)-5-Fluoro-2-Methyl-(4-Quinolinylidene)-3-(N-2-Fluorobenzyl)-Indenylacetamide

5-Fluoro-2-methyl-3-(N-2-fluorobenzyl)-indenylacetamide from Example 15, part A is allowed to react with 4-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-quinolinyl).

EXAMPLE 19

(Z)-5-Fluoro-2-Methyl-(3-Pyrazinylidene)-3-(N-2-Fluorobenzyl)-Indenylacetamide

5-Fluoro-2-methyl-3-(N-2-fluorobenzyl)-indenylacetamide from Example 15, part A is allowed to react with pyrazinealdehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyrazinyl).

EXAMPLE 20

(Z)-5-Fluoro-2-Methyl-(3-Pyridazinylidene)-3-(N-2-Fluorobenzyl)-Indenylacetamide 5-Fluoro-2-methyl-3-(N-2-fluorobenzyl)-indenylacetamide from Example 15, part A is allowed to react with 3-pryidaziine-3-aldehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyridazinyl).

EXAMPLE 21

(Z)-5-Fluoro-2-Methyl-(3-Pyrimidinylidene)-3-(N-2-Fluorobenzyl)-Indenylacetamide 5-Fluoro-2-methyl-3-(N-2-fluorobenzyl)-indenylacetamide from Example 15, part A is allowed to react with pryimidine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyrimidinyl).

EXAMPLE 22

(Z)-5-Fluoro-2-Methyl-(4-Pyridazinylidene)-3-(N-2-Fluorobenzyl)-Indenylacetamide 5-Fluoro-2-methyl-3-(N-2-fluorobenzyl)-indenylacetamide from Example 15, part A is allowed to react with pryidazine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=4-pyridazinyl).

EXAMPLE 23

(Z)-5-Fluoro-2-Methyl-(4-Pyridinylidene)-3-(N-(S-α-Hydroxymethyl)Benzyl)-Indenylacetamide (A) 5-Fluoro-2-methyl-3-(N-(S-α-hydroxylmethyl)benzyl)-indenylacetamide 5-Fluoro-2-methylindenyl-3-acetic acid (from Example 1D) (2.6 mmol) in DMA (2 ml) is allowed to react with n-(3-dimethylaminopropyl)-N'-ethylcarbodiimide hydrochloride (4 mmol) and S-2-amino-2-phenylethanol (3.5 mmol) at room temperature for two days. The reaction mixture is added dropwise to stirred ice water (50 ml). A white precipitate is filtered off, washed with water (5 ml), and dried in vacuo. Recrystallization from ethylacetate gives the desired compound.

(B) (Z)-5-fluoro-2-methyl-(4-pyridinylidene)-3-(N-(S-α-hydroxymethyl)benzyl)-indenylacetamide 5-Fluoro-2-methyl-3-(N-(S-α-hydroxylmethyl)benzyl)-indenylacetamide from part A is allowed to react with 4-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyridinyl).

EXAMPLE 24

(Z)-5-Fluoro-2-Methyl-(3-Pyridinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with 3-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=3-pyridinyl).

EXAMPLE 25

(Z)-5-Fluoro-2-Methyl-(2-Pyridinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with 2-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=2-pyridinyl).

EXAMPLE 26

(Z)-5-Fluoro-2-Methyl-(4-Quinolinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with 4-quinolinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-quinolinyl).

EXAMPLE 27

(Z)-5-Fluoro-2-Methyl-(Pyrazidinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with pryazidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=pyrazidinyl).

EXAMPLE 28

(Z)-5-Fluoro-2-Methyl-(3-Pyridazinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with pryidazine-3-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=3-pyridazinyl).

EXAMPLE 29

(Z)-5-Fluoro-2-Methyl-(4-Pyrimidinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with pryimidine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyrimidinyl).

EXAMPLE 30

(Z)-5-Fluoro-2-Methyl-(4-Pyridazinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with pryidazine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyridazinyl).

EXAMPLE 31 rac-(Z)-5-Fluoro-2-Methyl-(4-Pyridinylidene)-3-(N-Benzyl)Indenyl-α-Hydroxyacetamide (A) 5-fluoro-2-methyl-3-(N-benzyl-N-hydroxy)-indenylacetamide To a mixture of N-benzylhydroxylamine hydrochoride (12 mmol) and $Et_3N$ (22 mmol) in $CH_2Cl_2$ (100 ml) at 0° C. is added a cold solution of 5-fluoro-2-methylindenyl-3-acetyl chloride (Example 1, Step E) (10 mmol) in $CH_2Cl_2$ (75 ml) over a period of 45–60 minutes. The mixture is warmed to room temperature and is stirred for 1 hour. The mixture is diluted with water (100 ml), and the organic layer is washed with HCl (2×25 ml) and brine (2×100 ml), dried ($MgSO_4$) and evaporated. The crude product is purified with flash chromatography to give the title compound.

(B) 5-Fluoro-2-methyl-3-(N-benzyl-N-mesyloxy)-indenylacetamide

To a solution of 5-fluoro-2-methyl-3-(N-benzyl-N-hydroxy)-indenylacetamide (5 mmol) in $CH_2Cl_2$ (25 ml) at 0° C. is added triethylamine (5 mmol). The mixture is stirred for 10 minutes, and methanesulfonyl chloride (5.5 mmol) is added dropwise. The solution is stirred at 0° C. for 2 hours, allowed to warm to room temperature, and stirred for another 2 hours. The organic layer is washed with water (2×20 ml), in HCl (15 ml), and brine (20 ml) and dried over $MgSO_4$. After rotary evaporation, the product is purified with flash chromatography to give the title compound.

(C) rac-5-Fluoro-2-methyl-3-(N-benzyl)-α-hydroxyindenylacetamide

To a solution of 5-fluoro-2-methyl-3-(N-benzyl-N-mesyloxy)-indenylacetamide (2 mmol) in $CH_3CN/H_2O$ (12 ml. each) is added triethylamine (2.1 mmol) in $CH_3CN$ (24 ml) over a period of 6 hours. The mixture is stirred overnight. The solvent is removed, and the residue diluted with ethyl acetate (60 ml), washed with water (4×20 ml), in HCl (15 ml), and brine (20 ml) and dried over $MgSO_4$. After rotary evaporation, the product is purified by recrystallization to give the title compound.

(D) rac-(Z)-5-Fluoro-2-methyl-(4-pyridinylidene)-3-(N-benzyl)-indenyl-α-hydroxyacetamide is obtained from rac-5-fluoro-2-methyl-3-(N-benzyl)-α-hydroxyindenylacetamide using the procedure of Example 1, Part G ($R_1$=F, $R_2$=$CH_3$, $R_3$=OH, $R_4$=H, $R_5$=H, $R_6$=H, $R_7$=H, n=1, m=1, Y=4-pyridinyl).

EXAMPLE 32

2-[(Z)-5-Fluoro-2-Methyl-(4-Pyridinylidene)-3-(N-Benzyl)-Indenyl]-Oxyacetamide

For Pfitzner-Moffatt oxidation, a solution of rac-(Z)-5-fluoro-2-methyl-(4-pyridinylidene)-3-(N-benzyl)-indenyl-α-hydroxyacetamide (1 mmol) in DMSO (5 ml) is treated with dicyclohexylcarbodiimide (3 mmol). The mixture is stirred overnight, and the solvent is evaporated. The crude product is purified by flash chromatography to give the title compound ($R_1$=F, $R_2$=$CH_3$, $R_3$ and $R_4$ together form C=O, $R_5$=H, $R_6$=H, $R_7$=H, n=1, m=1, and Y=4-pyridinyl).

EXAMPLE 33 rac-(Z)-5-Fluoro-2-Methyl-(4-Pyridinylidene)-3-(N-Benzyl)-Indenyl-α-(2-Propylamino)-Acetamide (A) 5-Fluoro-2-methyl-3-(N-2-propyl-N-hydroxy)-indenylacetamide is obtained from 5-fluoro-2-methylindenyl-3-acetyl chloride (Example 1, Step E) using the procedure of Example 31, Part A and replacing N-benzylhydroxylamine hydrochloride with N-2-propyl hydroxylamine hydrochloride.

(B) 5-Fluoro-2-methyl-3-(N-2-propyl-N-mesyloxy)-indenylacetamide is obtained according to the procedure of Example 31, Part B.

(C) rac-5-Fluoro-2-methyl-3-(N)-benzyl)-α-(2-propylamino)-acetamide. To 5-fluoro-2-methyl-3-(N-2-propyl-N-mesyloxy)-indenylacetamide (2 mmol) in $CH_2Cl_2$ (25 ml) at 0° C. is added benzylamine (4.4 mmol) in $CH_2Cl_2$ (15 ml) over a period of 30 minutes. The resulting solution is stirred at 0° C. for 1 hour, and at room temperature overnight. The solvent is removed, and the residue is treated with 1 N NaOH, and is extracted with $CH_2Cl_2$ (100 ml). The extract is washed with water (2×10 ml), and is dried over $MgSO_4$. After rotary evaporation, the product is purified by flash chromatography.

(D) rac-(Z)-5-Fluoro-2-methyl-(4-pyridinylidene)-3-(N-benzyl)-indenyl-α-(2-propylamino)-acetamide is obtained from rac-5-fluoro-2-methyl-3-(N-benzyl)-α-(2-propylamino)-acetamide using the procedure of Example 1, Part G ($R_1$=F, $R_2$=$CH_3$, $R_3$=isopropylamino, $R_4$=H, $R_5$=H, $R_6$=H, $R_7$=H, n=1, m=1, Y=4-pyridinyl).

EXAMPLE 34

(Z)-6-Methoxy-2-Methyl-(4-Pyridinylidene)-3-(N-Benzyl)-Indenylacetamide (A) Ethyl-2-Hydroxy-2-(p-Methoxyphenyl)-1-Methylpropionate In a 500 ml. 3-necked flask is placed 36.2 g. (0.55 mole) of zinc dust, a 250 ml. addition funnel is charged with a solution of 80 ml. anhydrous benzene, 20 ml. of anhydrous ether, 80 g. (0.58 mole) of p-anisaldehyde and 98 g. (0.55 mole) of ethyl-2-bromopropionate. About 10 ml. of the solution is added to the zinc dust with vigorous stirring, and the mixture is warmed gently until an exothermic reaction commences. The remainder is added dropwise at such a rate that the reaction mixture continues to reflux smoothly (ca. 30–35 min.). After addition is completed the mixture is placed in a water bath and refluxed for 30 minutes. After cooling to 0°, 250 ml. of 10% sulfuric acid is added with vigorous stirring. The benzene layer is extracted twice with 50 ml. portions of 5% sulfuric acid and washed twice with 50 ml. portions of water. The combined aqueous acidic layers are extracted with 2×50 ml. ether. The combined etheral and benzene extracts are dried over sodium sulfate. Evaporation of solvent and fractionation of the residue through a 6" Vigreux column affords 89 g. (60%) of the product, ethyl-2-hydroxy-2-(p-methoxyphenyl)-1-methylpropionate, B.P. 165–160° (1.5 mm.).

(B) 6-Methoxy-2-methylindanone

By the method described in Vander Zanden, Rec. Trav. Chim., 68, 413 (1949), the compound from part A is converted to 6-methoxy-2-methylindanone.

Alternatively, the same compound can be obtained by adding α-methyl-β-(p-methoxylphenyl)propionic acid (15 g.) to 170 g. of polyphosphoric acid at 50° and heating the mixture at 83–90° for two hours. The syrup is poured into iced water. The mixture is stirred for one-half hour, and is extracted with ether (3×). The etheral solution is washed with water (2×) and 5% $NaHCO_3$ (5×) until all acidic material has been removed, and is dried over sodium sulfate. Evaporation of the solution gives 9.1 g. of the indanone as a pale yellow oil.

(C) (Z)-6-Methoxy-2-methyl-(4-pyridinylidene)-3-(N-benzyl)-indenylacetamide

In accordance with the procedures described in Example 1, parts D–G, this compound is obtained substituting 6-methoxy-2-methylindanone for 6-fluoro-2-methylindanone in part D of Example 1.

EXAMPLE 35

(Z)-5-Methoxy-2-Methyl-(4-Pyridinylidene)-3-(N-Benzyl)-Indenylacetamide (A) Ethyl 5-Methoxy-2-Methyl-3-Indenyl Acetate A solution of 13.4 g of 6-methoxy-2-methylindanone and 21 g. of ethyl bromoacetate in 45 ml. benzene is added over a period of five minutes to 21 g. of zinc amalgam (prepared according to Org. Syn. Coll. Vol. 3) in 110 ml. benzene and 40 ml. dry ether. A few crystals of iodine are added to start the reaction, and the reaction mixture is maintained at reflux temperature (ca. 65°) with external heating. At three-hour intervals, two batches of 10 g. zinc amalgam and 10 g. bromoester are added and the mixture is then refluxed for 8 hours. After addition of 30 ml. of ethanol and 150 ml. of acetic acid, the mixture is poured into 700 ml. of 50% aqueous acetic acid. The organic layer is separated, and the aqueous layer is extracted twice with ether. The combined organic layers are washed thoroughly with water, ammonium hydroxide and water. Drying over sodium sulfate, evaporation of solvent in vacuo followed by pumping at 80° (bath temperature)(1–2 mm.) gives crude ethyl-(1-hydroxy-2-methyl-6-methoxy-indenyl) acetate (ca. 18 g.).

A mixture of the above crude hydroxyester, 20 g. of p-toluenesulfonic acid monohydrate and 20 g. of anhydrous calcium chloride in 250 ml. toluene is refluxed overnight. The solution is filtered, and the solid residue is washed with toluene. The combined toluene solution is washed with water, sodium bicarbonate, water and then dried over sodium sulfate. After evaporation, the crude ethyl 5-methoxy-2-methyl-3-indenyl acetate is chromatographed on acid-washed alumina and the product is eluted with petroleum ether-ether (v./v. 50–100%) as a yellow oil (11.8 g., 70%).

(B) (Z)-5-Methoxy-2-methyl-(4-pyridinylidene)-3-(N-benzyl)-indenylacetamide

In accordance with the procedures described in Example 1, parts E–G, this compound is obtained substituting ethyl-5-methoxy-2-methyl-3-indenyl acetate for 5-fluoro-2-methindenyl-3-acetic acid in Example 1, part E.

EXAMPLE 36

(Z)-α-5-Methoxy-2-Methyl-(4-Pyridinylidene)-3-(N-Benzyl)-Indenylpropionamide (A) α-(5-Methoxy-2-methyl-3-indenyl)propionic acid The procedure of Example 35, part (A) is followed using ethyl α-bromopropionate in equivalent quantities in place of ethyl bromoacetate used therein. There is obtained ethyl α-(1-hydroxy-6-methoxy-2-methyl-1-indanyl)propionate, which is dehydrated to ethyl α-(5-methoxy-2-methyl-3-indenyl)propionate in the same manner.

The above ester is saponified to give α-(5-methoxy-2-methyl-3-indenyl)propionic acid.

(B) (Z)-α-5-Methoxy-2-methyl-(4-pyridinyl)-3-(N-benzyl)-α-methyl indenylpropionamide In accordance with the procedures described in Example 1, parts E–G, this compound is obtained substituting α-5-methoxy-2-methyl-3-indenyl)propionic acid for 5-fluoro-2-methylindenyl-3-acetic acid in Example 1, part E.

EXAMPLE 37

(Z) α-Fluoro-5-Methoxy-2-Methyl-(4-Pyridinylidene)-3-(N-Benzyl)Indenylacetamide (A) Methyl-5-Methoxy-2-Methyl-3-Indenyl-α-Fluoro Acetate A mixture of potassium fluoride (0.1 mole) and methyl-5-methoxy-2-methyl-3-indenyl-α-tosyloxy acetate (0.05 mole) in 200 ml. dimethylformamide is heated under nitrogen at the reflux temperature for 2–4 hours. The reaction mixture is cooled, poured into iced water and then extracted with ether. The ethereal solution is washed with water, sodium bicarbonate and dried over sodium sulfate. Evaporation of the solvent and chromatography of the residue on an acid-washed alumina column (300 g.) using ether-petroleum ether (v./v. 20–50%) as eluent give the product, methyl-5-methoxy-2-methyl-3-indenyl-α-fluoroacetate.

(B) (Z) α-Fluoro-5-methoxy-2-methyl-(4-pyridinylidene)-3-(N-benzyl)indenylacetamide In accordance with the procedures described in Example 1 above, parts E–G, this compound is obtained substituting methyl-5-methoxy-2-methyl-3-indenyl-α-fluoroacetate for 5-fluoro-2-methylindenyl-3-acetic acid in Example 1 above, part E.

For the introduction of the =CH—Y part in Scheme III, any of the appropriate heterocyclic aldehydes may be used either directly in the base-catalyzed condensation or in a Wittig reaction in an alternative route. The aldehydes that may be used are listed in Table A below:

TABLE A pyrrol-2-aldehyde*
pyrimidine-2-aldehyde
6-methylpyridine-2-aldehyde*
1-methylbenzimidazole-2-aldehyde
isoquinoline-4-aldehyde
4-pyridinecarboxaldehyde*
3-pyridinecarboxaldehyde*
2-pyridinecarboxaldehyde*
4,6-dimethyl-2-pyridinecarboxaldehyde*
4-methyl-pyridinecarboxaldehyde*
4-quinolinecarboxaldehyde*
3-quinolinecarboxaldehyde*
2-quinolinecarboxaldehyde*
2-chloro-3-quinolinecarboxaldehyde*
pyrazinealdehyde
(Prepared as described by Rutner et al., JOC 1963, 28, 1898–99)
pyridazine-3-aldehyde
(Prepared as described by Heinisch et al., Monatshefte Fuer Chemie 108, 213–224, 1977)
pyrimidine-4-aldehyde
(Prepared as described by Bredereck et al., Chem. Ber. 1964, 97, 3407–17)
2-methyl-pyrimidine-4-aldehyde
(Prepared as described by Bredereck et al., Chem. Ber. 1964, 97, 3407–17)
pyridazine-4-aldehyde
(Prepared as described by Heinisch et al., Monatshefte Fuer Chemie 104, 1372–1382 (1973))
1-methylindole-3-carboxaldehyde*
1-acetyl-3-indolecarboxaldehyde*

*Available from Aldrich

Available from Aldrich

The aldehydes above can be used in the reaction schemes above in combination with various appropriate amines to produce compounds with the scope of this invention. Examples of appropriate amines are those listed in Table B below:

TABLE B benzylamine
2,4-dimethoxybenzylamine
2-methoxybenzylamine
2-fluorobenzylamine
4-dimethylaminobenzylamine
4-sulfonaminobenzylamine
1-phenylethylamine (R-enantiomer)
2-amino-2-phenylethanol (S-enantiomer)
2-phenylglycinonitrile (S-enantiomer)

EXAMPLE 38

(Z)-5-Fluoro-2-Methyl-(4-Pyridylidene)-3-(N-Benzyl)Indenylacetamide Hydrochloride (Z)-5-Fluoro-2-methyl-(4-pyridylidene)-3-(N-benzyl)indenylacetamide (1396 g; MW 384.45; 3.63 mol) from Example 1 is dissolved at 45° C. in ethanol (28 L). Aqueous HCl (12 M; 363 mL) is added stepwise. The reaction mixture is heated under reflux for 1 hour, is allowed to cool to room temperature, then stored at −10° C. for 3 hours. The resulting solid is filtered off, is washed with ether (2×1.5 L) and is air-dried overnight. Drying under vacuum at 70° C. for 3 days gives (Z)-5-fluoro-2-methyl-(4-pyridylidene)-3-(N-benzyl)indenylacetamide hydrochloride with a melting point of 207–209° C. ($R_1$=F, $R_2$=$CH_3$, $R_3$=H, $R_4$=H, $R_5$=H, $R_6$=H, $R_7$=H, n=1, m=1, Y=4-pyridinyl.hydrochloride). Yield: 1481 g (97%; 3.51 mol); MW: 420.91 g/mol. This compound is also known as CP461.

$^1$H-NMR (DMSO-$d_6$): 2.18 (s, 3, =C—$CH_3$); 3.54 (s,2, =$CH_2$CO); 4.28 (d, 2, $NCH_2$); 6.71 (m, 1, ar.); 7.17 (m, 8, ar.); 8.11 (d, 2, ar., AB system); 8.85 (m, 1, NH); 8.95 (d, 2, ar., AB system); IR (KBr): 3432 NH; 1635 C=O; 1598 C=C.

Experimental Results

A number of compounds were examined in the various protocols and screened for potential use in treating neoplasia. The results of these tests are reported below. The test compounds are hereinafter designated by a letter code that corresponds to the following:

A - rac-threo-(E)-1-(N,N'-diethylaminoethanethio)-1-(butan-1',4'-olido)-[3',4':1,2]-6-fluoro-2-methyl-3-(p-methylsulfonylbenzylidene)-indan;
B - (Z)-5-Fluoro-2-methyl-1-(3,4,5-trimethoxybenzylidene)-3-acetic acid;
C - (Z)-5-Fluoro-2-methyl-1-(p-chlorobenzylidene)-3-acetic acid;
D - rac-(E)-1-(butan-1',4'-olido)-[3',4':1,2]-6-fluoro-2-methyl-3-(p-methylsulfonylbenzylidene)-1S-indanyl-N-acetylcysteine;
E - (Z)-5-Fluoro-2-methyl-1-(3,4,5-trimethoxybenzylidene)-3-indenylacetamide, N-benzyl;
F - (Z)-5-Fluoro-2-methyl-1-(p-methylsulfonylbenzylidene)-3-indenylacetamide, N,N'-dicyclohexyl;
G - ribo-(E)-1-Triazolo-[2',3':1",3"]-1-(butan-1',4'-olido)-[3',4':1,2]-6-fluoro-2-methyl-3-(p-methylsulfonylbenzylidene)-indan; and
H - rac-(E)-1-(butan-1',4'-olido)-[3',4':1,2]-6-fluoro-2-methyl-3-(p-methylsulfonylbenzylidene)-1S-indanyl-glutathione).

Experimental Example 1

COX Inhibition Assay

Figure 4:
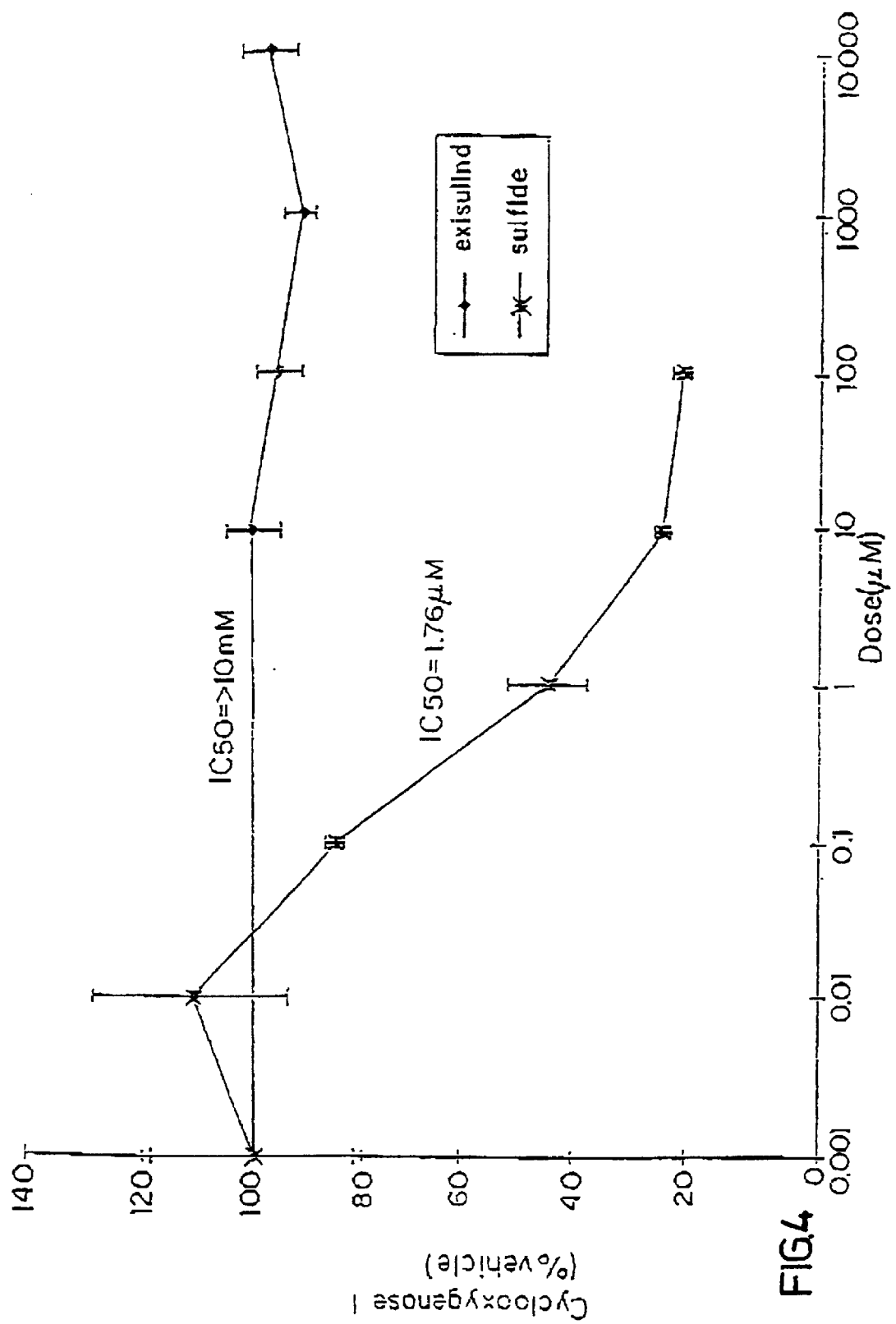
FIG. 4 illustrates the effect of the sulfide derivative of sulindac and the sulfone derivative of sulindac (a.k.a. exisulind) on purified cyclooxygenase activity.

Reference compounds and test compounds were analyzed for their COX inhibitory activity in accordance with the protocol for the COX assay, supra. FIG. 4 shows the effect of various concentrations of either sulindac sulfide or exisulind on purified cyclooxygenase (Type 1) activity. Cyclooxygenase activity was determined using purified cyclooxygenase from ram seminal vesicles as described previously (Mitchell et al, supra). The $IC_{50}$ value for sulindac sulfide was calculated to be approximately 1.76 $\mu$M, while that for exisulind was greater than 10,000 $\mu$M. These data show that sulindac sulfide, but not exisulind, is a COX-I inhibitor. Similar data were obtained for the COX-2 isoenzyme (Thompson, et al., Journal of the National Cancer Institute, 87: 1259–1260, 1995).

Figure 5:
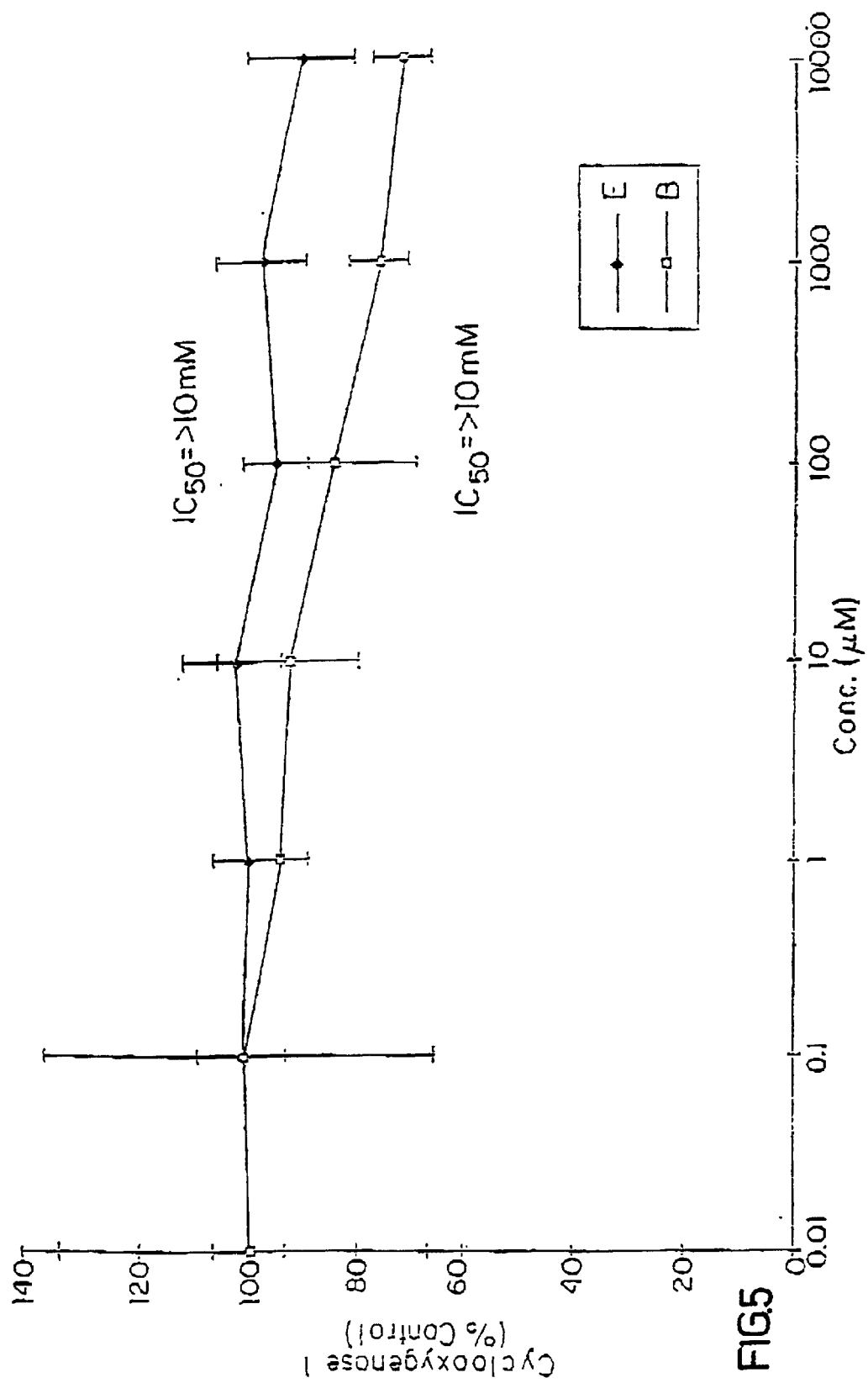
FIG. 5 illustrates the effects of test compounds B and E on COX inhibition.

FIG. 5 shows the effect of test compounds B and E on COX inhibition. COX activity was determined as for the compounds shown in FIG. 4. The data show that neither test compound B and E significantly inhibits COX-I.

TABLE 2

Cyclooxygenase inhibitory activity for a series of compounds

| Reference compounds | % Inhibition at 100 $\mu$M |
|---|---|
| Indomethacin | 95 |
| MY5445 | 94 |
| Sulindac sulfide | 97 |
| Exisulind | <25 |

| Test compounds | % Inhibition at 100 $\mu$M |
|---|---|
| A | <25 |
| B | <25 |
| C | 87 |
| D | <25 |
| E | <25 |

In accordance with the protocol, supra, compounds A through E were evaluated for COX inhibitory activity as reported in Table 2 above. Compound C was found to inhibit COX greater than 25% at a 100 $\mu$M dose, and therefore, would not be selected for further screening.

Experimental Example 2 cGMP PDE Inhibition Assay

Figure 6:
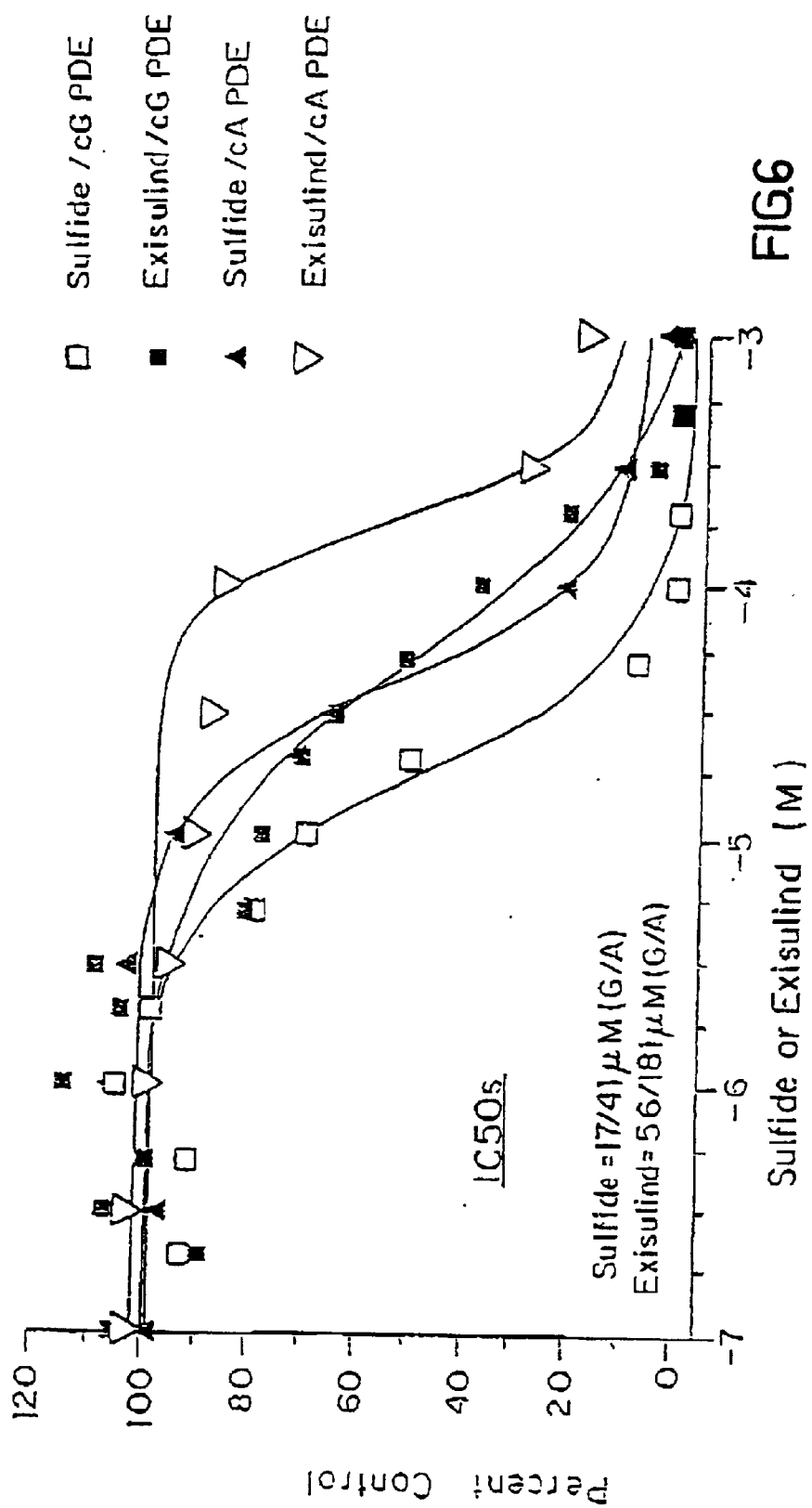
FIG. 6 illustrates the inhibitory effects of sulindac sulfide and exisulind on PDE4 and PDE5 purified from cultured tumor cells.

Reference compounds and test compounds were analyzed for their cGMP PDE inhibitory activity in accordance with the protocol for the assay described supra. FIG. 6 shows the effect of various concentrations of sulindac sulfide and exisulind on either PDE4 or cGMP PDE activity purified from human colon HT-29 cultured tumor cells, as described previously (W. J. Thompson et al., supra). The $IC_{50}$ value of sulindac sulfide for inhibition of PDE4 was 41 $\mu$M, and for inhibition of cGMP PDE was 17 $\mu$M. The $IC_{50}$ value of exisulind for inhibition of PDE4 was 181 $\mu$M, and for inhibition of cGMP PDE was 56 $\mu$M. These data show that both sulindac sulfide and exisulind inhibit phosphodiesterase activity. Both compounds show selectivity for the cGMP PDE isoenzyme forms over PDE4 isoforms.

Figure 7A:
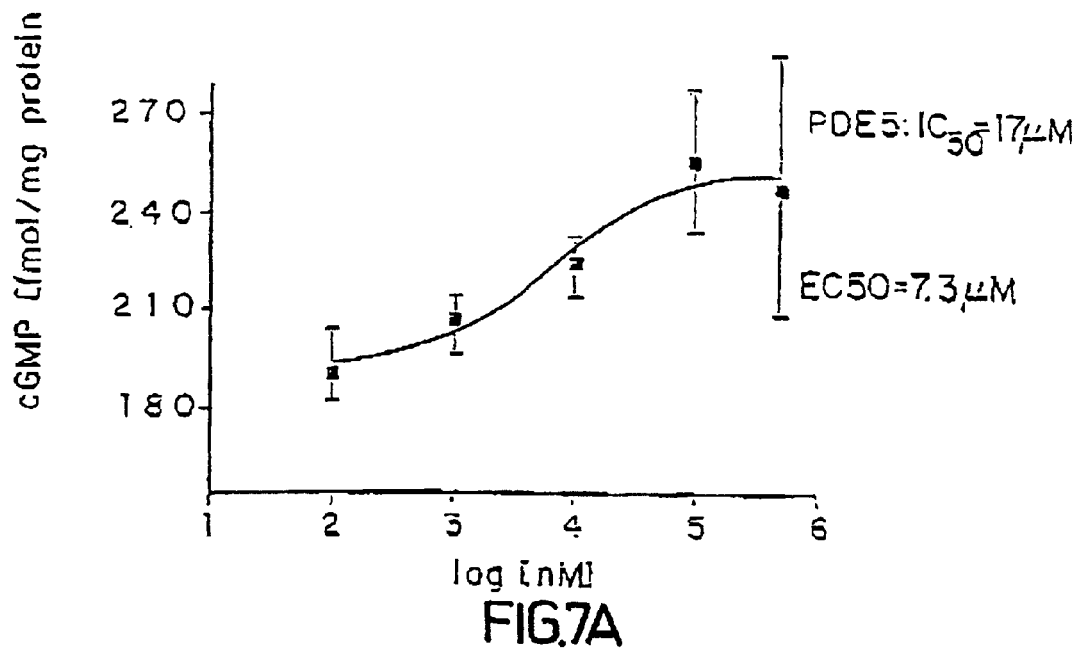
FIGS. 7A and 7B illustrate the effects of sulindac sulfide on cyclic nucleotide levels in HT-29 cells.
Figure 7B:
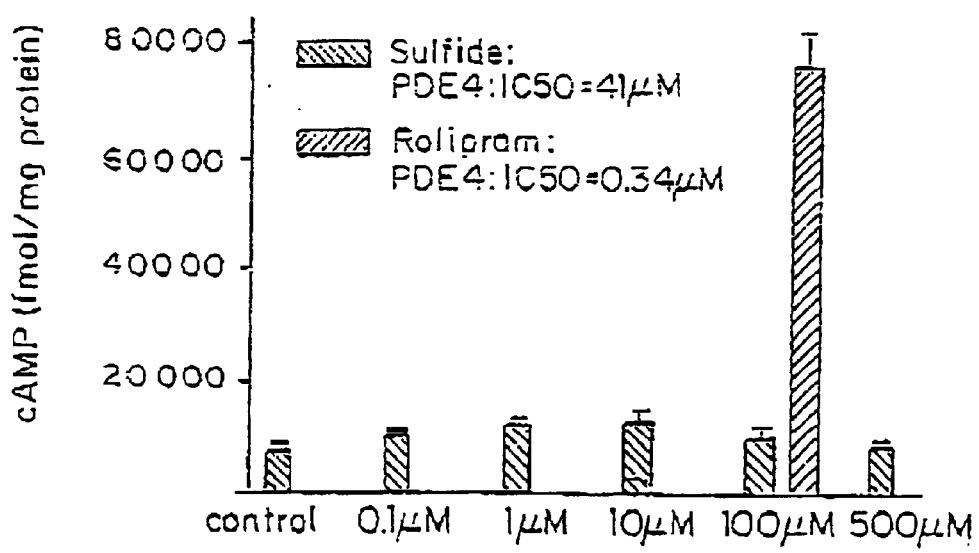

FIG. 7 shows the effects of sulindac sulfide on either cGMP or cAMP production as determined in cultured HT-29 cells in accordance with the assay described, supra. HT-29 cells were treated with sulindac sulfide for 30 minutes and cGMP or cAMP was measured by conventional radioimmunoassay method. As indicated, sulindac sulfide increased the levels of cGMP by greater than 50% with an $EC_{50}$ value of 7.3 $\mu$M (FIG. 7A). Levels of cAMP were unaffected by treatment, although a known PDE4 inhibitor, rolipram, increased cAMP (FIG. 7B). The data demonstrate the pharmacological significance of inhibiting cGMP PDE, relative to PDE4.

Figure 8:
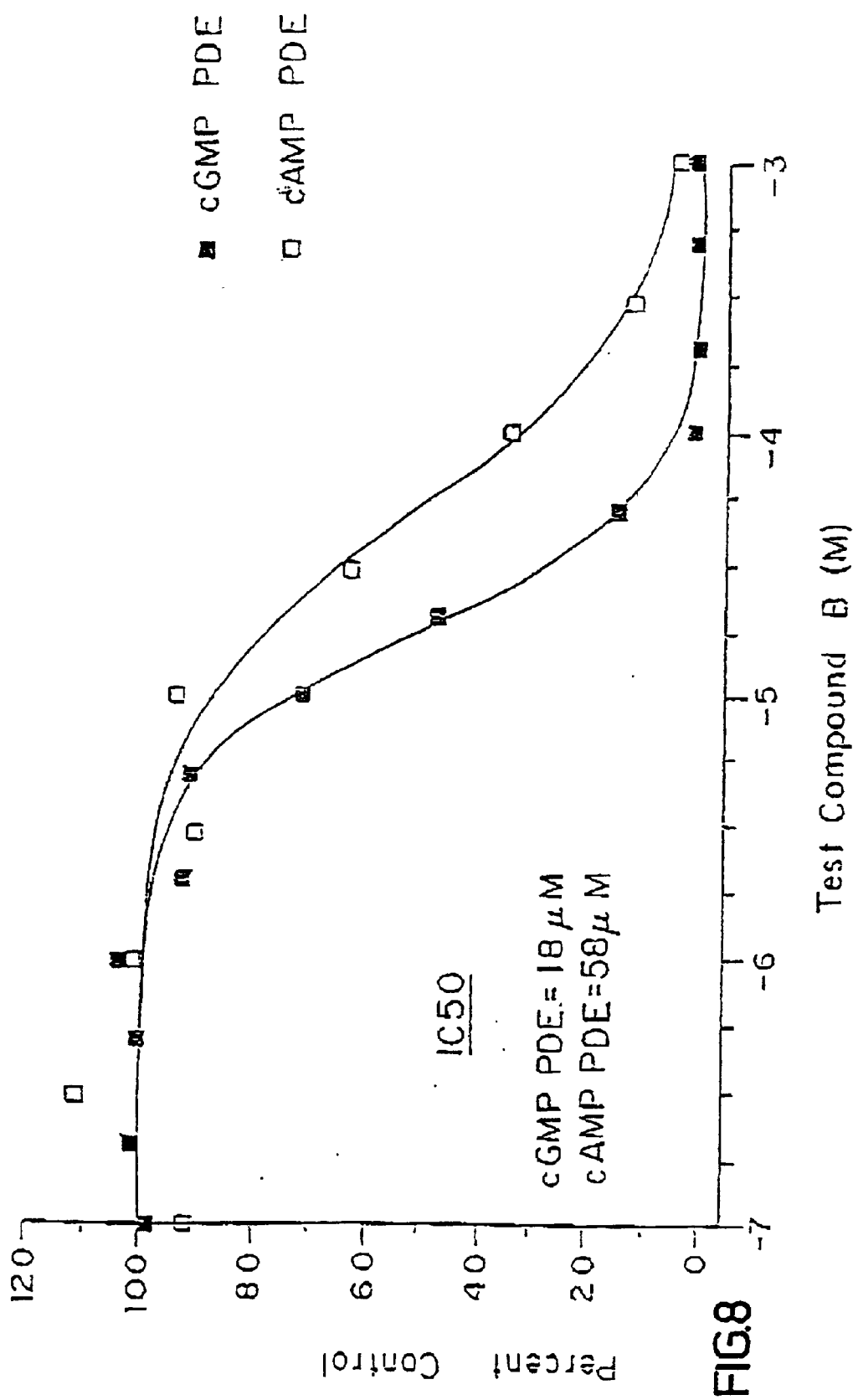
FIG. 8 illustrates the phosphodiesterase inhibitory activity of compound B.

FIG. 8 shows the effect of the indicated dose of test compound B on either cGMP PDE or PDE4 isozymes of phosphodiesterase. The calculated $IC_{50}$ value was 18 $\mu$M for cGMP PDE and was 58 $\mu$M for PDE4.

Figure 9:
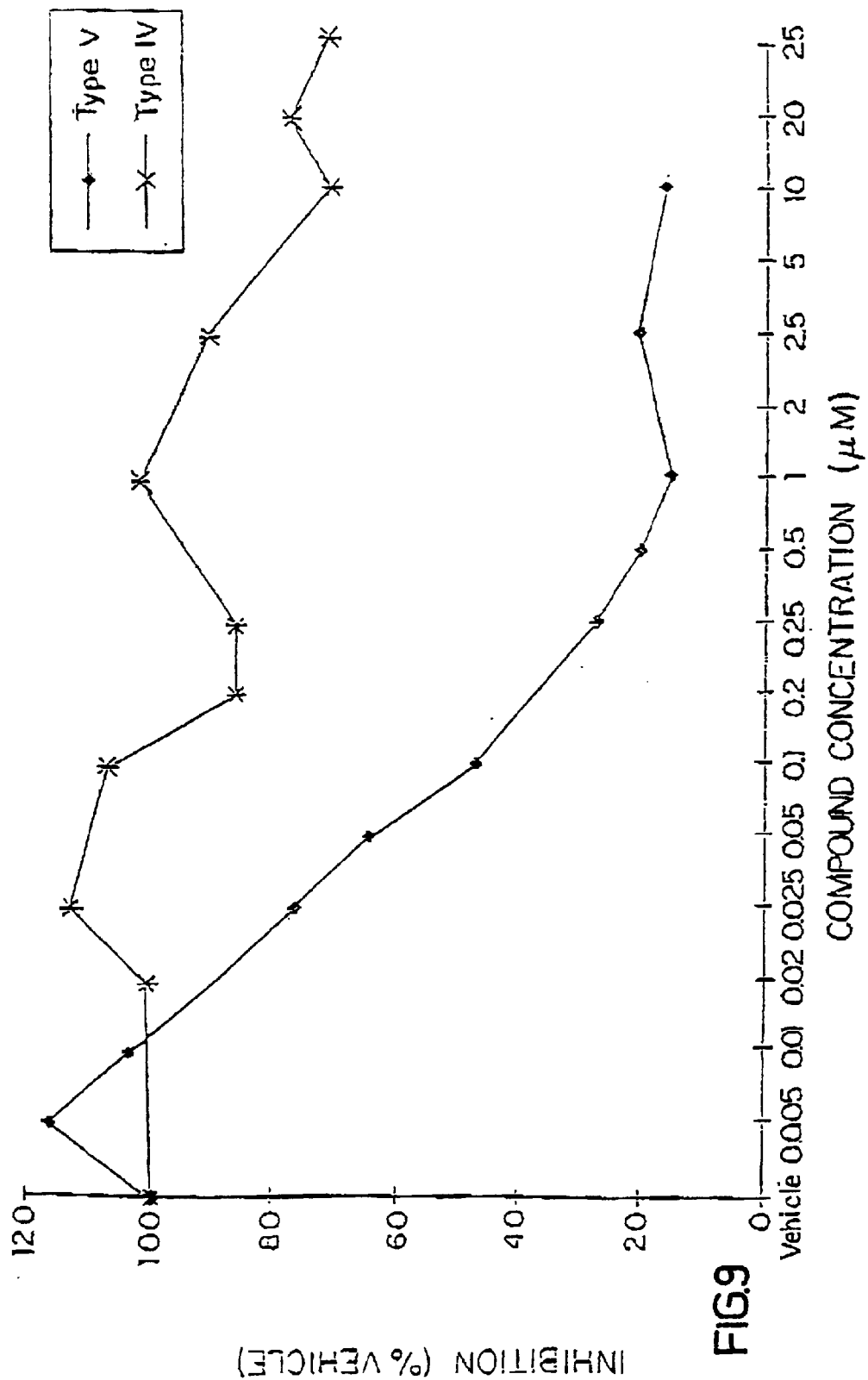
FIG. 9 illustrates the phosphodiesterase inhibitory activity of compound E.

FIG. 9 shows the effect of the indicated dose of test compound E on either PDE4 or cGMP PDE. The calculated $IC_{50}$ value was 0.08 $\mu$M for cGMP PDE and greater than 25 $\mu$M for PDE4.

TABLE 3 cGMP PDE inhibitory activity among a series of compounds

| Reference compounds | % Inhibition at 10 $\mu$M |
|---|---|
| Indomethacin | 34 |
| MY5445 | 86 |
| Sulindac sulfide | 97 |
| Exisulind | 39 |

| Test compounds | % Inhibition at 10 $\mu$M |
|---|---|
| A | <25 |
| B | <25 |
| C | <25 |
| D | 36 |
| E | 75 |

The above compounds in Table 3 were evaluated for PDE inhibitory activity, as described in the protocol supra. Of the compounds that did not inhibit COX, only compound E was found to cause greater than 50% inhibition at 10 $\mu$M. As noted in FIG. 8, compound B showed inhibition of greater than 50% at a dose of 20 $\mu$M. Therefore, depending on the dosage level used in a single dose test, some compounds may be screened out that otherwise may be active at slightly higher dosages. The dosage used is subjective and may be lowered after active compounds are found at certain levels to identify even more potent compounds.

Experimental Example 3

Apoptosis Assay

Reference compounds and test compounds were analyzed for their novel PDE inhibitory activity in accordance with the protocols for the assay, supra. In accordance with those protocols, FIG. 10 shows the effects of sulindac sulfide and exisulind on apoptotic and necrotic cell death. HT-29 cells were treated for six days with the indicated dose of either sulindac sulfide or exisulind. Apoptotic and necrotic cell death was determined previously (Duke and Cohen, In: Current Protocols in Immunology, 3.17.1–3.17.16, New York, John Wiley and Sons, 1992). The data show that both sulindac sulfide and exisulind are capable of causing apoptotic cell death without inducing necrosis. All data were collected from the same experiment.

Figure 11A:
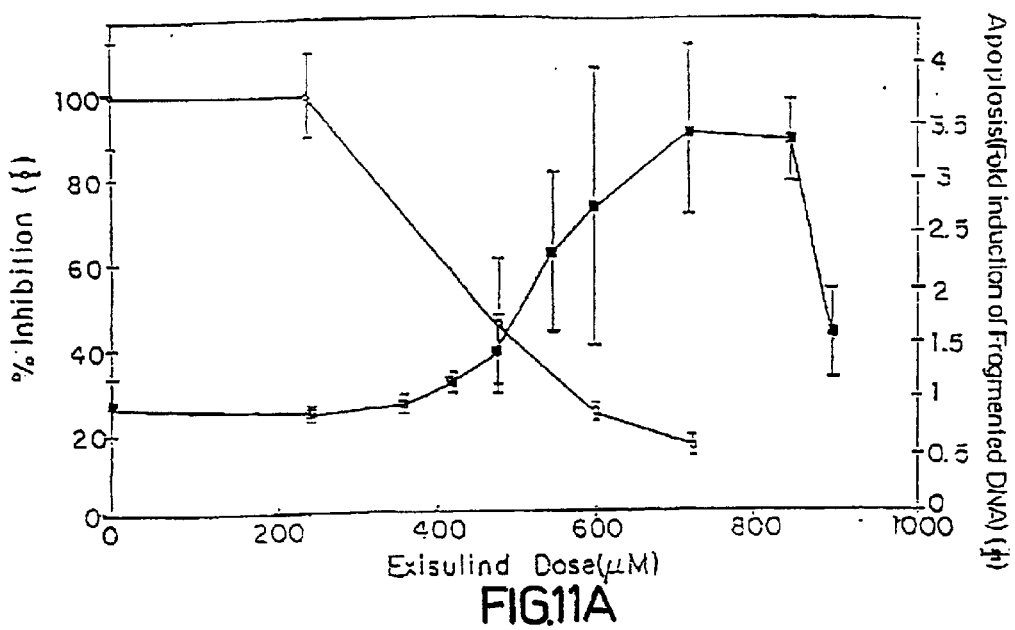
FIGS. 11A and 11B illustrate the effects of sulindac sulfide and exisulind on HT-29 cell growth inhibition and apoptosis induction as determined by DNA fragmentation.
Figure 11B:
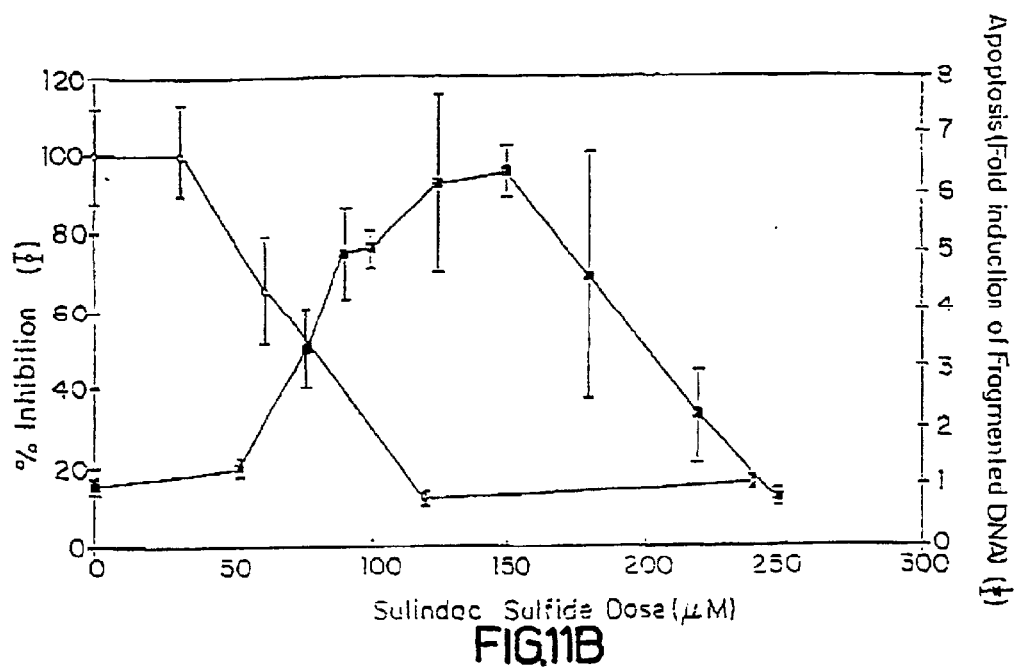

FIG. 11 shows the effect of sulindac sulfide and exisulind on tumor growth inhibition and apoptosis induction as determined by DNA fragmentation. Top FIG. (11A); growth inhibition (open symbols, left axis) and DNA fragmentation (closed symbols, right axis) by exisulind. Bottom FIG. (11B); growth inhibition (open symbols) and DNA fragmentation (closed symbols) by sulindac sulfide. Growth inhibition was determined by the SRB assay after six days of treatment. DNA fragmentation was determined after 48 hours of treatment. All data were collected from the same experiment.

Figure 12:
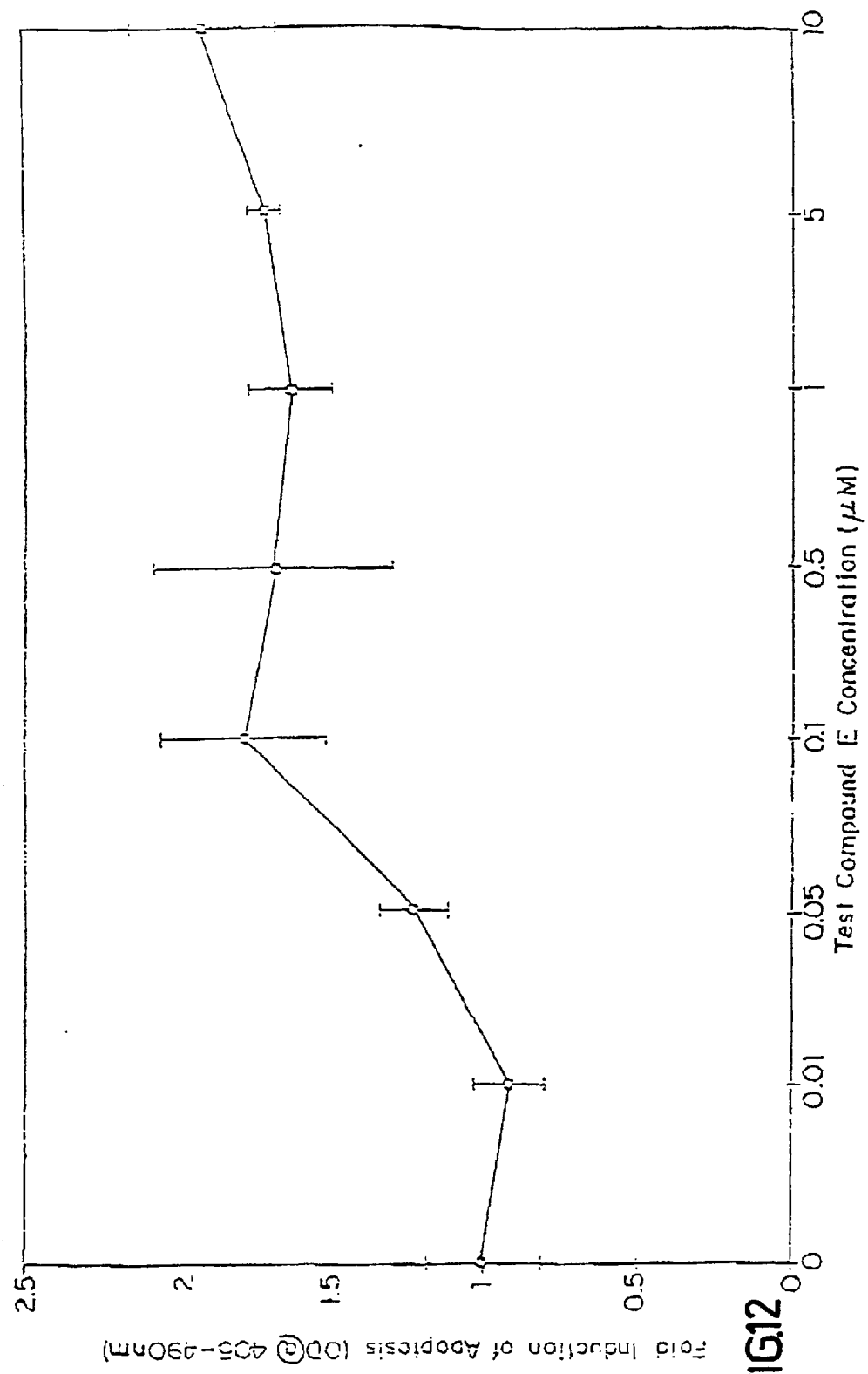
FIG. 12 illustrates the apoptosis-inducing properties of compound E.

FIG. 12 shows the apoptosis inducing properties of compound E. HT-29 colon adenocarcinoma cells were treated with the indicated concentration of compound E for 48 hours and apoptosis was determined by the DNA fragmentation assay. The calculated $EC_{50}$ value was 0.05 μM.

Figure 13:
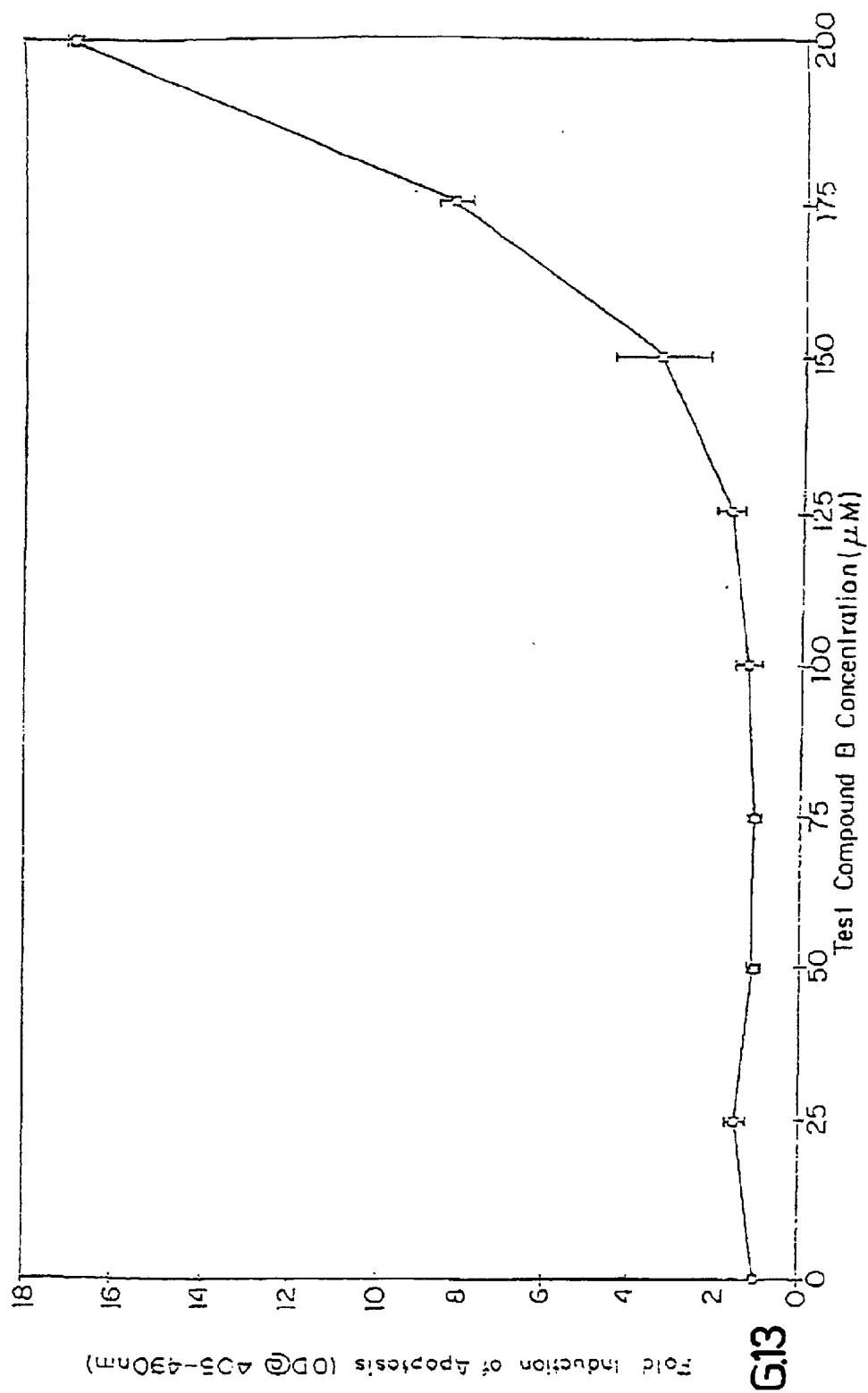
FIG. 13 illustrates the apoptosis-inducing properties of compound B.

FIG. 13 shows the apoptosis inducing properties of compound B. HT-29 colon adenocarcinoma cells were treated with the indicated concentration of compound B for 48 hours and apoptosis was determined by the DNA fragmentation assay. The calculated $EC_{50}$ value was approximately 175 μM.

TABLE 4

Apoptosis-inducing activity among a series of compounds

| Reference compounds | Fold induction at 100 μM |
|---|---|
| Indomethacin | <2.0 |
| MY5445 | 4.7 |
| Sulindac sulfide | 7.9 |
| Exisulind | <2.0 |
| E4021 | <2.0 |
| Zaprinast | <2.0 |
| Sildenafil | <2.0 |
| EHNA | <2.0 |

| Test compounds | Fold induction at 100 μM |
|---|---|
| A | <2.0 |
| B | 3.4 |
| C | 5.6 |
| D | <2.0 |
| E | 4.6 |

In accordance with the fold induction protocol, supra, the compounds A through E were tested for apoptosis inducing activity, as reported in Table 4 above. Compounds B, C and E showed significant apoptotic inducing activity, greater than 2.0 fold, at a dosage of 100 μM. Of these three compounds, at this dosage only B and E did not inhibit COX but did inhibit cGMP-specific PDE.

The apoptosis inducing activity for a series of phosphodiesterase inhibitors was determined. The data are presented in Table 5 below. HT-29 cell were treated for 6 days with various inhibitors of phosphodiesterase. Apoptosis and necrosis were determined morphologically after acridine orange and ethidium bromide labeling in accordance with the assay described, supra. The data show that the novel cGMP-specific PDE is useful for screening compounds that induce apoptosis of HT-29 cells.

TABLE 5

Apoptosis-Induction Data for PDE Inhibitors

| Inhibitor | Reported Selectivity | % Apoptosis | % Necrosis |
|---|---|---|---|
| Vehicle | | 8 | 6 |
| 8-methoxy-IBMX | PDE1 | 2 | 1 |
| Milrinone | PDE3 | 18 | 0 |
| RO-20-1724 | PDE4 | 11 | 2 |
| MY5445 | PDE5 | 80 | 5 |
| IBMX | Non-selective | 4 | 13 |

Experimental Example 4

Growth Inhibition Assay

Figure 14:
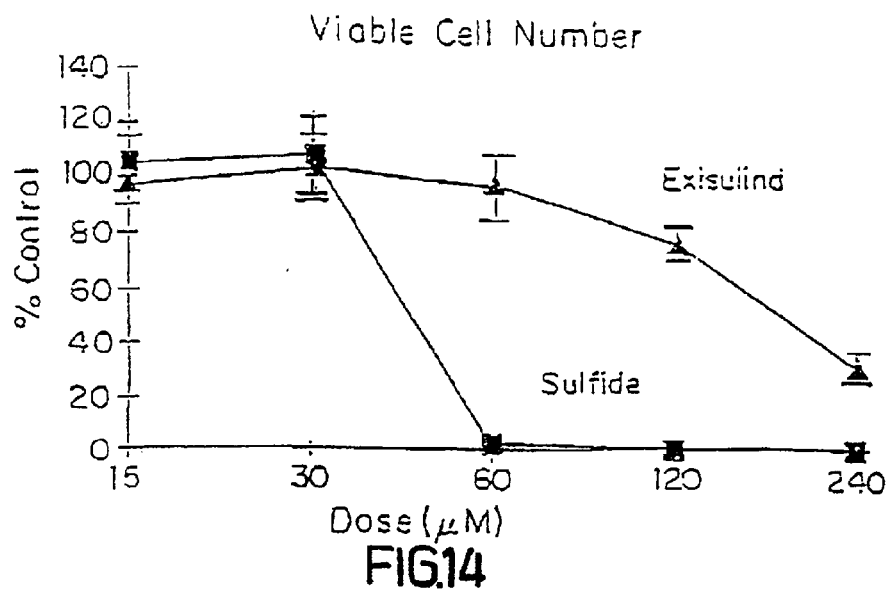
FIG. 14 illustrates the effects of sulindac sulfide and exisulind on tumor cell growth.

Reference compounds and test compounds were analyzed for their PDE5 inhibitory activity in accordance with the protocol for the assay supra. FIG. 14 shows the inhibitory effect of various concentrations of sulindac sulfide and exisulind on the growth of HT-29 cells. HT-29 cells were treated for six days with various doses of exisulind (triangles) or sulindac sulfide (squares) as indicated. Cell number was measured by a sulforhodamine assay as previously described (Piazza et al., Cancer Research, 55: 3110–3116, 1995). The $IC_{50}$ value for sulindac sulfide was approximately 45 μM and 200 μM for exisulind. The data show that both sulindac sulfide and exisulind are capable of inhibiting tumor cell growth.

Figure 15A:
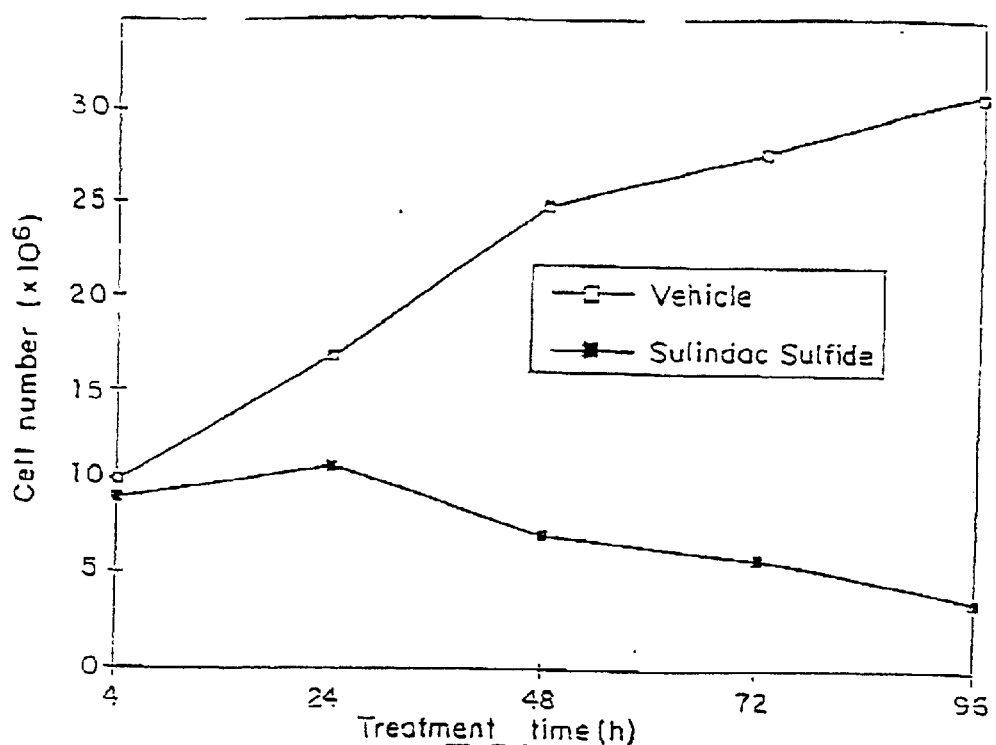
FIGS. 15A and 15B illustrate the growth inhibitory and apoptosis-inducing activity of sulindac sulfide and control (DMSO).
Figure 15B:
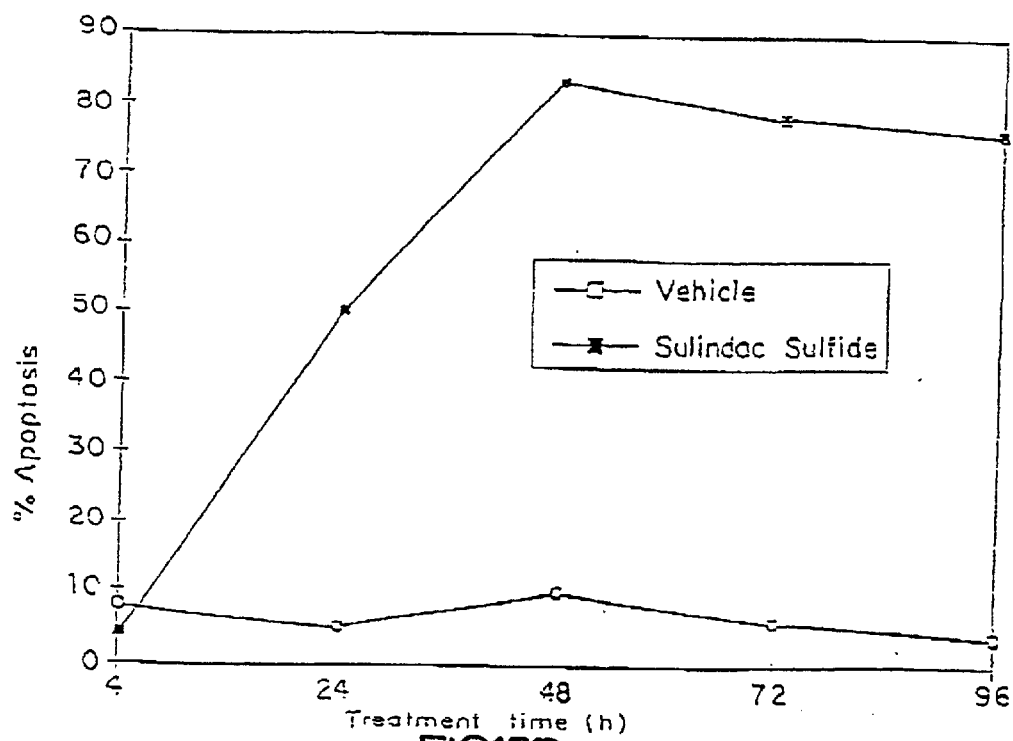

FIG. 15 shows the growth inhibitory and apoptosis-inducing activity of sulindac sulfide. A time course experiment is shown involving HT-29 cells treated with either vehicle, 0.1% DMSO (open symbols) or sulindac sulfide, 120 μM (closed symbols). Growth inhibition (15A top) was measured by counting viable cells after trypan blue staining. Apoptosis (15B bottom) was measured by morphological determination following staining with acridine orange and ethidium bromide as described previously (Duke and Cohen, in: Current Protocols in Immunology, 3.17.1–3.17.16, New York, John Wiley and Sons, 1992). The data demonstrate that sulindac sulfide is capable of inhibiting tumor cell growth, and that the effect is accompanied by an increase in apoptosis. All data were collected from the same experiment.

Figure 16:
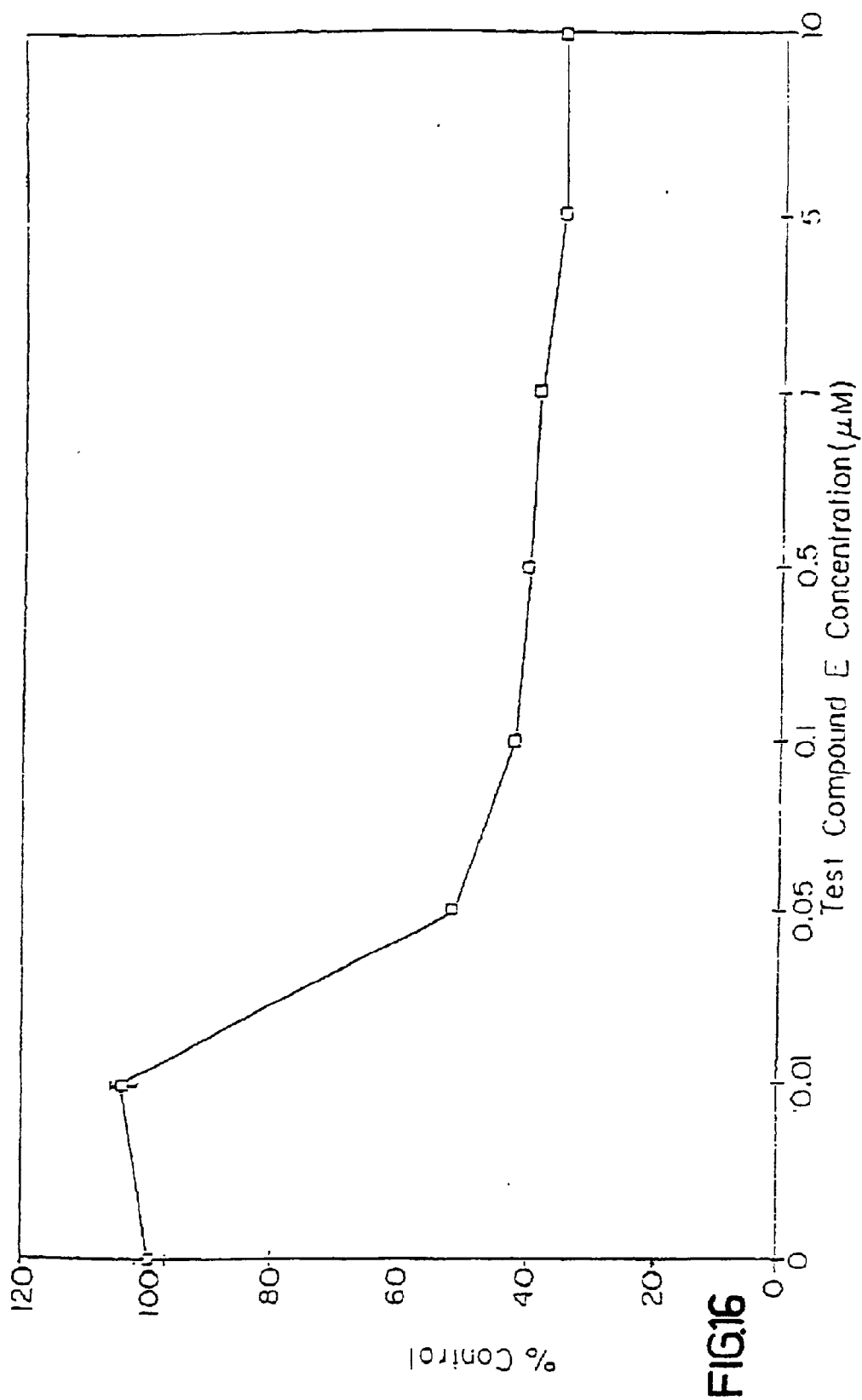
FIG. 16 illustrates the growth inhibitory activity of compound E.

FIG. 16 shows the growth inhibitory activity of test compound E. HT-29 colon adenocarcinoma cells were treated with the indicated concentration of compound E for six days and cell number was determined by the SRB assay. The calculated $IC_{50}$ value was 0.04 μM.

TABLE 6

Growth-inhibitory activity among a series of compounds

| Reference compounds | % Inhibition at 100 μM |
|---|---|
| Indomethacin | 75 |
| MY5445 | 88 |
| Sulindac sulfide | 88 |
| Exisulind | <50 |
| E4021 | <50 |
| sildenafil | <50 |
| zaprinast | <50 |

| Test compounds | % Inhibition at 100 μM |
|---|---|
| A | 68 |
| B | 77 |
| C | 80 |
| D | 78 |
| E | 62 |

In accordance with the screening protocol of section supra, compounds A through E were tested for growth inhibitory activity, as reported in Table 6 above. All the test compounds showed activity exceeding a 100 μM single dose test.

The growth inhibitory activity for a series of phosphodiesterase inhibitors was determined. The data are shown in Table 7 below. HT-29 cells were treated for 6 days with various inhibitors of phosphodiesterase. Cell growth was determined by the SRB assay described, supra. The data below taken with those above show that inhibitors of the novel PDE were effective for inhibiting tumor cell growth.

TABLE 7

Growth Inhibitory Data for PDE Inhibitors

| Inhibitor | Reported Selectivity | Growth inhibition ($IC_{50}$, $\mu M$) |
|---|---|---|
| 8-methoxy-IBMX | PDE1 | >200 $\mu M$ |
| Milrinone | PDE3 | >200 $\mu M$ |
| RO-20-1724 | PDE4 | >200 $\mu M$ |
| MY5445 | PDE5 | 5 $\mu M$ |
| IBMX | Non-selective | >100 $\mu M$ |
| Zaprinast | PDE5 | >100 $\mu M$ |
| Sildenafil | PDE5 | >100 $\mu M$ |
| E4021 | PDE5 | >100 $\mu M$ |

To show the effectiveness of this screening method on various forms of neoplasia, compounds were tested on numerous cell lines. The effects of sulindac sulfide and exisulind on various cell lines were determined. The data are shown in Table 8 below. The $IC_{50}$ values were determined by the SRB assay. The data show the broad effectiveness of these compounds on a broad range of neoplasias, with effectiveness at comparable dose range. Therefore, compounds identified and selected by this invention should be useful for treating multiple forms of neoplasia.

TABLE 8

Growth Inhibitory Data of Various Cell Lines

| Cell Type/Tissue specificity | $IC_{50}$ ($\mu M$) Sulindac sulfide | Exisulind | Compound E* |
|---|---|---|---|
| HT-29, Colon | 60 | 120 | 0.10 |
| HCT116, Colon | 45 | 90 | |
| MCF7/S, Breast | 30 | 90 | |
| UACC375, Melanoma | 50 | 100 | |
| A-427, Lung | 90 | 130 | |
| Bronchial Epithelial Cells | 30 | 90 | |
| NRK, Kidney (non ras-transformed) | 50 | 180 | |
| KNRK, Kidney (ras transformed) | 60 | 240 | |
| Human Prostate Carcinoma PC3 | | 82 | 0.90 |
| Colo 205 | | | 1.62 |
| DU-145 | | | 0.10 |
| HCT-15 | | | 0.60 |
| MDA-MB-231 | | | 0.08 |
| MDA-MB-435 | | | 0.04 |

*Determined by neutral red assay as described by Schmid et al., in Proc. AACR Vol 39, p. 195 (1998).

Experimental Example 5

Activity in Mammary Gland Organ Culture Model

Figure 17:
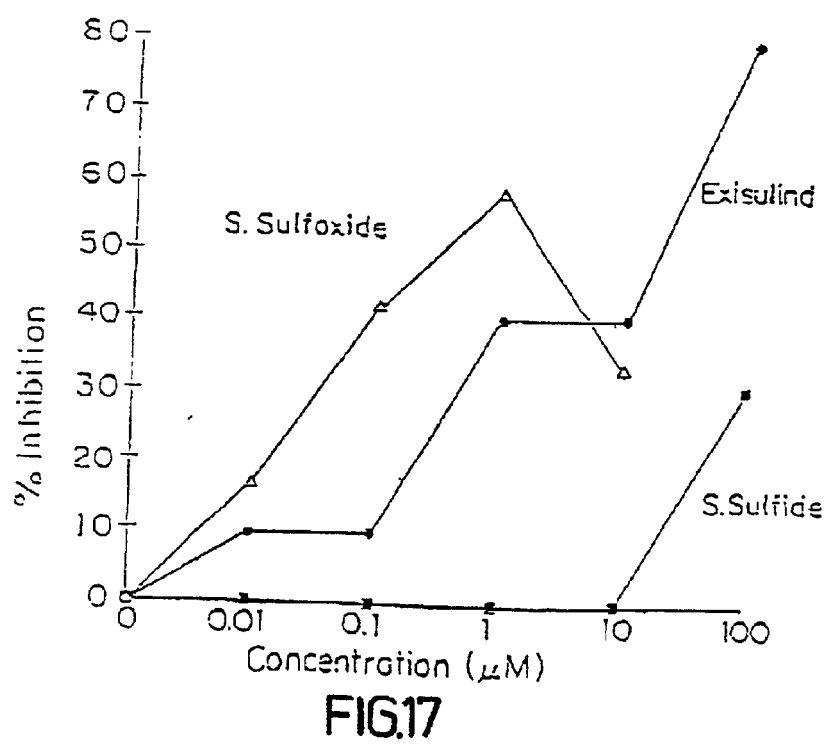
FIG. 17 illustrates the inhibition of pre-malignant, neoplastic lesions in mouse mammary gland organ culture by sulindac metabolites.

FIG. 17 shows the inhibition of premalignant lesions in mammary gland organ culture by sulindac metabolites. Mammary gland organ culture experiment were performed as previously described (Mehta and Moon, *Cancer Research*, 46: 5832–5835, 1986). The results demonstrate that sulindac and exisulind effectively inhibit the formation of premalignant lesions, while sulindac sulfide was inactive.

The data support the hypothesis that cyclooxygenase inhibition is not necessary for the anti-neoplastic properties of desired compounds.

Analysis

To select compounds for treating neoplasia, this invention provides a rationale for comparing experimental data of test compounds from several protocols. Within the framework of this invention, test compounds can be ranked according to their potential use for treating neoplasia in humans. Those compounds having desirable effects may be selected for additional testing and subsequent human use.

Qualitative data of various test compounds and the several protocols are shown in Table 9 below. The data show that exisulind, compound B and compound E exhibit the appropriate activity to pass the screen of four assays: lack of COX inhibition, and presence of effective cGMP-specific PDE inhibition, growth inhibition and apoptosis induction. The activity of these compounds in the mammary gland organ culture validates the effectiveness of this invention. The qualitative valuations of the screening protocols rank compound E best, then compound B and then exisulind.

TABLE 9

Activity Profile of Various Compounds

| Compound | COX Inhibition | PDE Inhibition | Growth Inhibition | Apoptosis | Mammary Gland Organ Culture |
|---|---|---|---|---|---|
| Exisulind | − | + + | + + | + + | + + + |
| Sulindac sulfide | + + + + | + + + | + + + | + + + | − |
| MY5445 | + + + + | + + + | + + + | + + + | + |
| A | − | − | + + + | + + | + + |
| B | − | + + + | + + + | + + + | + + |
| D | − | − | + + | − | − |
| E | − | + + + + | + + + + | + + + + | + + + + |
| F | − | − | + + | + | − |
| G | − | − | + + + | + + | + + + |
| H | − | − | + + | − | − |

Table 9 Code: Activity of compounds based on evaluating a series of experiments involving tests for maximal activity and potency.
− Not active
+ Slightly active
+ + Moderately active
+ + + Strongly active
+ + + + Highly active Also disclosed is a novel assay for PKG activity, which is used in the screening methods of this invention, but also has more general usefulness in assaying for PKG activity for other purposes (e.g., for studying the role of PKG in normal cellular function). For explanation purposes, it is useful to describe the PKG assay first, before describing how PKG activity can be useful in drug evaluation in ascertaining whether a compound is potentially useful in the treatment of neoplasia.

The Novel PKG Assay

The novel PKG assay of this invention involves binding to solid phase plural amino acid sequences, each of which contain at least the cGMP-binding (cGB) domain and the phosphorylation site of phosphodiesterase type 5 ("PDE5"). That sequence is known and described in the literature below. Preferably, the bound PDE5 sequence does not include the catalytic domain of PDE5 as described below. One way to bind the PDE5 sequences to a solid phase is to express those sequences as a fusion protein of the PDE5 sequence and one member of an amino acid binding pair, and chemically link the other member of that amino acid binding pair to a solid phase (e.g., beads). One binding pair that can be used is glutathione S-transferase ("GST") and glutathione ("GSH"), with the GST being expressed as a fusion protein with the PDE5 sequence described above, and the GSH bound covalently to the solid phase. In this fashion, the PDE5 sequence/GST fusion protein can be bound to a solid phase simply by passing a solution containing the fusion protein over the solid phase, as described below.

RT-PCR method is used to obtain the cGB domain of PDE5 with forward and reverse primers designed from bovine PDE5A cDNA sequence (McAllister-Lucas L. M. et al, *J. Biol. Chem.* 268, 22863–22873, 1993) and the selection among PDE 1–10 families. 5'-3', Inc. kits for total RNA followed by oligo (dT) column purification of mRNA are used with HT-29 cells. Forward primer (GAA-TTC-TGT-TAG-AAA-AGC-CAC-CAG-AGA-AAT-G, 203–227) and reverse primer (CTC-GAG-CTC-TCT-TGT-TTC-TTC-CTC-TGC-TG, 1664–1686) are used to synthesize the 1484 bp fragment coding for the phosphorylation site and both low and high affinity cGMP binding sites of human PDE5A (203–1686 bp, cGB-PDE5). The synthesized cGB-PDE5 nucleotide fragment codes for 494 amino acids with 97% similarity to bovine PDE5A. It is then cloned into pGEX-5X-3 glutathione-S-transferase (GST) fusion vector (Pharmacia Biotech)with tac promoter, and EcoRI and XhoI cut sites. The fusion vector is then transfected into *E. Coli* BL21 (DE3) bacteria (Invitrogen). The transfected BL21 bacteria are grown to log phase and then IPTG is added as an inducer. The induction is carried out at 20° C. for 24 hrs. The bacteria are harvested and lysed. The soluble cell lysate is incubated with GSH conjugated Sepharose 4B (GSH-Sepharose 4B). The GST-cGB-PDE5 fusion protein can bind to the GSH-Sepharose beads, and the other proteins are washed off from the beads with excessive cold PBS.

The expressed GST-cGB-PDE5 fusion protein is displayed on 7.5% SDS-PAGE gel as an 85 Kd protein. It is characterized by its cGMP binding and phosphorylation by protein kinases G and A. It displays two cGMP binding sites and the $K_d$ is 1.6±0.2 $\mu$M, which is close to $K_d$=1.3 $\mu$M of the native bovine PDE5. The GST-cGB-PDE5 on GSH conjugated sepharose beads can be phosphorylated in vitro by cGMP-dependent protein kinase and cAMP-dependent protein kinase A. The $K_m$ of GST-cGB-PDE5 phosphorylation by PKG is 2.7 $\mu$M and the Vmax is 2.8 $\mu$M, while the $K_m$ of BPDEtide phosphorylation is 68 $\mu$M. The phosphorylation by PKG shows molecular phosphate incorporated into GST-cGB-PDE5 protein on a one-to-one ratio.

To assay a liquid sample believed to contain PKG using the PDE5-bound solid phase described above, the sample and the solid phase are mixed with phosphorylation buffer containing $^{32}$P-$\gamma$-ATP. The solution is incubated for 30 minutes at 30° C. to allow for phosphorylation of the PDE5 sequence by PKG to occur, if PKG is present. The solid phase is then separated from solution (e.g., by centrifugation or filtration) and washed with phosphate-buffered saline ("PBS") to remove any remaining solution and to remove any unreacted $^{32}$P-$\gamma$-ATP.

The solid phase can then be tested directly (e.g., by liquid scintillation counter) to ascertain whether $^{32}$P is incorporated. If $^{32}$P is incorporated, that indicates that the sample contained PKG since PKG phosphorylates PDE5. If the PDE5 is bound via fusion protein, as described above, the PDE5-containing fusion protein can be eluted from the solid phase with SDS buffer, and the eluent can be assayed for $^{32}$P incorporation. This is particularly advantageous if there is the possibility that other proteins are present, since the eluent can be processed (e.g., by gel separation) to separate various proteins from each other so that the fusion protein fraction can be assayed for $^{32}$P incorporation. The phosphorylated fusion protein can be eluted from the solid phase with SDS buffer and further resolved by electrophoresis. If gel separation is performed, the proteins can be stained to see the position(s) of the protein, and $^{32}$P phosphorylation of the PDE5 portion of the fusion protein by PKG can be measured by exposure of the gel to X-ray film. If $^{32}$P is made visible on X-ray film, that indicates that the original sample contained PKG, which phosphorylated the PDE5 portion of the fusion protein eluted from the solid phase.

Preferably in the assay, one should add to the assay buffer an excess (e.g., 100 fold of IC$_{50}$ value) of protein kinase inhibitor ("PKI") which specifically and potently inhibits protein kinase A ("PKA") without inhibiting PKG. Inhibiting PKA is desirable since it may contribute to the phosphorylation of the PKG substrate (e.g., PDE5). By adding PKI, any contribution to phosphorylation by PKA will be eliminated, and any phosphorylation detected is highly likely to be due to PKG alone.

A kit can be made for the assay of this invention, which kit contains the following pre-packaged reagents in separate containers:

1. Cell lysis buffer: 50 mM Tris-HCl, 1% NP-40, 150 mM NaCl, 1 mM EDTA, 1 mM Na$_3$VO$_4$, 1 mM NaF, 500 $\mu$M IBMX, proteinase inhibitors.
2. Protein kinase G solid phase substrate: recombinant GST-cGB-PDE5 bound Sepharose 4B (50% slurry).
3. 2× Phosphorylation buffer: $^{32}$P-$\gamma$-ATP (3000 mCi/mmol, 5~10 $\mu$Ci/assay), 10 mM KH$_2$PO$_4$, 10 mM K$_2$HPO$_4$, 200 $\mu$M ATP, 5 mM MgCl$_2$.
4. PKA Protein Kinase I Inhibitor Disposable containers and the like in which to perform the above reactions can also be provided in the kit.

From the above, one skilled in the analytical arts will readily envision various ways to adapt the assay formats described to still other formats. In short, using at least a portion of PDE5 (or any other protein that can be selectively phosphorylated by PKG), the presence and relative amount (as compared to a control) of PKG can be ascertained by evaluating phosphorylation of the phosphorylatable protein, using a labeled phosphorylation agent.

SAANDs Increase PKG Activity in Neoplastic Cells

Using the PKG assay described above, the following experiments were performed to establish that SAANDs increase PKG activity due either to increase in PKG expression or an increase in cGMP levels (or both) in neoplastic cells treated with a SAAND.

Test Procedures

Two different types of PDE inhibitors were evaluated for their effects on PKG in neoplastic cells. A SAAND, exisulind, was evaluated since it is anti-neoplastic. Also, a non-SAAND classic PDE5 inhibitor, E4021, was evaluated to ascertain whether PKG elevation was simply due to classic PDE5 inhibition, or whether PKG elevation was involved in the pro-apoptotic effect of SAANDs inhibition of PDE5 and the novel PDE disclosed in U.S. patent application Ser. No. 09/173,375 to Liu et al filed Oct. 15, 1998.

To test the effect of cGMP-specific PDE inhibition on neoplasia containing the APC mutation, SW480 colon cancer cells were employed. SW 480 is known to contain the APC mutation. About 5 million SW480 cells in RPMI 5% serum are added to each of 8 dishes:

2–10 cm dishes—30 $\mu$L DMSO vehicle control (without drug),
3–10 cm dishes—200 $\mu$M, 400 $\mu$M, 600 $\mu$M exisulind, and
3–10 cm dishes—E4021; 0.1 $\mu$M, 1 $\mu$M and 10 $\mu$M.

The dishes are incubated for 48 hrs at 37° C. in 5% CO$_2$ incubator.

The liquid media are aspirated from the dishes (the cells will attach themselves to the dishes). The attached cells are washed in each dish with cold PBS, and 200 $\mu$L cell lysis buffer (i.e., 50 mM Tris-HCl, 1% NP-40, 150 mM NaCl, 1 mM EDTA, 1 mM Na$_3$VO$_4$, 1 mM NaF, 500 µM IBMX with proteinase inhibitors) is added to each dish. Immediately after the cell lysis buffer is added, the lysed cells are collected by scraping the cells off each dish. The cell lysate from each dish is transferred to a microfuge tube, and the microfuge tubes are incubated at 4° C. for 15 minutes while gently agitating the microfuge tubes to allow the cells to lyse completely. After lysis is complete, the microfuge tubes are centrifuged full speed (14,000 r.p.m.) for 15 minutes. The supernatant from each microfuge tube is transferred to a fresh microfuge tube.

A protein assay is then performed on the contents of each microfuge tube because the amount of total protein will be greater in the control than in the drug-treated samples, if the drug inhibits cell growth. Obviously, if the drug does not work, the total protein in the drug-treated samples should be virtually the same as control. In the above situation, the control and the E-4021 microfuge tubes needed dilution to normalize them to the high-dose exisulind-treated samples (the lower dose groups of exisulind had to be normalized to the highest dose exisulind sample). Thus, after the protein assays are performed, the total protein concentration of the various samples must be normalized (e.g., by dilution).

For each drug concentration and control, two PKG assays are performed, one with added cGMP, and one without added cGMP, as described in detail below. The reason for performing these two different PKG assays is that cGMP specifically activates PKG. When PKG activity is assayed using the novel PKG assay of this invention, one cannot ascertain whether any increase the PKG activity is due to increased cGMP in the cells (that may be caused by cGMP-specific PDE inhibition) or whether the PKG activity level is due to an increased expression of PKG protein. By determining PKG activity in the same sample both with and without added cGMP, one can ascertain whether the PKG activity increase, if any, is due to increased PKG expression. Thus, if an anti-neoplastic drug elevates PKG activity relative to control, one can establish if the drug-induced increase is due to increased PKG protein expression (as opposed to activation) in the drug-treated sample if (1) the drug-treated sample with extra cGMP exhibits greater PKG activity compared to the control sample with extra cGMP, and (2) the drug-treated sample without extra cGMP exhibits greater PKG activity relative to control.

After parallel samples with and without added cGMP are prepared, 50 µL of each cell lysate is added to 20 µL of the PDE5/GST solid phase substrate slurry described above. For each control or drug cell lysate sample to be evaluated, the reaction is started by adding phosphorylation buffer containing 10 µCi $^{32}$P-γ-ATP solution (200 µM ATP, 4.5 mM MgCl; 5 mM KH$_2$PO$_4$; 5 mM K$_2$HPO$_4$;) to each mixture. The resultant mixtures are incubated at 30° C. for 30 minutes. The mixtures are then centrifuged to separate the solid phase, and the supernatant is discarded. The solid phase in each tube is washed with 700 µL cold PBS. To the solid phase, Laemmli sample buffer (Bio-Rad) (30 µL) is added. The mixtures are boiled for 5 minutes, and loaded onto 7.5% SDS-PAGE. The gel is run at 150 V for one hour. The bands obtained are stained with commassie blue to visualize the 85 Kd GST-PDE5 fusion protein bands, if present. The gel is dried, and the gel is laid on x-ray film which, if the PDE5 is phosphorylated, the film will show a corresponding darkened band. The darkness of each band relates to the degree of phosphorylation.

Figures 18A, 18B:
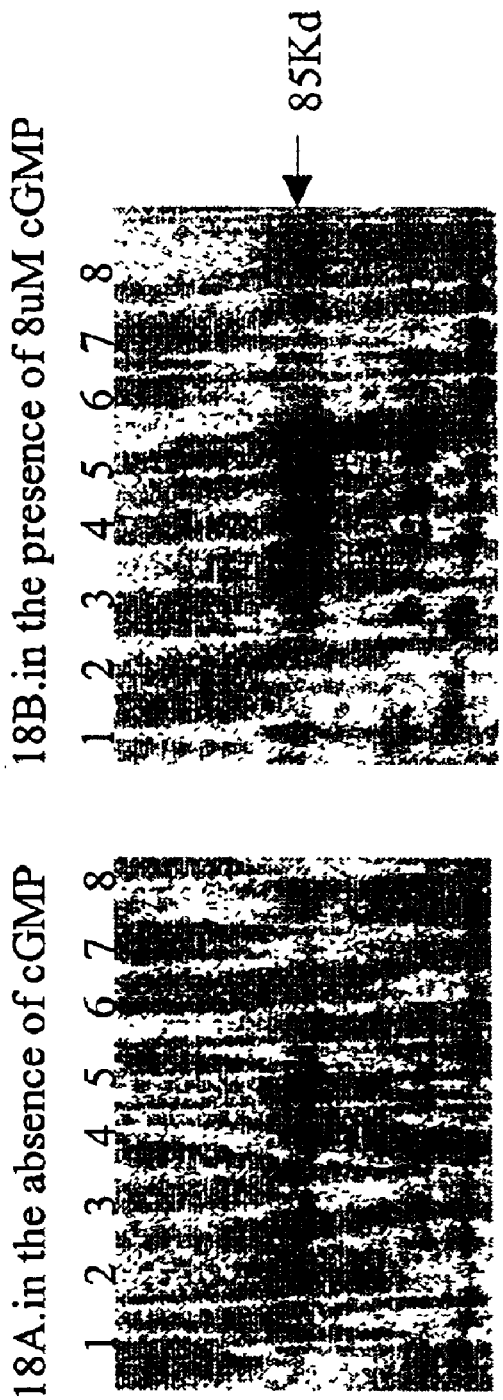
FIG. 18A is a radiography of SDS-PAGE gel of PKG activity from SW480 cells treated with drugs in the absence of added cGMP, where cells were treated in culture for 48 hours with DMSO (0.03%, lanes 1 and 2), exisulind (200, 400 and 600 $\mu$M; lanes 3, 4, 5) and E4021 (0.1, 1 and 10 $\mu$M, lanes 6, 7, 8).
FIG. 18B is a radiography of the SDS-PAGE gel of PKG activity from SW480 cells treated with drugs in the presence of added cGMP, where cells were treated in culture for 48 hours with DMSO (0.03%, lanes 1 and 2), exisulind (200, 400 and 600 $\mu$M; lanes 3, 4, 5) and E4021 (0.1, 1 and 10 $\mu$M, lanes 6, 7, 8).

As shown in FIGS. 18A and 18B, the SAAND exisulind causes PKG activity to increase in a dose-dependent manner in both the samples with added cGMP and without added cGMP relative to the control samples with and without extra cGMP. This is evidenced by the darker appearances of the 85 Kd bands in each of the drug-treated samples. In addition, the SW480 samples treated with exisulind show a greater PKG phosphorylation activity with added cGMP in the assay relative to the samples treated with vehicle with added cGMP. Thus, the increase in PKG activity in the drug-treated samples is not due only to the activation of PKG by the increase in cellular cGMP when the SAAND inhibits cGMP-specific PDE, the increase in PKG activity in neoplasia harboring the APC mutation is due to increased PKG expression as well.

Also the fact that the E4021-treated SW480 samples do not exhibit PKG activation relative to control (see FIGS. 18A and 18B) shows that the increased PKG activation caused by SAANDs in neoplasia containing the APC mutation is not simply due to inhibition of classic PDE5.

As an analytic technique for evaluating PKG activation, instead of x-ray film exposure as described above, the 85 Kd band from the SDS page can be evaluated for the degree of phosphorylation by cutting the band from the gel, and any $^{32}$P incorporated in the removed band can be counted by scintillation (beta) counter in the $^{32}$P window.

To test the effect of cGMP-specific PDE inhibition on neoplasia containing the β-catenin mutation, HCT116 colon cancer cells were employed. HCT116 is known to contain the β-catenin mutation, but is known not to contain the APC mutation.

The same procedure is used to grow the HCT116 cells as is used in the SW480 procedure described above. In this experiment, only exisulind and controls were used. The exisulind-treated cells yielded PKG that was phosphorylated to a greater extent than the corresponding controls, indicating that PKG activation occurred in the drug-treated cells that is independent of the APC mutation.

Thus, for the purposes of the present invention, "β-catenin" refers to wild type and/or mutant forms of that protein.

Confirmation of Increased PKG Expression and Decreased β-Catenin in SW 480 by Western Blot As demonstrated above, SAANDs cause an increase in PKG expression and an increase in cGMP level, both of which cause an increase in PKG activity in SAANDs-treated neoplastic cells. This increase in PKG protein expression was further verified by relatively quantitative western blot, as described below.

SW480 cells treated with exisulind as described previously are harvested from the microfuge tubes by rinsing once with ice-cold PBS. The cells are lysed by modified RIPA buffer for 15 minutes with agitation. The cell lysate is spun down in a cold room. The supernatants are transferred to fresh microcentrifuge tubes immediately after spinning. BioRad DC Protein Assay (Temecula, Calif.) is performed to determine the protein concentrations in samples. The samples are normalized for protein concentration, as described above.

50 µg of each sample is loaded onto a 10% SDS gel. SDS-PAGE is performed, and the proteins then are transferred to a nitrocellulose membrane. The blotted nitrocellulose membrane is blocked in freshly prepared TBST containing 5% nonfat dry milk for one hour at room temperature with constant agitation.

A goat-anti-PKG primary antibody is diluted to the recommended concentration/dilution in fresh TBST/5% nonfat dry milk. The nitrocellulose membrane is placed in the primary antibody solution and incubated one hour at room temperature with agitation. The nitrocellulose membrane is washed three times for ten minutes each with TBST. The nitrocellulose membrane is incubated in a solution containing a secondary peroxidase (POD) conjugated rabbit anti-goat antibody for 1 hour at room temperature with agitation. The nitrocellulose membrane is washed three times for ten minutes each time with TBST. The detection is performed by using Boehringer Mannheim BM blue POD substrate.

Figure 19:
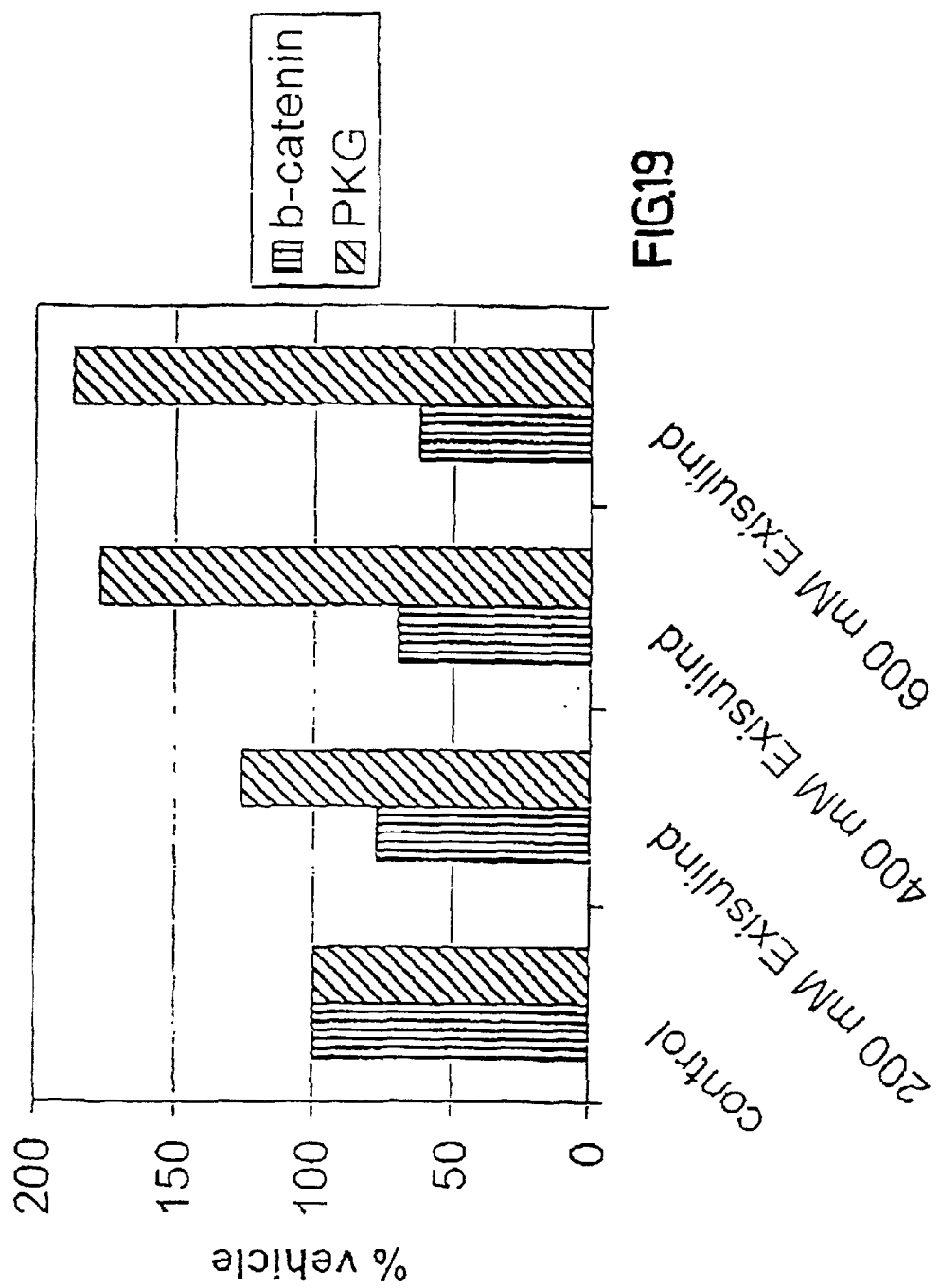
FIG. 19 is a bar graph of the results of Western blot experiments of the effects of exisulind on $\beta$-catenin and PKG levels in neoplastic cells relative to control.

As graphically illustrated in FIG. 19, exisulind causes the drop of β-catenin and the increase of PKG, which data were obtained by Western blot. SW480 cells were treated with exisulind or vehicle (0.1% DMSO) for 48 hours. 50 μg supernatant of each cell lysate was loaded onto a 10% SDS-gel and blotted to a nitrocellulose membrane, and the membrane was probed with rabbit-anti-β-catenin and rabbit anti-PKG antibodies.

SAANDs Reduce β-Catenin Levels in Neoplastic Cells

This observation was made by culturing SW480 cells with either 200, 400 or 600 μM exisulind or vehicle (0.1% DMSO). The cells are harvested 48 hours post treatment and processed for immunoblotting. Immuno-reactive protein can be detected by Western blot. Western blot analysis demonstrated that expression of β-catenin was reduced by 50% in the exisulind-treated cells as compared to control. These results indicate that β-catenin is reduced by SAANDs treatment. Together with the results above, establishing PKG activity increases with such treatment, and the results below, establishing that β-catenin is phosphorylated by PKG, these results indicate that the reduction of β-catenin in neoplastic cells is initiated by activation of PKG. Thus, using PKG activity in neoplasia as a screening tool to select compounds as anti-neoplastics is useful.

The Phosphorylation of β-catenin by PKG

In vitro PKG phosphorylates β-catenin. The experiment that established this involves immunoprecipitating the β-catenin-containing complex from SW480 cells (not treated with any drug) in the manner described below under "β-catenin immunoprecipitation." The immunoprecipitated complex, while still trapped on the solid phase (i.e., beads) is mixed with $^{32}$P-γ-ATP and pure PKG (100 units). Corresponding controls without added PKG are prepared.

The protein is released from the solid phase by SDS buffer, and the protein-containing mixture is run on a 7.5% SDS-PAGE gel. The running of the mixture on the gel removes excess $^{32}$P-γ-ATP from the mixture. Any $^{32}$P-γ-ATP detected in the 93Kd β-catenin band, therefore, is due to the phosphorylation of the β-catenin. Any increase in $^{32}$P-γ-ATP detected in the 93 Kd β-catenin band treated with extra PKG relative to the control without extra PKG, is due to the phosphorylation of the β-catenin in the treated band by the extra PKG.

The results we obtained were that there was a noticeable increase in phosphorylation in the band treated with PKG as compared to the control, which exhibited minimal, virtually undetectable phosphorylation. This result indicates that β-catenin can be phosphorylated by PKG.

The Phosphorylation of Mutant β-Catenin by PKG

The same procedure described in the immediately preceding section was performed with HCT116 cells, which contain no APC mutation, but contain a β-catenin mutation. The results of those experiments also indicate that mutant β-catenin is phosphorylated by PKG.

Thus, for the purposes of the present invention, the phosphorylation of β-catenin refers to the phosphorylation of wild type and/or mutant forms of that protein.

β-Catenin Precipitates with PKG

Supernatants of both SW480 and HCT116 cell lysates are prepared in the same way described above in the Western Blot experiments. The cell lysates are pre-cleared by adding 150 μl of protein A Sepharose bead slurry (50%) per 500 μg of cell lysate and incubating at 4° C. for 10 minutes on a tube shaker. The protein A beads are removed by centrifugation at 14,000×g at 4° C. for 10 minutes. The supernatants are transferred to a fresh centrifuge tubes. 10 μg of the rabbit polyclonal anti-β-catenin antibody (Upstate Biotechnology, Lake Placid, N.Y.) are added to 500 μg of cell lysate. The cell lysate/antibody mixture is gently mixed for 2 hours at 4° C. on a tube shaker. The immunocomplex is captured by adding 150 μl protein A Sepharose bead slurry (75 μl packed beads) and by gently rocking the mixture on a tube shaker for overnight at 4° C. The Sepharose beads are collected by pulse centrifugation (5 seconds in the microcentrifuge at 14,000 rpm). The supernatant fraction is discarded, and the beads are washed 3 times with 800 μl ice-cold PBS buffer. The Sepharose beads are resuspended in 150 μl 2× sample buffer and mixed gently. The Sepharose beads are boiled for 5 minutes to dissociate the immunocomplexes from the beads. The beads are collected by centrifugation and SDS-PAGE is performed on the supernatant.

A Western blot is run on the supernatant, and the membrane is then probed with a rabbit-anti-β-catenin antibody. Then the membrane is washed 3 times for 10 minutes each time with TBST to remove excess anti-β-catenin antibody. A goat, anti-rabbit antibody conjugated to horseradish peroxidase is added, followed by a one hour incubation at room temperature. When that is done, one can visualize the presence of β-catenin with an HRPO substrate. In this experiment, we could clearly visualize the presence of β-catenin.

To detect PKG on the same membrane, the anti-β-catenin antibody conjugate is first stripped from the membrane with a 62 mM tris-HCl buffer (pH 7.6) with 2% SDS and 100 μM 2β-mercaptoethanol in 55° C. water bath for 0.5 hour. The stripped membrane is then blocked in TBST with 5% non-fat dried milk for one hour at room temperature while agitating the membrane. The blocked, stripped membrane is then probed with rabbit polyclonal anti-PKG antibody (Calbiochem, LaJolla, Calif.), that is detected with goat, anti-rabbit second antibody conjugated to HRPO. The presence of PKG on the blot membrane is visualized with an HRPO substrate. In this experiment, the PKG was, in fact, visualized. Given that the only proteins on the membrane are those that immunoprecipitated with β-catenin in the cell supernatants, this result clearly establishes that PKG was physically linked to the protein complex containing the β-catenin in the cell supernatants.

The same Western blot membrane was also probed after stripping with anti-GSK3-β antibody to ascertain whether it also co-precipitated with β-catenin. In that experiment, we also detected GSK3-β on the membrane, indicating that the GSK3-β precipitated with the GSK3-β and PKG, suggesting that the three proteins may be part of the same complex. Since GSK3-β and β-catenin form part of the APC complex in normal cells, this indicates that PKG may be part of the same complex, and may be involved in the phosphorylation of β-catenin as part of that complex.

Anti-Neoplastic Pharmaceutical Compositions Containing cGMP PDE Inhibitors

One drug that was also invented before its mechanism of action was found to involve cGMP inhibition and before it was known to meet the selection criterion of this invention is (Z)-5-fluoro-2-methyl-(4-pyridylidene)-3-(N-benzyl) indenylacetamide hydrochloride ("Compound I") (see "General Schemes for Producing cGMP-Specific PDE Inhibitors" above). It has been demonstrated in in vitro and in vivo evaluations as anti-neoplastic having activities against a broad range of neoplasias. It is also safe in animal studies and in a single, escalating dose human study.

As one skilled in the art will recognize from the data presented below, Compound I can safely be given to animals at doses far beyond the tolerable (and in many cases toxic) doses of conventional chemotherapeutics or anti-neoplastic NSAIDs. For example, in an acute toxicity study in rats, single oral doses of Compound I administered (in a 0.5% carboxy-methylcellulose vehicle) at doses up to and including 2000 mg/kg resulted in no observable signs of toxicity. At 4000 mg/kg, body weight gains were slightly reduced. A single dose of 1000 mg/kg administered intraperitoneally resulted in reduced body weight gain, with mesenteric adhesions seen in some animals from this group at necropsy.

In dogs, the administration of Compound I in capsules at 1000 mg/kg resulted in no signs of toxicity to the single group of two male and two female dogs. Due to the nature of Compound I capsules, this dose necessitated the use of at least 13 capsules to each animal, which was judged to be the maximum number without subjecting the animals to stress. Therefore, these dogs were subsequently administered seven consecutive doses of 1000 mg/kg/day. At no time in either dosing phase were any obvious signs of drug-related effects observed.

Thus, on a single-dose basis, Compound I is not acutely toxic. Based on the findings of these studies, the oral $LD_{50}$ of Compound I was considered to be greater than 1000 mg/kg in dogs and 4000 mg/kg in rats, and the intraperitoneal $LD_{50}$ was considered to be greater than 1000 mg/kg in rats.

A seven-day dose-range finding study in rats, where Compound I was evaluated by administering it at doses of 0, 50, 500 or 2000 mg/kg/day resulted in no observable signs of toxicity at 50 mg/kg/day. At 500 mg/kg/day, treatment-related effects were limited to an increase in absolute and relative liver weights in female rats. At 2000 mg/kg/day, effects included labored breathing and/or abnormal respiratory sounds, decreased weights gains and food consumption in male rats, and increased liver weights in female rats. No hematological or blood chemistry changes nor any microscopic pathology changes, were seen at any dose level.

A 28-day study in rats was also carried out at 0, 50, 500 and 2000 mg/kg/day. There were no abnormal clinical observations attributed to Compound I, and body weight changes, ophthalmoscopic examinations, hematological and blood chemistry values and urinalysis examinations were unremarkable. No macroscopic tissue changes were seen at necropsy. Organ weight data revealed statistically significant increase in liver weights at 2000 mg/kg/day, and statistically significant increases in thyroid weights for the 2000 mg/kg/day group. The slight increases at the lower doses were not statistically significant. Histopathological evaluation of tissues indicated the presence of traces of follicular cell hypertrophy, increased numbers of mitotic figures (suggestive of possible cell proliferation) in the thyroid gland and mild centrilobular hypertrophy in the liver. These changes were generally limited to a small number of animals at the 2000 mg/kg/day dose, although one female at 500 mg/kg/day had increased mitotic figures in the thyroid gland. The findings in the liver may be indicative of a very mild stimulation of microsomal enzymes, resulting in increased metabolism of thyroid hormones, which in turn resulted in thyroid stimulation. Thus, one skilled in the art will recognize that these effects are extremely minimal compared to what one would expect at similar doses of conventional chemotherapeutics or NSAIDs.

To further establish the safety profile of Compound I, a study was performed to evaluate whether Compound I-induced apoptosis of prostate tumor cell lines was comparable to its effects on prostate epithelial cells derived from normal tissue. The androgen-sensitive prostate tumor cell line, LNCaP (from ATCC (Rockville, Md.)) was propagated under standard conditions using RPMI 160 medium containing 5% fetal calve serum and 2 mM glutamine. Primary prostate epithelial cell cultures (PrEC) derived from normal prostate (from Clonetics Inc. (San Diego, Calif.)) were grown under the same conditions as the tumor cell line except a serum-free medium optimized for the growth of such cultures was used (Clonetics Inc). For the experiments, LNCaP or PrEC cells were seeded in 96 well plates at a density of 10,000 cells per well. After 24 hours, the cells were treated with either vehicle (0.1% DMSO) or 50 $\mu$M Compound I (free base) solubilized in DMSO. After various drug treatment times (4, 24, 48, 72, or 99 hours) the cells were lysed and processed for measurement of histone-associated DNA as an indicator of apoptotic cell death (see, Piazza et al., *Cancer Research* 57: 2452–2459, 1997).

Figure 27B:
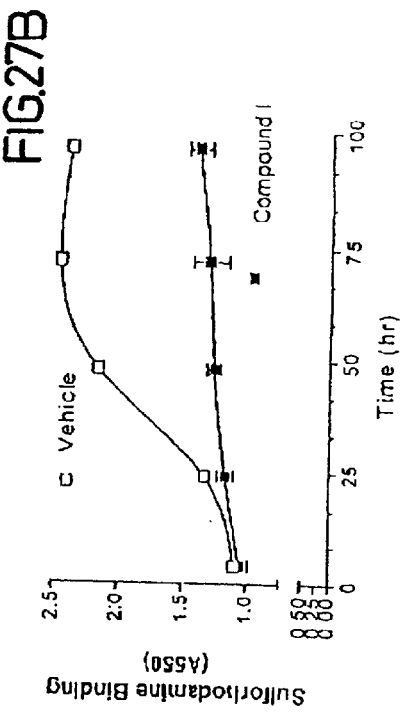
FIG. 27B shows the course of treatment of PrEC prostate cells with Compound I (50 $\mu$M) that did not affect DNA fragmentation for up to 4 days of treatment.
Figure 27A:
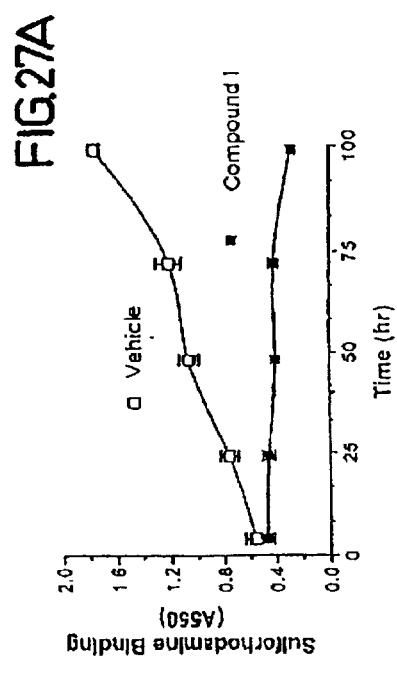
FIG. 27A shows a time-dependent increase in the amount of histone-associated fragmented DNA in LNCaP cell cultures following treatment with 50 $\mu$M Compound I.

FIG. 27 shows a time-dependent increase in the amount of histone-associated fragmented DNA in LNCaP cell cultures following treatment with 50 $\mu$M Compound I(free base). A significant increase in fragmented DNA was detected after 24 hours of treatment, and the induction was sustained for up to 4 days of continuous treatment. By contrast, treatment of PrEC ("normal" prostate) cells with Compound I (50 $\mu$M) did not affect DNA fragmentation for up to 4 days of treatment. These results demonstrate a selective induction of apoptosis in neoplastic cells, as opposed to normal cells. This is in marked contrast to conventional chemotherapeutics that induce apoptosis or necrosis in rapidly growing normal and neoplastic cells alike.

Identification of Additional Inhibitors

As to identifying structurally additional cGMP-specific PDE inhibiting compounds that can be effective therapeutically as anti-neoplastics, one skilled in the art has a number of useful model compounds disclosed herein (as well as their analogs incorporated by reference) that can be used as the bases for computer modeling of additional compounds having the same conformations but different chemically. For example, software such as that sold by Molecular Simulations Inc. release of WebLab® ViewerPro™ includes molecular visualization and chemical communication capabilities. Such software includes functionality, including 3D visualization of known active compounds to validate sketched or imported chemical structures for accuracy. In addition, the software allows structures to be superimposed based on user-defined features, and the user can measure distances, angles, or dihedrals.

In this situation, since the structures of other active compounds are disclosed above, one can apply cluster analysis and 2D and 3D similarity search techniques with such software to identify potential new additional compounds that can then be screened and selected according to the selection criteria of this invention. These software methods rely upon the principle that compounds, which look alike or have similar properties, are more likely to have similar activity, which can be confirmed using the selection criterion of this invention.

Likewise, when such additional compounds are computer modeled, many such compounds and variants thereof can be synthesized using known combinatorial chemistry techniques that are commonly used by those of ordinary skill in the pharmaceutical industry. Examples of a few for-hire combinatorial chemistry services include those offered by New Chemical Entities, Inc. of Bothell Wash., Protogene Laboratories, inc., of Palo Alto, Calif., Axys, Inc. of South San Francisco, Calif., Nanosyn, Inc. of Tucson, Ariz., Trega, Inc. of San Diego, Calif., and RBI, Inc. of Natick, Mass. There are a number of other for-hire companies. A number of large pharmaceutical companies have similar, if not superior, in-house capabilities. In short, one skilled in the art can readily produce many compounds for screening from which to select promising compounds for treatment of neoplasia having the attributes of compounds disclosed herein.

In addition, there are a number of commercially-known libraries of compounds usually made with combinatorial techniques. Such compounds can first be assessed using the types of software explained above to ascertain whether they are conformationally similar to active compounds of the types disclosed herein. After identifying such conformationally similar compounds, the compounds can readily be screened according to the methods of this invention to yield anti-neoplastic cGMP PDE inhibitors.

To further assist in identifying compounds that can be screened and then selected using the criterion of this invention, knowing the binding of selected anti-neoplastic compounds to PDE5 protein is of interest. By the procedures discussed below, it was found that preferable, desirable compounds meeting the selection criteria of this invention bind to the cGMP catalytic region of PDE5.

To establish this, a PDE5 sequence that does not include the catalytic domain was used. One way to produce such a sequence is to express that sequence as a fusion protein, preferably with glutathione S-transferase ("GST"). Production of a GST-cGB-PDE5 fusion protein was carried out by the procedure described above in the section entitled *The Novel PKG Assay*.

A cGMP binding assay for compounds of interest (Francis S. H. et al, J. Biol. Chem. 255, 620–626, 1980) is done in a total volume of 100 µL containing 5 mM sodium phosphate buffer (pH=6.8), 1 mM EDTA, 0.25 mg/mL BSA, $H^3$-cGMP (2 µM, NEN) and the GST-cGB-PDE5 fusion protein (30 µg/assay). Each compound to be tested is added at the same time as $^3$H-cGMP substrate, and the mixture is incubated at 22° C. for 1 hour. Then, the mixture is transferred to Brandel MB-24 cell harvester with GF/B as the filter membrane followed by 2 washes with 10 mL of cold 5 mM potassium buffer (pH 6.8). The membranes are then cut out and transferred to scintillation vials followed by the addition of 1 mL of $H_2O$ and 6 mL of Ready Safe™ liquid scintillation cocktail to each vial. The vials are counted on a Beckman LS 6500 scintillation counter.

For calculation, blank samples are prepared by boiling the binding protein for 5 minutes, and the binding counts are <1% when compared to unboiled protein. The quenching by filter membrane or other debris are also calibrated.

Figure 24:
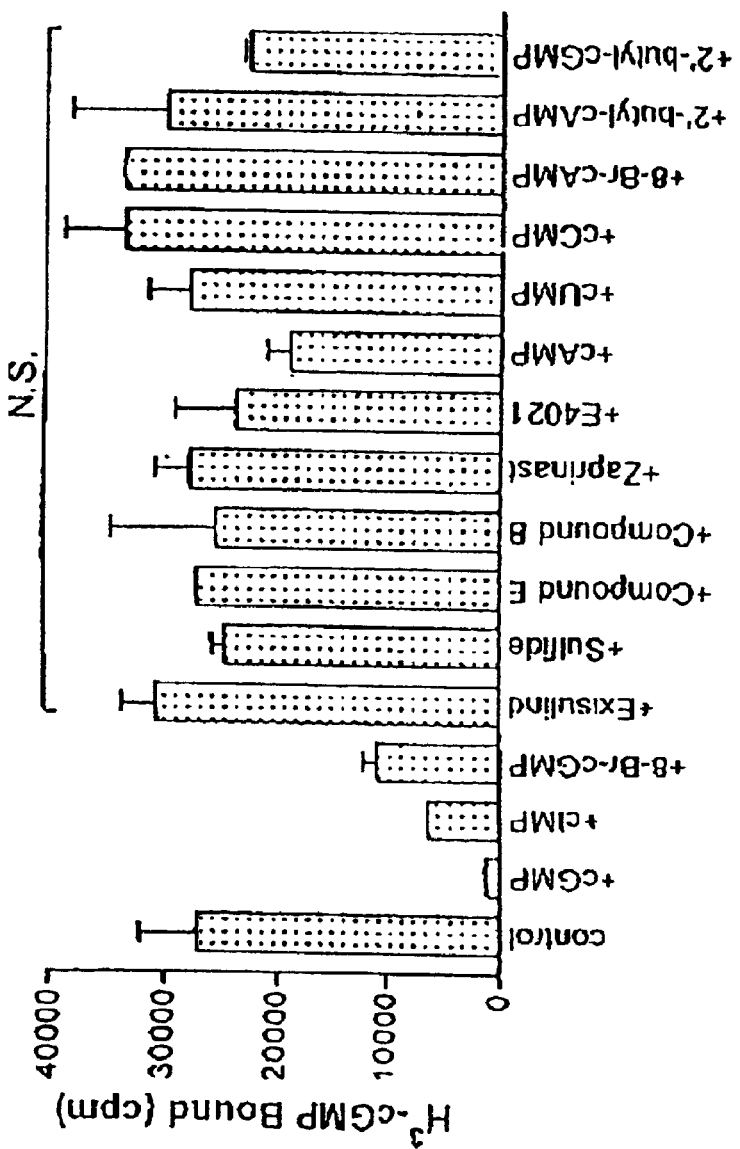
FIG. 24 is a bar graph illustrating the specificity binding of the non-catalytic cGMP binding sites of PDE5 for cyclic nucleotide analogs and selected PDE5 inhibitors.

PDE5 inhibitors, sulfide, exisulind, Compound B, Compound E, E4021 and zaprinast, and cyclic nucleotide analogs, cAMP, cyclic IMP, 8-bromo-cGMP, cyclic UMP, cyclic CMP, 8-bromo-cAMP, 2'-O-butyl-cGMP and 2'-O-butyl-cAMP are selected to test whether they could competitively bind to the cGMP binding sites of the GST-cGB-PDE5 protein. The results were shown in FIG. 24. cGMP specifically binds GST-cGB-PDE5 protein. Cyclic AMP, cUMP, cCMP, 8-bromo-cAMP, 2'-O-butyl-cAMP and 2'-O-butyl-cGMP did not compete with cGMP in binding. Cyclic IMP and 8-bromo-cGMP at high concentration (100 µM) can partially compete with cGMP (2 µM) binding. None of the PDE5 inhibitors showed any competition with cGMP in binding of GST-cGB-PDE5. Therefore, they do not bind to the cGMP binding sites of PDE5.

However, Compound E does competitively (with cGMP) bind to PDE 5 (i.e., Peak A). (Compound E also competitively (with cGMP) binds to PDE Peak B.). Given that Compound E does not bind to the cGMP-binding site of PDE5, the fact that there is competitive binding between Compound E and cGMP at all means that desirable compounds such as Compound E bind to the cGMP catalytic site on PDE5, information that is readily obtainable by one skilled in the art (with conventional competitive binding experiments) but which can assist one skilled in the art more readily to model other compounds. Thus, with the chemical structures of desirable compounds presented herein and the cGMP binding site information, one skilled in the art can model, identify and select (using the selection criteria of this invention) other chemical compounds for use as therapeutics.

A Human Epidermal Growth Factor Receptor Tyrosine Kinase Inhibitor

The present invention discloses using a human epidermal growth tyrosine kinase inhibitor in combination with a cGMP-specific PDE inhibitor to treat a patient with cancer. One such human epidermal growth tyrosine kinase inhibitor disclosed for use herein in combination with a cGMP-specific PDE inhibitor is Iressa, also called ZD1839. Iressa is an inhibitor of epidermal growth factor receptor tyrosine kinase (EGFR-TK), with specificity against the EGFR.

Iressa is an orally active inhibitor which blocks signal transduction pathways implicated in promoting cancer growth (WO02/28409; WO020020; WO02/005791; WO02/002534; WO01/076586; each of which are incorporated herein by reference). Iressa reportedly has antiangiogenic activity, it has antitumor activity against such cancers as colon, breast, ovarian, gastric, non-small lung cancer, pancreatic prostate, and leukemia, it eliminates EGFR, HER2, and HER3 phosphorylation, it inhibits human breast xenograft growth and it has been used in patients (Ciardello et al., 2001, Cancer Res. 7:5:1459–1465; Moulder et al., 2001, Cancer Res. 61:24:8887–8895; Barker et al., 2001, Bioorganic and Medicinal Chemistry Letters 11:14:1911–1914; Moasser et al. 2001, Cancer Res. 61:19:7184–7188; Chan et al., 2002, Cancer Res. 62:1:122–128; Ranson et al., 2002, J. Clin. Oncology 20:9:2240–2250; WO01/076586).

Iressa is a quinazoline and has the chemical name 4-quinazolinamine, N-(3-chloro-4-fluorophenyl)-7-methoxy-6-[3-(4-morpholinyl)propoxy]-(9CI) and the chemical formula C22H24ClFN4O3. Iressa's structure is as follows:

Iressa/ZD-1839

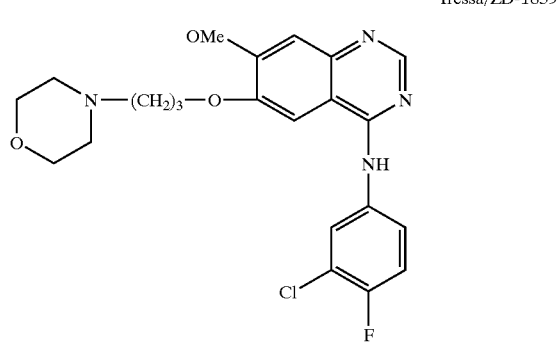

Combination Treatment with a Human Epidermal Growth Factor Receptor Tyrosine Kinase Inhibitor and a cGMP-Specific PDE Inhibitor The invention discloses a method which encompasses treating a patient with neoplasia with both an inhibitor of human epidermal growth factor receptor tyrosine kinase such as Iressa, and a cGMP-specific PDE inhibitor. By treating a patient with this combination, therapeutic results can be achieved that are not seen with either therapy alone. Such combination therapy enhances the benefit to the patient without increasing harmful side effects. For example, exisulind is one cGMP-specific PDE inhibitor that can be used in combination with an inhibitor of human epidermal growth factor receptor tyrosine kinase in this invention. The invention includes Iressa, a member of the family of inhibitors of human epidermal growth factor receptor tyrosine kinase.

As explained above, exisulind is one example of an appropriate cGMP-specific PDE inhibitor to be used in combination with an inhibitor of human epidermal growth factor receptor tyrosine kinase in the practice of this invention. Exisulind inhibits both PDE5 and PDE2, and treatment of neoplastic cells with exisulind results in growth inhibition and apoptosis (See Table 8). In another aspect of the invention the cGMP-specific PDE inhibitor is (Z)-5-fluoro-2-methyl-(4-pyridylidene)-3-(N-benzyl)indenylacetamide hydrochloride, also called CP461 (see "General Schemes for Producing cGMP-Specific PDE Inhibitors," and also see "Anti-Neoplastic Pharmaceutical Compositions Containing cGMP PDE Inhibitors," above).

Exisulind has no clinically significant side effects when administered at its recommended dose of 300–400 mg/day. When administered at doses higher than the recommended therapeutic levels, treatment with exisulind can lead to elevated levels of liver enzymes. This effect is reversible, and liver enzymes return to normal levels when the administered dose of exisulind returns to the traditionally recommended level or when treatment is discontinued. The purpose of using combinations is to allow a lower dose of each to be used. Similarly, (Z)-5-fluoro-2-methyl-(4-pyridylidene)-3-(N-benzyl)indenylacetamide hydrochloride has minimal effects on the liver (see "Anti-Neoplastic Pharmaceutical Compositions Containing cGMP PDE Inhibitors," above).

For treatment of cancer, a common dose of an inhibitor of human epidermal growth factor receptor tyrosine kinase such as Iressa may be 10–200 mg/kg/day (Chan et al., 2002, Cancer Res. 62:1:122–128; Ranson et al., 2002, J. Clin. Oncology 20:9:2240–2250). In each of the aforementioned methodologies, the inhibitor of the human epidermal growth factor receptor tyrosinase kinase and the PDE inhibitor may be administered simultaneously or in succession/alternatingly. Either may be delivered first. In one aspect of the invention the inhibitor of the human epidermal growth factor receptor tyrosinase kinase is Iressa. In another aspect of the invention the cGMP-specific PDE inhibitor is exisulind, and in yet another aspect it is (Z)-5-fluoro-2-methyl-(4-Pyridylidene)-3-(N-benzyl)indenylacetamide hydrochloride. The use of (Z)-5-fluoro-2-methyl-(4-Pyridylidene)-3-(N-benzyl)indenylacetamide hydrochloride is described more fully above in "Anti-Neoplastic Pharmaceutical Compositions Containing cGMP PDE Inhibitors. The invention should be construed to include other human epidermal growth factor tyrosine kinase inhibitors and cGMP-specific PDE inhibitors as described herein or as known to those of skill in the art.

The disclosures of each and every patent, patent application, and publication cited herein are hereby incorporated herein by reference in their entirety.

Obviously, numerous modifications and variations of the present invention are possible in light of the above teachings. It is therefore to be understood that within the scope of the appended claims, the invention may be practiced otherwise than as specifically described herein.

We claim:

1. A method of inhibiting the growth of neoplastic lesions in a patient comprising administering to said patient Iressa and the cGMP-specific phosphodiesterase inhibitor (Z)-5-fluoro-2-methyl-(4-pyridylidene)-3-(N-benzyl)indenylacetamide hydrochloride.

2. The method of claim 1, wherein Iressa is administered simultaneously with (Z)-5-fluoro-2-methyl-(4-pyridylidene)-3-(N-benzyl)indenylacetamide hydrochloride.

3. The method of claim 1, wherein Iressa is administered alternatingly with (Z)-5-fluoro-2-methyl-(4-pyridylidene)-3-(N-benzyl)indenylacetamide hydrochloride.

* * * * *